US010351893B2

(12) United States Patent
Donnelly et al.

(10) Patent No.: US 10,351,893 B2
(45) Date of Patent: Jul. 16, 2019

(54) REAGENT CARTRIDGE FOR DETECTION OF CELLS

(71) Applicant: GeneWeave Biosciences, Inc., Los Gatos, CA (US)

(72) Inventors: Doran Donnelly, Redwood City, CA (US); Werner Frei, Los Gatos, CA (US); Ryan Griswold, Los Gatos, CA (US); Lance Page, Hollister, CA (US); Shaunak Roy, Sunnyvale, CA (US)

(73) Assignee: GeneWeave Biosciences, Inc., Los Gatos, CA (US)

( * ) Notice: Subject to any disclaimer, the term of this patent is extended or adjusted under 35 U.S.C. 154(b) by 37 days.

(21) Appl. No.: 15/283,797

(22) Filed: Oct. 3, 2016

(65) Prior Publication Data

US 2017/0096697 A1  Apr. 6, 2017

Related U.S. Application Data

(60) Provisional application No. 62/237,177, filed on Oct. 5, 2015.

(51) Int. Cl.
*B01L 9/00* (2006.01)
*C12Q 1/04* (2006.01)
(Continued)

(52) U.S. Cl.
CPC ............... *C12Q 1/04* (2013.01); *B01L 3/502* (2013.01); *B01L 3/52* (2013.01); *C12Q 1/66* (2013.01);
(Continued)

(58) Field of Classification Search
CPC ....... B01L 2400/0478; B01L 2300/044; B01L 2300/0858
(Continued)

(56) References Cited

U.S. PATENT DOCUMENTS 3,122,420 A    2/1964  Rebar et al.
3,826,574 A    7/1974  Brown, Jr.
(Continued)

FOREIGN PATENT DOCUMENTS

CA          1094477        1/1981
DE      1994/4423935 A1    1/1996
(Continued)

OTHER PUBLICATIONS

International Search Report and Written Opinion for International Application No. PCT/US2014/023422, dated Sep. 8, 2014.
(Continued)

*Primary Examiner* — Natalia Levkovich

(57) ABSTRACT

An apparatus includes a housing and an actuator. The housing, which defines a reagent volume that can receive a reagent container, can be removably coupled to a reaction chamber. A delivery portion of the housing defines a delivery path between the reagent volume and the reaction chamber when the housing is coupled to the reaction chamber. The delivery path includes a protrusion such that the delivery path has a discontinuous inner surface. The actuator can be moved to convey a reagent from the reagent container into the reaction chamber via the delivery path.

16 Claims, 29 Drawing Sheets

(51) Int. Cl.
*B01L 3/00* (2006.01)
*C12Q 1/66* (2006.01)

(52) U.S. Cl.
CPC . *C12Y 113/12007* (2013.01); *B01L 2200/141* (2013.01); *B01L 2200/16* (2013.01); *B01L 2300/044* (2013.01); *B01L 2300/047* (2013.01); *B01L 2300/0672* (2013.01); *B01L 2300/0858* (2013.01); *B01L 2400/0478* (2013.01); *B01L 2400/0481* (2013.01); *B01L 2400/086* (2013.01); *G01N 2333/195* (2013.01); *G01N 2333/90241* (2013.01)

(58) Field of Classification Search
USPC .......................................... 422/550, 570, 921
See application file for complete search history.

(56) References Cited

U.S. PATENT DOCUMENTS

| | | | |
|---|---|---|---|
| 4,057,148 A | 11/1977 | Meyer et al. | |
| 4,730,933 A | 3/1988 | Lohr | |
| 4,861,709 A | 8/1989 | Ulitzur et al. | |
| 5,086,233 A | 2/1992 | Stafford et al. | |
| 5,128,104 A | 7/1992 | Murphy et al. | |
| 5,139,745 A | 8/1992 | Barr et al. | |
| 5,188,455 A | 2/1993 | Hammerstedt | |
| 5,221,623 A | 6/1993 | Legocki et al. | |
| 5,242,660 A | 9/1993 | Hsei | |
| 5,364,591 A | 11/1994 | Green et al. | |
| 5,447,687 A | 9/1995 | Lewis et al. | |
| 5,447,836 A | 9/1995 | Wolber et al. | |
| 5,494,646 A | 2/1996 | Seymour | |
| 5,498,525 A | 3/1996 | Rees et al. | |
| 5,582,969 A | 12/1996 | Pearson et al. | |
| 5,637,874 A | 6/1997 | Honzawa et al. | |
| 5,645,801 A | 7/1997 | Bouma et al. | |
| 5,656,424 A | 8/1997 | Jurgensen et al. | |
| 5,677,124 A | 10/1997 | DuBois et al. | |
| 5,730,938 A | 3/1998 | Carbonari et al. | |
| 5,736,388 A | 4/1998 | Chada et al. | |
| 5,814,022 A | 9/1998 | Antanavich et al. | |
| 5,824,468 A | 10/1998 | Scherer et al. | |
| 5,858,693 A | 1/1999 | Cottingham | |
| 5,912,119 A | 6/1999 | Radman et al. | |
| 5,917,592 A | 6/1999 | Skiffington | |
| 5,919,625 A | 7/1999 | DuBois et al. | |
| 5,939,262 A | 8/1999 | Pasloske et al. | |
| 5,965,415 A | 10/1999 | Radman et al. | |
| 5,989,499 A | 11/1999 | Catanzariti et al. | |
| 6,144,448 A | 11/2000 | Mitoma | |
| 6,189,580 B1 | 2/2001 | Thibault et al. | |
| 6,218,176 B1 | 4/2001 | Berthold et al. | |
| 6,271,034 B1 | 8/2001 | Bardarov et al. | |
| 6,300,061 B1 | 10/2001 | Jacobs, Jr. et al. | |
| 6,326,208 B1 | 12/2001 | Denney | |
| 6,332,581 B1 | 12/2001 | Yoshihara et al. | |
| 6,451,258 B1 | 9/2002 | Malmqvist | |
| 6,544,729 B2 | 4/2003 | Sayler et al. | |
| 6,555,312 B1 | 4/2003 | Nakayama | |
| 6,719,719 B2 | 4/2004 | Carmel et al. | |
| 6,818,185 B1 | 11/2004 | Petersen et al. | |
| 7,001,719 B2 | 2/2006 | Wicks et al. | |
| 7,087,226 B2 | 8/2006 | Ramachandran et al. | |
| 7,125,727 B2 | 10/2006 | Massaro | |
| 7,160,511 B2 | 1/2007 | Takahashi et al. | |
| 7,166,425 B2 | 1/2007 | Madonna et al. | |
| 7,244,612 B2 | 7/2007 | Goodridge | |
| 7,284,900 B2 | 10/2007 | Mayer | |
| 7,364,843 B2 | 4/2008 | Peak | |
| 7,695,682 B2 | 4/2010 | Chojnacki et al. | |
| 7,794,656 B2 | 9/2010 | Liang et al. | |
| 7,854,104 B2 | 12/2010 | Cronin et al. | |
| 7,972,773 B2 | 7/2011 | Madonna et al. | |
| 8,021,343 B2 | 9/2011 | Nalesso et al. | |
| 8,057,756 B2 | 11/2011 | Londo et al. | |
| 8,092,990 B2 | 1/2012 | Voorhees | |
| 8,124,024 B2 | 2/2012 | Ching et al. | |
| 8,153,119 B2 | 4/2012 | Collins et al. | |
| 8,182,804 B1 | 5/2012 | Collins et al. | |
| 8,216,780 B2 | 7/2012 | Smith et al. | |
| 8,329,889 B2 | 12/2012 | Collins et al. | |
| 8,377,398 B2 | 2/2013 | McDevitt et al. | |
| 8,455,186 B2 | 6/2013 | Smith et al. | |
| 8,530,178 B2 | 9/2013 | Sobek et al. | |
| 8,619,257 B2 | 12/2013 | Plowman et al. | |
| 8,829,473 B1 | 9/2014 | Griswold et al. | |
| 9,133,497 B2 | 9/2015 | Frei et al. | |
| 9,388,453 B2 | 7/2016 | Rey et al. | |
| 9,481,903 B2 | 11/2016 | Rey et al. | |
| 2002/0001539 A1 | 1/2002 | DiCesare et al. | |
| 2003/0148536 A1 | 8/2003 | Liang et al. | |
| 2003/0162295 A1 | 8/2003 | Wilson | |
| 2004/0126783 A1 | 7/2004 | Bortolin et al. | |
| 2004/0170533 A1 | 9/2004 | Chu | |
| 2004/0191863 A1 | 9/2004 | Cheng et al. | |
| 2004/0214200 A1 | 10/2004 | Brown et al. | |
| 2005/0003346 A1 | 1/2005 | Voorhees et al. | |
| 2005/0048670 A1 | 3/2005 | Wu et al. | |
| 2005/0118719 A1 | 6/2005 | Schmidt et al. | |
| 2005/0155438 A1 | 7/2005 | Belgardt | |
| 2005/0180882 A1 | 8/2005 | Tung et al. | |
| 2005/0206895 A1 | 9/2005 | Salmelainen | |
| 2005/0227269 A1 | 10/2005 | Lloyd, Jr. et al. | |
| 2005/0273869 A1 | 12/2005 | Court et al. | |
| 2006/0099115 A1 | 5/2006 | Sandberg | |
| 2006/0205085 A1 | 9/2006 | Handique et al. | |
| 2006/0210968 A1 | 9/2006 | Goodridge | |
| 2006/0257991 A1 | 11/2006 | McDevitt et al. | |
| 2007/0003950 A1 | 1/2007 | Shen et al. | |
| 2007/0072174 A1 | 3/2007 | Sayler et al. | |
| 2007/0178450 A1 | 8/2007 | Wheeler et al. | |
| 2007/0263049 A1 | 11/2007 | Preckel et al. | |
| 2007/0292397 A1 | 12/2007 | McNulty et al. | |
| 2008/0003564 A1 | 1/2008 | Chen et al. | |
| 2008/0153096 A1 | 6/2008 | Witty et al. | |
| 2008/0193946 A1 | 8/2008 | McMillan | |
| 2008/0241819 A1 | 10/2008 | Smith | |
| 2008/0261294 A1 | 10/2008 | Noda et al. | |
| 2008/0272283 A1 | 11/2008 | Feldsine et al. | |
| 2008/0286757 A1 | 11/2008 | Gaisford et al. | |
| 2009/0155768 A1 | 6/2009 | Scholl et al. | |
| 2009/0155838 A1 | 6/2009 | Hale | |
| 2010/0028916 A1 | 2/2010 | Ambar et al. | |
| 2010/0055669 A1 | 3/2010 | Luque et al. | |
| 2010/0112549 A1 | 5/2010 | Rey et al. | |
| 2010/0133200 A1 | 6/2010 | Gin et al. | |
| 2010/0157303 A1 | 6/2010 | Ono | |
| 2010/0196877 A1 | 8/2010 | Smith et al. | |
| 2010/0225920 A1 | 9/2010 | Xia et al. | |
| 2011/0033847 A1 | 2/2011 | Walsh et al. | |
| 2011/0076672 A1 | 3/2011 | Schofield | |
| 2011/0097702 A1 | 4/2011 | Voorhees | |
| 2011/0117025 A1 | 5/2011 | Dacosta et al. | |
| 2011/0183314 A1 | 7/2011 | Smith | |
| 2011/0236960 A1 | 9/2011 | Bird et al. | |
| 2012/0003630 A1 | 1/2012 | Collins et al. | |
| 2012/0071342 A1 | 3/2012 | Lochhead et al. | |
| 2012/0134975 A1 | 5/2012 | Hyde et al. | |
| 2012/0143024 A1 | 6/2012 | Phillips et al. | |
| 2012/0225423 A1 | 9/2012 | Schwoebel et al. | |
| 2012/0252699 A1 | 10/2012 | Jaffrey et al. | |
| 2012/0288866 A1 | 11/2012 | Kozma et al. | |
| 2012/0288897 A1 | 11/2012 | Ching et al. | |
| 2012/0328576 A1 | 12/2012 | Jayasheela et al. | |
| 2013/0122549 A1 | 5/2013 | Lu et al. | |
| 2014/0134656 A1 | 5/2014 | Dortet et al. | |
| 2014/0272928 A1 | 9/2014 | Rey et al. | |
| 2015/0104787 A1 | 4/2015 | Rey et al. | |
| 2015/0132795 A1 | 5/2015 | Griswold et al. | |
| 2015/0218613 A1 | 8/2015 | de Forest et al. | |
| 2016/0281179 A1 | 9/2016 | Rey et al. | |

(56) References Cited

U.S. PATENT DOCUMENTS

2016/0281180 A1 9/2016 Rey et al.
2017/0152576 A1 6/2017 Rey et al.
2017/0233783 A1 8/2017 de Forest et al.

FOREIGN PATENT DOCUMENTS

| EP | 0274527 | | 7/1987 | | |
|---|---|---|---|---|---|
| EP | 0168933 | | 4/1993 | | |
| EP | 1213055 | A1 | 6/2002 | | |
| JP | 07083831 | | 3/1995 | | |
| JP | 2001337039 | | 12/2001 | | |
| JP | 2010107418 | | 5/2010 | | |
| WO | WO 1987/006706 | | 11/1987 | | |
| WO | WO 1994/025572 | | 11/1994 | | |
| WO | WO 1995/007457 | | 3/1995 | | |
| WO | WO 2001/028683 | | 4/2001 | | |
| WO | WO 2002/081679 | | 10/2002 | | |
| WO | WO 2002/090995 | | 11/2002 | | |
| WO | WO 2005/085855 | | 9/2005 | | |
| WO | WO 2006/075996 | | 7/2006 | | |
| WO | WO 2007/115378 | | 10/2007 | | |
| WO | WO 2010/096584 | | 8/2010 | | |
| WO | WO 2013/049121 | | 4/2013 | | |
| WO | WO 2013/173524 | | 11/2013 | | |
| WO | WO 2013/192396 | | 12/2013 | | |
| WO | WO 2014/160418 | | 10/2014 | | |
| WO | WO 2014/164768 | | 10/2014 | | |
| WO | WO2014160418 | A2 * | 10/2014 | ......... | B01L 3/50825 |

OTHER PUBLICATIONS

Office Action for U.S. Appl. No. 14/611,902, dated Mar. 30, 2015, 12 pages.
International Search Report and Written Opinion for International Application No. PCT/US2015/027519, dated Sep. 11, 2015, 17 pages.
European Search Report for European Application No. 14779477.0, dated Jun. 27, 2016.
Extended European Search Report for European Application No. 14779477.0, dated Aug. 17, 2010.
Dual-Glo Luciferase Assay System, Instructions for Use of Products E2920, E2940 and E2980, Technical Manual, Promega, 2011, 27 pages.
Hakamata, T. et al. (eds.), Chapter 14—Applications in Photomultiplier Tubes, Basics and Applications, Third Edition (Edition 3a), Hamamatsu Photonics K. K., 2007, 48 pages.
KeyPath MRSA/MSSA Blood Culture Test—BT, 510(k) Summary, MicroPhage, Inc., Apr. 29, 2011, 15 pages.
Lampinen, J. et al., Comparison of flash and glow ATP assays with thermo scientific varioskan flash luminometry,: Application Note: AP-MIB-VARIO12-0108, Thermo Scientific, 2008, 6 pages.
Luciferase Measurements using the Clarity Luminescence Microplate Reader. Luminescence made easy. Application Note, BioTek Instruments, Inc., 2006, 5 pages.
NucliSENS EasyQ MRSA Assay, 510(k) Summary, bioMerieux, Inc., Sep. 20, 2010, 23 pages.
Ulitzur, S. et al., "Introduction of lux genes into bacteria: a new approach for specific determination of bacteria and their antibiotic susceptibility," In: Schlomerich J. et al. (eds.), Bioluminescence and Chemiluminescence New Perspectives, Chichester: John Wiley and Sons (1987), pp. 463-472.
Vandercam, B. et al., "Amplification-based DNA analysis in the diagnosis of prosthetic joint infection," Journal of Molecular Diagnostics, 10(6):537-543 (2008).
Watanabe, T. et al., "Studies on luciferase from photobacterium phosphoreum," Journal of Biochemistry, 72(3):647-653 (1972).
International Search Report and Written Opinion for International Application No. PCT/EP2016/073747, dated Feb. 15, 2017, 17 pages.
Office Action received for Japanese Patent Application No. 2016-501231.
European Office Action dated Jan. 29, 2019 in Application No. 16781083.7, 4 pages.

* cited by examiner

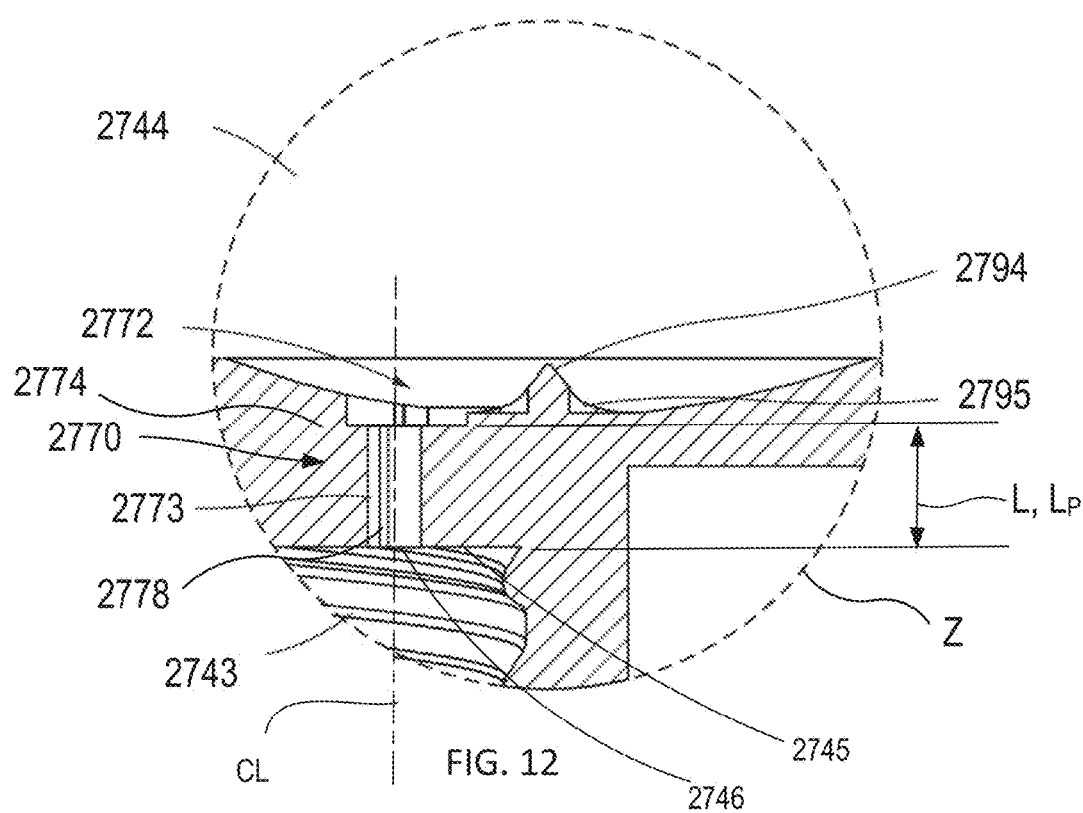
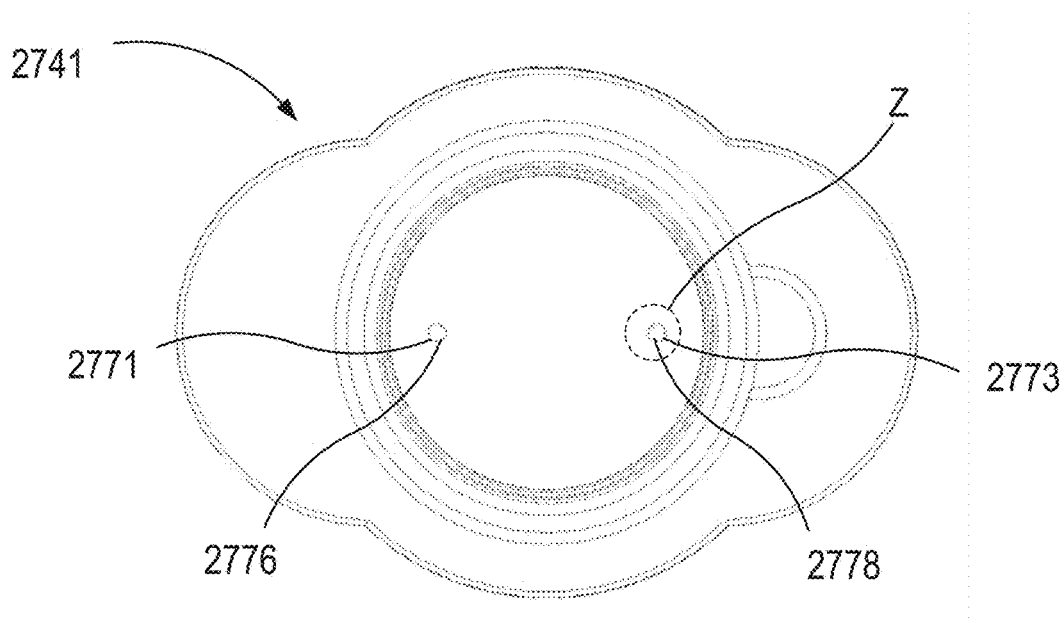
FIG. 13

2015 TEST: Stepper motor encoder data for 0.030 fluted module

REAGENT CARTRIDGE FOR DETECTION OF CELLS

CROSS-REFERENCE TO RELATED APPLICATIONS

This application claims benefit of priority to U.S. Provisional Application Ser. No. 62/237,177, entitled "Reagent Cartridge for Detection of Cells," filed Oct. 5, 2015, the disclosure of which is incorporated herein by reference in its entirety.

BACKGROUND

The embodiments described herein relate to systems and methods for detection of cells using engineered transduction particles. More particularly, the embodiments described herein also relate to a container and instrument within which the detection of bacteria can be performed in an integrated, closed system with walkaway functionality.

Detection of bacteria, especially drug resistant strains, is a critical step in diagnosing and limiting spread of bacterial infections. For example, MRSA is a drug-resistant version of the common *Staphylococcus aureus* bacteria that is carried by a significant portion of the population in the U.S. Most infections of MRSA occur in hospitals, and can have a high mortality rate (data from 2010 showed that MRSA infections kill approximately 19,000 people in the U.S. every year). Accordingly, there is a need for efficient, accurate and rapid identification of the bacterial strains (including their phenotype and/or genotype and other molecular targets) that cause infection, such as MRSA. Particularly important is the ability to identify the bacterial phenotype and/or genotype and other molecular targets from a variety of different samples (e.g., human samples, environmental samples, plant samples, veterinary samples, food samples or the like), so that the appropriate treatment and control regimen can be started in a timely fashion.

One known method for identifying bacteria includes bacterial culture. Culturing is highly sensitive, but often takes 18 hours or more to yield a result, and is therefore not suitable for rapid diagnosis or for efficient screening purposes. Known culturing methods are often performed using systems that require highly trained personnel to perform the assay, and are therefore not suitable for use in a variety of different settings. Known culturing methods are also prone to contamination, which can result in false positives and/or misidentification of the bacteria. Moreover, known culturing methods employ specifically tailored culture protocols for identification of various bacterial species, thus testing a broad bacteria panel can rapidly elevate the cost.

Direct bacterial immunodetection, that is, detection using an antibody antigen reaction, is another method for bacterial detection. Known methods of immunodetection can produce results more quickly and at a lower cost than a culture, but are often limited by the availability of selective antibodies for the bacterial strain of interest and available antibodies are prone to cross-reactivity. Such known methods are also less sensitive than culturing, so there is often nevertheless a requirement of bacterial amplification that can lengthen the assay time.

Other known methods for detection of bacterial cells include isolation and analysis of nucleic acid such as DNA or RNA. Known methods for isolating nucleic acids from a sample often include several stringent sample preparation steps that require expensive and specialized equipment. In particular, such steps include 1) removing the proteins within a sample containing bacteria or cells by adding a protease; 2) breaking down the remaining bulk sample to expose the nucleic acids contained therein (also referred to as cell lysing); 3) precipitating the nucleic acid from the sample; 4) washing and/or otherwise preparing the nucleic acid for further analysis; 5) analyzing the nucleic acid to identify the species. After preparing the sample, known analysis methods can include polymerase chain reaction (PCR), gene sequencing, gene fingerprinting, fluorescence, immunoassay, electrochemical immunoassay, microarrays, any other suitable technique or a combination thereof. PCR has found widespread commercial usage but often requires multiple steps involving expensive reagents and instrumentation. Many known methods involving PCR are not suitable for bench top testing (e.g., they require relatively skilled personnel). Moreover, known PCR methods employ thermal cycling and/or elevated temperatures, which can increase the cost, time and/or complexity of the analysis. In addition, because nucleic acid amplification based techniques do not measure the response of a bacteria to an antibiotic, such techniques are not suitable for antibiotic susceptibility testing. Finally, because nucleic acid amplification methods lyse the sample cells, such methods cannot distinguish between live and dead cells.

Some known systems and methods for cell identification include the use of bacteriophages to identify and/or detect certain bacteria. In some known methods, phages that are tagged with a reporter molecule can be used to target and infect a specific bacterial strain. After infection, the phages can undergo a lytic cycle (i.e., break the cell wall killing the target bacteria) and/or a lysogenic cycle (i.e., replication of the phage along with the bacteria without killing the bacteria), followed by detection of the amplified progeny phage. Such known methods relying on phage detection often include limiting or complex steps. For example, some known phage detection-based methods for identification rely on phage replication (during which the bacteria can be lysed), and typically require cell culturing for facilitating this process. Some known phage detection-based methods require removal or "unbinding" of specifically bound phages from the samples using carefully metered and/or pH controlled reagents. Moreover, some known phage detection-based methods rely on careful metering of the amount of phage added and/or include opening or closing of the reaction chamber to add/remove reagents, which can lead to contamination and/or premature mixing of reagents leading to erroneous results and making the assay complex in nature.

Some known phage based systems and methods can result in undesirable and/or inconsistent delivery of reagents into a closed system. For example, some known systems and methods deliver reagents into a sample to facilitate a reaction that can be optically detected. Inconsistent and/or inaccurate delivery of such reagents can result in undesirable variability associated with the light detection, potentially false readings or the like. Some known systems employ sealed reagent containers or "blister packs" to isolate the reagents and the sample until delivery of the reagents is desired. To facilitate delivery of reagents from a blister pack, some known systems include mechanisms, such as rollers, to expel the reagent. Other known systems include multiple puncturers to facilitate the rupture of a blister pack. Excessive "dead volume" (the volume within a blister pack after actuation that can contain the reagent), however, can result in inconsistent delivery times and/or amounts. Moreover, delivery mechanisms of known systems can produce undesired effects when the reagent is delivered (e.g., excessive splash or incomplete mixing). For example, if the reagent is delivered too fast, splashing or excessive wetting of a container wall can limit the effectiveness of the reagent. If the reagent is delivered too slowly, however, the mixing time may be long, thus resulting in a slower-developing reaction. Thus, many known systems do not accommodate delivery of reagents associated with a flash luminescence reaction.

In addition to the above-described drawbacks regarding the use of phage-based methods, known methods do not employ automation or instrumentation for enabling a "walk away" bacteriophage identification system. For example, many known systems do not accommodate closed system handling and/or measurement of a signal that is produced by certain reporter molecules, such as for example, a flash luminescence reaction. Thus, known systems and methods require skilled personnel and intimate handling of the samples, which can increase the possibility of false positives or negatives.

Thus, a need exists for improved apparatus and methods for rapid, cost effective and facile detection and identification of bacterial species in clinical samples. In particular, a need exists for improved rupture structures, delivery paths, and methods for delivering reagents within such systems.

SUMMARY

Systems for detecting and/or identifying target cells (e.g., bacteria) using engineered vectors (including viral vectors) and/or transduction particles are described herein. In some embodiments, an apparatus includes a housing and an actuator. The housing, which defines a reagent volume that can receive a reagent container, can be removably coupled to a reaction chamber. A delivery portion of the housing defines a delivery path between the reagent volume and the reaction chamber when the housing is coupled to the reaction chamber. The delivery path includes a protrusion such that the delivery path has a discontinuous inner surface. The actuator can be moved to convey a reagent from the reagent container into the reaction chamber via the delivery path.

In one embodiment an apparatus includes a housing configured to be removably coupled to a reaction chamber, the housing defining a reagent volume configured to contain a reagent, the housing including a side wall defining a delivery path between the reagent volume and the reaction chamber when the housing is coupled to the reaction chamber, the side wall including a protrusion within the delivery path; and an actuator configured to be manipulated to convey the reagent from the reagent volume into the reaction chamber via the delivery path. In some embodiments, the housing includes an end surface defining an exit opening through which the reagent is conveyed when the reagent exits the delivery path into the reaction chamber; and the protrusion extends into the exit opening. In some embodiments, the delivery path defines a longitudinal center line and has a path length; and the protrusion includes an edge parallel to the longitudinal center line, the edge having a protrusion length of at least ten percent of the path length. In some embodiments, the delivery path defines a longitudinal center line and has a path length; and the protrusion includes an edge parallel to the longitudinal center line, the edge having a protrusion length of at least half of the path length. In some embodiments, the protrusion length is substantially equal to the path length. In some embodiments, a flow area of the delivery path has a diameter; and the protrusion extends into the flow area a distance from the side wall, a ratio of the distance to the diameter being between about 0.1 and about 0.2. In some embodiments, a flow area of the delivery path has a diameter and a path length, a ratio of the path length to the diameter being between about 2.5 and about 3.5. In some embodiments, the side wall includes a series of protrusions within the delivery path, the series of protrusions including the protrusion. In some embodiments, the delivery path defines a longitudinal center line; and the side wall includes a series of protrusions within the delivery path, the series of protrusions including the protrusion, the series of protrusions being equally spaced circumferentially about the longitudinal center line. In some embodiments, the actuator has a plunger portion and an engagement portion, the plunger portion disposed within the reagent volume, the engagement portion of the actuator configured to receive a force to move the plunger portion within the reagent volume. In some embodiments, the apparatus further includes a reagent container disposed within the reagent volume, the reagent container containing the reagent and including a frangible portion, the housing including a puncturer within the reagent volume, the puncturer having a sharp point configured to pierce the frangible portion of the reagent container, the plunger portion of the actuator configured to contact the reagent container such that the puncturer punctures the frangible portion of the reagent container to convey the reagent from the reagent volume into the reaction chamber via the delivery path. In some embodiments, the apparatus further comprises a reagent container disposed within the reagent volume, the reagent container containing the reagent formulated to react with a plurality of reporter molecules in a sample to enhance production of a signal. In some embodiments, the reagent is a first reagent, the apparatus further comprising a reagent container disposed within the reagent volume, the reagent container containing the first reagent formulated to react with a plurality of reporter molecules in a sample to enhance production of a signal; and the reaction chamber containing a second reagent formulated to react with the sample to limit production of the signal. In some embodiments, the second reagent is formulated to sterilize the sample.

In another embodiment an apparatus is provided comprising a housing configured to be removably coupled to a reaction chamber, the housing defining a reagent volume configured to contain a reagent, the housing including delivery portion having a side wall and an end surface, the side wall defining a delivery path between the reagent volume and the reaction chamber when the housing is coupled to the reaction chamber, the end surface defining an exit opening through which an exit flow of the reagent is conveyed when exiting the delivery path; and an actuator configured to be manipulated to produce the exit flow of the reagent, the delivery portion configured such that the exit flow of the reagent forms a plume that is detached from the end surface of the delivery portion. In some embodiments, a flow area of the delivery path has a diameter; and the plume is characterized by a plume width, a ratio of the plume width to the diameter being less than about 4. In some embodiments, the side wall includes a flow structure within the delivery path, the flow structure positioned to contact the exit flow of the reagent. In some embodiments, the delivery path defines a longitudinal center line and has a path length; and the flow structure includes an edge parallel to the longitudinal center line, the edge having an edge length of at least half of the path length. In some embodiments, the side wall of the delivery portion defines a flow area along a path length within the delivery path, the delivery portion including a flow structure within the delivery path such that a shape of the flow area is discontinuous. In some embodiments, the side wall includes a series of protrusions within the delivery path, the series of protrusions being equally spaced circumferentially about a longitudinal center line of the flow path.

In another embodiment, a method includes coupling a reagent module to a sample container such that an end surface of the reagent module covers a reaction chamber defined by the sample container, the reaction chamber containing a sample, the reagent module including a housing defining a reagent volume containing a reagent, the housing including a side wall defining a delivery path between the reagent volume and the reaction chamber when the reagent module is coupled to the reaction chamber, the side wall including a protrusion within the delivery path; disposing, after the coupling, at least a distal end portion of the sample container into an instrument; and actuating the instrument to: A) produce a force on the reagent module to move at least the distal end portion of the sample container into a detection volume of the instrument, and B) manipulate, when the distal end portion of the sample container is in the detection volume, the reagent module to convey the reagent from the reagent volume into the reaction chamber via the delivery path. In some embodiments, the actuating the instrument to manipulate the reagent module includes moving an actuator within the reagent volume to produce a flow of the reagent within the delivery path, the flow forming an exit plume upon exiting the delivery path into the reaction chamber, the exit plume being detached from the end surface of the reagent module. In some embodiments, the actuating the instrument to manipulate the reagent module includes moving an actuator at a speed within the reagent volume to produce a flow of the reagent within the delivery path, the speed such that the flow of the reagent is laminar. In some embodiments, the reagent is a solution containing tridecanal; a flow area of the delivery path has a characteristic diameter; and the actuating the instrument to manipulate the reagent module includes moving an actuator at a speed within the reagent volume to produce a flow of the reagent within the delivery path, a viscosity of the solution, the characteristic diameter, and the speed being such that the flow of the reagent is laminar. In some embodiments, the actuating the instrument to manipulate the reagent module includes moving an actuator at a speed within the reagent volume to produce a flow of the reagent within the delivery path, the speed being between about 30 mm/sec and about 50 mm/sec. In some embodiments, the reagent volume includes a reagent container containing the reagent; the housing includes a puncturer within the reagent volume; and the actuating the instrument to manipulate the reagent module includes moving an actuator within the reagent volume to (1) urge a frangible portion of the reagent container into contact with the puncturer to pierce the frangible portion and (2) produce a flow of the reagent within the delivery path. In some embodiments, the delivery path defines a longitudinal center line and has a path length; and the protrusion includes an edge parallel to the longitudinal center line, the edge having a protrusion length of at least half of the path length. In some embodiments, a flow area of the delivery path has a diameter; and the protrusion extends into the flow area a distance from the side wall, a ratio of the distance to the diameter being between about 0.1 and about 0.2. In some embodiments, the delivery path defines a longitudinal center line; and the side wall includes a plurality of protrusions within the delivery path, the plurality of protrusions including the protrusion, the plurality of protrusions being equally spaced circumferentially about the longitudinal center line.

In another embodiment, a method includes coupling a reagent module to a sample container such that an end surface of the reagent module covers a reaction chamber defined by the sample container, the reaction chamber containing a sample, the reagent module including a housing defining a reagent volume containing a reagent, the housing including a side wall defining a delivery path between the reagent volume and the reaction chamber when the reagent module is coupled to the reaction chamber; disposing, after the coupling, at least a distal end portion of the sample container into an instrument; and actuating the instrument to: A) produce a force on the reagent module to move at least the distal end portion of the sample container into a detection volume of the instrument, and B) manipulate, when the distal end portion of the sample container is in the detection volume, the reagent module to convey the reagent from the reagent volume into the reaction chamber via the delivery path within a time period between about 0.2 seconds and about 0.3 seconds. In some embodiments, the actuating the instrument further causes an optical detector of the instrument to receive, during the time period, a signal associated with a magnitude of light emission in the detection volume. In some embodiments, the side wall includes a protrusion within the delivery path. In some embodiments, the actuating the instrument to manipulate the reagent module includes moving an actuator at a speed within the reagent volume to produce a flow of the reagent within the delivery path, the speed being between about 30 mm/sec and about 50 mm/sec. In some embodiments, the actuating the instrument to manipulate the reagent module includes moving an actuator within the reagent volume to produce a flow rate of the reagent within the delivery path, the flow rate being between about 1.1 ml/sec and about 1.5 ml/sec.

BRIEF DESCRIPTION OF THE DRAWINGS

FIG. 12 is an enlarged view of the portion of the housing identified as region Z in FIG. 11.

FIG. 13 is a bottom view of a housing of the container assembly shown in FIGS. 7 and 8.

DETAILED DESCRIPTION

Figure 1:
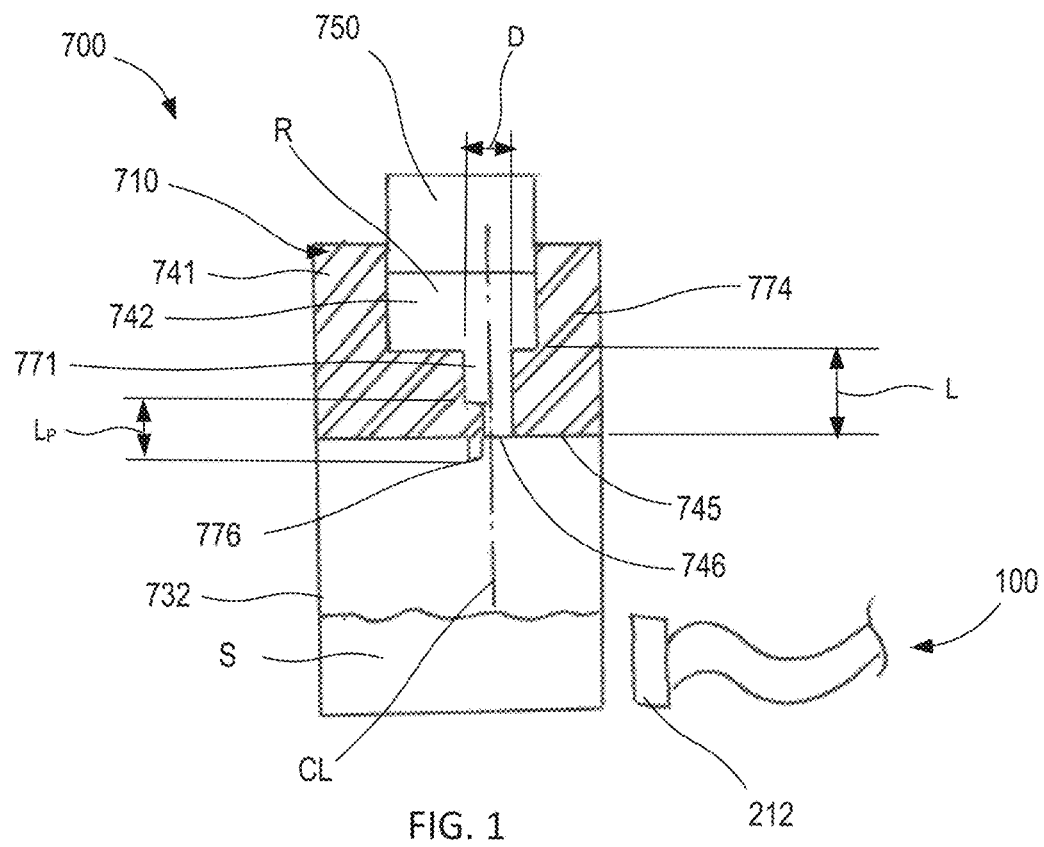
FIGS. 1 and 2 are schematic illustrations of a container assembly according to an embodiment, in a first configuration and a second configuration, respectively.

Systems and methods for detecting and/or identifying target cells (e.g., bacteria) using engineered vectors (including viral vectors) and/or transduction particles are described herein. In some embodiments, an apparatus includes a housing and an actuator. The housing, which defines a reagent volume that can receive a reagent container, can be removably coupled to a reaction chamber. A delivery portion of the housing defines a delivery path between the reagent volume and the reaction chamber when the housing is coupled to the reaction chamber. The delivery path includes a protrusion such that the delivery path has a discontinuous inner surface. The actuator can be moved to convey a reagent from the reagent container into the reaction chamber via the delivery path.

In some embodiments, an apparatus includes a housing and an actuator. The housing is configured to be removably coupled to a reaction chamber, and defines a reagent volume within which a reagent can be contained. The housing includes a side wall defining a delivery path between the reagent volume and the reaction chamber when the housing is coupled to the reaction chamber. The side wall including a protrusion within the delivery path. The actuator is configured to be manipulated to convey the reagent from the reagent volume into the reaction chamber via the delivery path.

In some embodiments, an apparatus includes a housing and an actuator. The housing is configured to be removably coupled to a reaction chamber, and defines a reagent volume configured to contain a reagent. The housing includes delivery portion having a side wall and an end surface. The side wall defines a delivery path between the reagent volume and the reaction chamber when the housing is coupled to the reaction chamber. The end surface defining an exit opening through which an exit flow of the reagent is conveyed when exiting the delivery path. The actuator is configured to be manipulated to produce the exit flow of the reagent. The delivery portion of the housing is configured such that the exit flow of the reagent forms a plume that is detached from the end surface of the delivery portion.

Methods of delivering a reagent are described herein. In some embodiments, a method includes coupling a reagent module to a sample container such that an end surface of the reagent module covers a reaction chamber defined by the sample container. The reaction chamber contains a sample. The reagent module includes a housing defining a reagent volume containing a reagent. The housing includes a side wall defining a delivery path between the reagent volume and the reaction chamber when the reagent module is coupled to the reaction chamber. The side wall includes a protrusion within the delivery path. After the coupling, at least a distal end portion of the sample container is placed into an instrument. The instrument is then actuated to: A) produce a force on the reagent module to move at least the distal end portion of the sample container into a detection volume of the instrument; and B) manipulate, when the distal end portion of the sample container is in the detection volume, the reagent module to convey the reagent from the reagent volume into the reaction chamber via the delivery path.

In some embodiments, a method includes coupling a reagent module to a sample container such that an end surface of the reagent module covers a reaction chamber defined by the sample container. The reaction chamber contains a sample, and the reagent module includes a housing defining a reagent volume containing a reagent. The housing including a side wall defining a delivery path between the reagent volume and the reaction chamber when the reagent module is coupled to the reaction chamber. At least a distal end portion of the sample container is disposed, after the coupling, into an instrument. The instrument is then actuated to: A) produce a force on the reagent module to move at least the distal end portion of the sample container into a detection volume of the instrument, and B) manipulate, when the distal end portion of the sample container is in the detection volume, the reagent module to convey the reagent from the reagent volume into the reaction chamber via the delivery path within a time period between about 0.2 seconds and about 0.3 seconds. In some embodiments, the actuating the instrument further causes an optical detector of the instrument to receive, during the time period, a signal associated with a magnitude of light emission in the detection volume. In some embodiments, the side wall includes a protrusion within the delivery path. In some embodiments, the actuating the instrument to manipulate the reagent module includes moving an actuator at a speed within the reagent volume to produce a flow of the reagent within the delivery path, the speed being between about 30 mm/sec and about 50 mm/sec. In some embodiments, the actuating the instrument to manipulate the reagent module includes moving an actuator within the reagent volume to produce a flow rate of the reagent within the delivery path, the flow rate being between about 1.1 ml/sec and about 1.5 ml/sec.

As described herein, the terms "gene," "DNA" and "nucleotide" mean the whole or a portion of the genetic sequence of the target bacteria or the vector.

As described herein, the term "plasmid" means the engineered gene, sequence and/or molecule contained within the vector that includes regulatory elements, nucleic acid sequences homologous to target genes, and various reporter constructs for causing the expression of reporter molecules within a viable cell and/or when an intracellular molecule is present within a target cell.

A "transduction particle" refers to a virus capable of delivering a non-viral nucleic acid molecule into a cell. The virus can be a bacteriophage, adenovirus, etc. A "non-replicative transduction particle" refers to a virus capable of delivering a non-viral nucleic acid molecule into a cell, but does not package its own replicated viral genome into the transduction particle. The virus can be a bacteriophage, adenovirus, etc.

As used herein, "reporter nucleic acid molecule" refers to a nucleotide sequence comprising a DNA or RNA molecule. The reporter nucleic acid molecule can be naturally occurring or an artificial or synthetic molecule. In some embodiments, the reporter nucleic acid molecule is exogenous to a host cell and can be introduced into a host cell as part of an exogenous nucleic acid molecule, such as a plasmid or vector. In certain embodiments, the reporter nucleic acid molecule can be complementary to a target gene in a cell. In other embodiments, the reporter nucleic acid molecule comprises a reporter gene encoding a reporter molecule (e.g., reporter enzyme, protein). In some embodiments, the reporter nucleic acid molecule is referred to as a "reporter construct" or "nucleic acid reporter construct."

As used herein, a "reporter molecule" or "reporter" refers to a molecule (e.g., nucleic acid or protein) that confers onto an organism a detectable or selectable phenotype. The detectable phenotype can be colorimetric, fluorescent or luminescent, for example. Reporter molecules can be expressed from reporter genes encoding enzymes mediating luminescence reactions (luxA, luxB, luxAB, luc, ruc, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3X-FLAG), and genes encoding selectable markers (ampC, tet(M), CAT, erm). The reporter molecule can be used as a marker for successful uptake of a nucleic acid molecule or exogenous sequence (plasmid) into a cell. The reporter molecule can also be used to indicate the presence of a target gene, target nucleic acid molecule, target intracellular molecule, or a cell, as described herein. Alternatively, the reporter molecule can be the reporter nucleic acid molecule itself, such as an aptamer or ribozyme.

In some embodiments, the reporter nucleic acid molecule is operatively linked to a promoter. In other aspects, the promoter can be chosen or designed to contribute to the reactivity and cross-reactivity of the reporter system based on the activity of the promoter in specific cells (e.g., specific species) and not in others. In certain aspects, the reporter nucleic acid molecule comprises an origin of replication. In other aspects, the choice of origin of replication can similarly contribute to reactivity and cross reactivity of the reporter system, when replication of the reporter nucleic acid molecule within the target cell contributes to or is required for reporter signal production based on the activity of the origin of replication in specific cells (e.g., specific species) and not in others. In some embodiments, the reporter nucleic acid molecule forms a replicon capable of being packaged as concatameric DNA into a progeny virus during virus replication.

As used herein, the singular forms "a," "an", and "the" include plural referents unless the context clearly dictates otherwise. Thus, for example, the term "a member" is intended to mean a single member or a combination of members, "a material" is intended to mean one or more materials, or a combination thereof.

As used herein, a term referring to multiple components or portions thereof is intended to refer to a first component or a first portion thereof, and/or a second component or a second portion thereof, unless the context clearly dictates otherwise. Thus, for example, the term "puncturers" is intended to refer to a "first puncturer" and/or a "second puncturer."

As used herein, the terms "about" and "approximately" generally mean plus or minus 10% of the value stated. For example, about 0.5 would include 0.45 and 0.55, about 10 would include 9 to 11, about 1000 would include 900 to 1100.

The term "fluid-tight" is understood to encompass both a hermetic seal (i.e., a seal that is gas-impervious) as well as a seal that is liquid-impervious. The term "substantially" when used in connection with "fluid-tight," "gas-impervious," and/or "liquid-impervious" is intended to convey that, while total fluid imperviousness is desirable, some minimal leakage due to manufacturing tolerances, or other practical considerations (such as, for example, the pressure applied to the seal and/or within the fluid), can occur even in a "substantially fluid-tight" seal. Thus, a "substantially fluid-tight" seal includes a seal that prevents the passage of a fluid (including gases, liquids and/or slurries) therethrough when the seal is maintained at a constant position and at fluid pressures of less than about 5 psig. Similarly, a "substantially liquid-tight" seal includes a seal that prevents the passage of a liquid (e.g., a liquid sample or reagent) therethrough when the seal is maintained at a constant position and is exposed to liquid pressures of less than about 5 psig.

In some embodiments, a container assembly can be configured to deliver a reagent formulated to enhance, catalyze or trigger the production of a light signal (e.g., a substrate of the types shown and described herein) into a reaction chamber in a manner that enhances the measurement of the light signal. For example, in some embodiments, a method of detecting the reporter molecules includes detecting the intensity (or strength) of a luminescence reaction triggered by the addition of a substrate into the sample in which reporter molecules have been expressed. More particularly, in some embodiments, the expressed reporter molecules and the substrate are collectively formulated to produce a flash reaction in response to the addition of the substrate to the sample. Flash reactions are luminescence reactions in which a distinct peak intensity occurs very quickly after the addition of the substrate (e.g., substantially instantaneously, within several seconds and/or less than one minute). Although flash reactions can produce very sensitive results (which are beneficial for detection of small quantities, etc.), the accurate and repeatable measurement of such transient reactions can be challenging.

In some embodiments, a container assembly can be configured to deliver a reagent (also referred to as a substrate) into a reaction chamber in a manner that enhances the measurement of the light signal. More particularly, in some embodiments, a container assembly can be configured to deliver a substrate in a manner that allows the substrate to sufficiently mix with the sample, while also minimizing aeration of the sample, the production of bubbles, excessive splashing, or the like, all of which can be detrimental to the optical detection to be completed simultaneously or within seconds after delivering the substrate. For example, in some embodiments, a container assembly can define a fluidic pathway that includes a protrusion (also referred to herein as an elongated protrusion, a vane, or a flow member) disposed substantially parallel to a longitudinal axis of the fluidic pathway. This arrangement allows delivery of a reagent and/or a substrate to a sample with reduced attachment of the reagent and/or substrate to a sidewall of a reaction chamber. In other words, the elongated protrusion causes the flow of reagent and/or substrate to be directed toward the sample for a more consistently repeatable reaction, even at low signal levels.

Moreover, the elongated protrusion controls the spray of the reagent and/or the substrate so that even if there are a small number of reporter molecules in the sample, the reagent and/or the substrate will mix with the sample quickly enough that a detectable flash reaction occurs. Additionally, the elongated protrusion controls the behavior of the spray of the reagent and/or the substrate so that the aeration of the sample, production of bubbles, and splashing are minimized and do not disrupt the detection of the flash reaction. Minimizing aeration can enable mixing of the reagent with the sample and increase the quality of the signal that is detected by a detector. For example, in some embodiments, a container assembly can be used in conjunction with a reporter system and reagent (e.g., substrate) that are collectively formulated to produce a flash reaction in response to the addition of the substrate to the sample within which reporter molecules have been expressed. In such embodiments, the arrangement of a delivery portion of the container assembly can allow the substrate to sufficiently mix with the sample, while also minimizing aeration of the sample, the production of bubbles, excessive splashing, or the like, all of which can be detrimental to the optical detection to be completed simultaneously or a short time period (e.g., within seconds) after delivering the substrate. In other embodiments, a container assembly can define a fluidic pathway that has a curved, arced and/or helical shape. In yet other embodiments, a container assembly can define a fluidic pathway that includes grooves, ribs, slots, or any other flow-adjusting features, to maximize mixing and/or minimize aeration.

Figure 2:
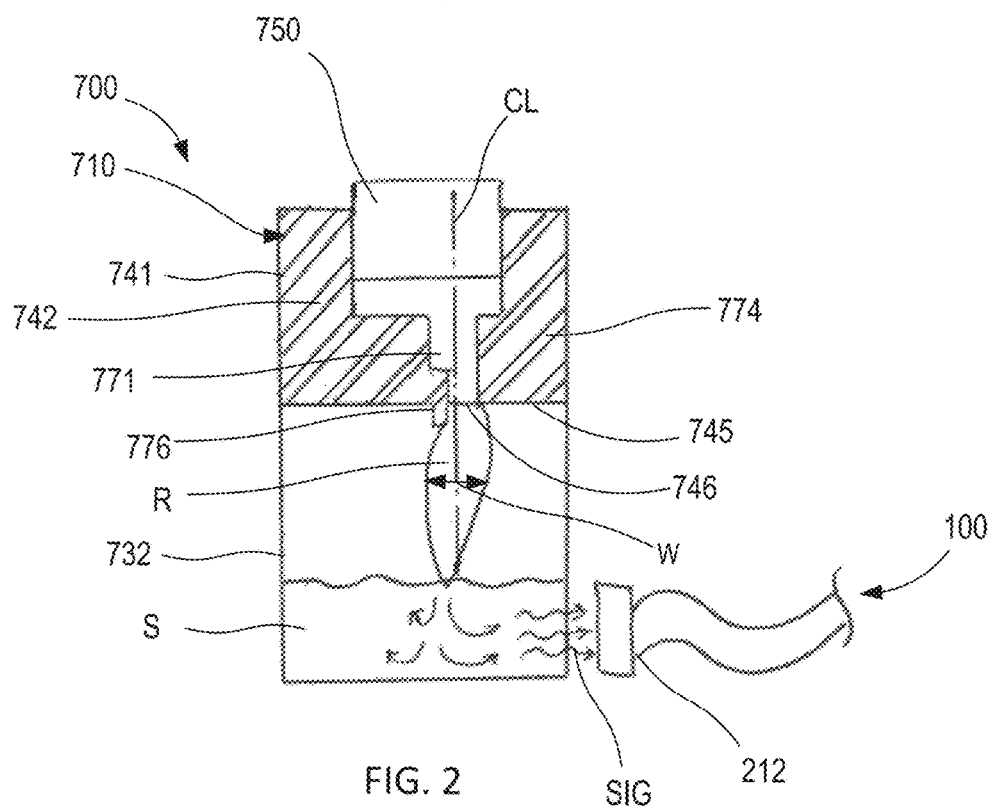

FIGS. 1 and 2 show schematic illustrations of a container assembly 700 according to an embodiment in a first configuration (FIG. 1) and a second configuration (FIG. 2). The container assembly 700 can be used with and manipulated by the instrument 100, which includes a detector 212. As described herein, the container assembly 700 and any of the container assemblies described herein can be used to detect and/or identify target cells (e.g., bacteria) within a sample according to any of the methods described herein. For example, in some embodiments, the container assembly 700 can be used to dispose and/or mix a reagent R into a sample S while maintaining fluidic isolation between the container and an outside region. In this manner, the method of cell identification can be performed in a closed system and/or a homogeneous assay. Similarly stated, in some embodiments the container assembly 700 is used in methods of cell identification and/or detection that do not involve removal of contents from the container assembly 700, separation of the contents within the container assembly 700, washing of the contents within the container assembly 700 and/or rinsing of the contents within the container assembly 700. Although shown and described as being used with or manipulated by the instrument 100, in other embodiments, the container assembly 700 and any of the container assemblies described herein can be used with or manipulated by any of the instruments and/or any of the components described in U.S. Patent Publication No. 2014/0272928, entitled "Systems and Methods for Detection of Cells using Engineered Transduction Particles" ("the '928 publication"), which is incorporated herein by reference in its entirety, and in International Patent Publication No. WO2015/164746, entitled "Reagent Cartridge and Methods for Detection of Cells," which is incorporated herein by reference in its entirety.

The container assembly 700 includes a housing 741 and an actuator 750. The housing 741, the actuator 750 and the reagent R therein are also referred to herein as a reagent module 710 (or reagent assembly). The housing 741 is removably coupled to the reaction chamber 732 that is defined by a sample container (e.g., a sample tube or the like). For example, in some embodiments, the housing 741 can be threadedly coupled to the reaction chamber 732. In other embodiments, the housing 741 and the reaction chamber 732 can form an interference fit to couple the housing 741 to the reaction chamber 732. In this manner, the reagent module 710 and the reaction chamber 732 can be stored in a decoupled configuration (e.g., as a part of a sample collection or processing kit). A test sample S can be placed into the reaction chamber 732, and the housing 741 can be coupled to the reaction chamber 732 to form the container assembly 700.

The reaction chamber 732 is configured to contain the sample S and/or other reagents, and can be formed from any suitable material, for example, glass, plastic (e.g., polypropylene), acrylic, etc. In some embodiments, the reaction chamber 732 can be formed from a lightweight, rigid and/or inert material. At least a portion of the reaction chamber 732 (e.g., the distal end portion) can be at least partially transparent to allow viewing, optical access and/or detection of the internal volume of the reaction chamber 732 by the detector 212. In some embodiments, the distal end portion of the reaction chamber 732 can be polished to promote optimal transmission of light therethrough. In some embodiments, the reaction chamber 732 can have a substantially flat side surface or bottom surface, which is aligned with the detector 212 to promote repeatable optical analysis of the sample S. Although shown as containing the sample S, in some embodiments, the reaction chamber 732 can include one or more solutions/reagents in liquid and/or dried form (e.g., bacterial nutrient solution, buffers, surfactants, transduction particle, colorants and/or antibiotics). For example, in some embodiments, the reaction chamber 732 can contain one or more transduction particles, a reagent formulated to react with one or more reporter molecules in a sample to generate and/or enhance production of a signal, a nutrient, an antibiotic, a lysis reagent, a sterilizing reagent, a colorant and/or the like.

As shown in FIGS. 1 and 2, the housing 741 defines a reagent volume 742 within which the reagent R is contained. The housing 741 includes a side wall 774 and has an end surface 745. The end surface 745 covers the reaction chamber 732 when the reagent module 710 or the housing 741 is coupled to the reaction chamber 732. Similarly stated, the end surface 745 forms a portion of a boundary of the reaction chamber 732, within which the sample S is contained. The side wall 774 defines a delivery path 771 between the reagent volume 742 and the reaction chamber 732. As described below, when the actuator 750 is manipulated, the reagent R is conveyed through the delivery path 771 and the exit opening 746 (defined by the end surface 745) into the reaction chamber 732.

The delivery path 771 defines a longitudinal center line CL, and has a length L and a size D. The delivery path 771 can have any suitable size and/or shape, and can accommodate any desired flow rate of the reagent R therethrough. For example, in some embodiments, the delivery path 771 can accommodate any suitable flow rate, e.g., 1 ml/sec, 2 ml/sec, 3 ml/sec, 4 ml/sec, 5 ml/sec. In some embodiments, a cross-sectional shape of the delivery path taken along a plane normal to the longitudinal center line CL is substantially circular, and the size D is a diameter. Similarly stated, in some embodiments, a flow area FA of the delivery path 771 has a substantially circular shape, and has a diameter D. As used herein, the "flow area" of any delivery path described herein (including the delivery path 771 or any other delivery or flow paths described herein) means the area that is bounded by a structure (e.g., a side wall) that defines the delivery path, the bounded area being within a plane that is substantially normal to the nominal flow direction of the fluid being conveyed within the delivery path. The nominal flow direction is typically parallel to a longitudinal center line defined by the delivery path. Thus, the flow area FA of a delivery path (e.g., the delivery path 771 or any of the delivery paths described herein) includes the area that is bounded by a side wall that defines the delivery path and that is within a plane that is substantially normal to a longitudinal center line defined by the delivery path. As used herein, a "substantially circular shape" means a shape that is circular about a center point for at least about 300 degrees of rotation. Thus, a substantially circular-shaped delivery path can include one or more protrusions (e.g., protrusion 776, as described below) or discontinuities that encompass about 60 degrees or less of the circumference. The ratio of the length L to the size D of the delivery path 771 can be any suitable value to produce the desired properties of the exit flow of the reagent R. For example, in some embodiments, the ratio the length L to the size D of the delivery path 771 is between about 2 and about 4. In other embodiments, the ratio the length L to the size D of the delivery path 771 is between about 2.5 and about 3.5.

The side wall 774 includes a protrusion 776 (also referred to as an elongated protrusion, a vane, a flow structure, or a flow member) within the delivery path 771. The protrusion 776 includes an inwardly projecting portion that is within and/or impacts the flow of the reagent R through the delivery path 771. The protrusion 776 can have any suitable size and/or shape to produce the desired properties of the exit flow of the reagent R. For example, the protrusion 776 can have any suitable protrusion length $L_P$. In some embodiments, the protrusion length $L_P$ can be less than the length L of the delivery path 771. For example, in some embodiments, the protrusion length $L_P$ can be at least ten percent of the length L of the delivery path 771. In other embodiments, the protrusion length $L_P$ can be at least about fifty percent of the length L of the delivery path 771. In yet other embodiments, the protrusion length $L_P$ can be the same length, or even greater than the length L of the delivery path 771. Moreover, the protrusion 776 can be at any suitable location within the delivery path 771. For example, as shown in FIG. 1, the protrusion 776 can be within, or even extend outside of, the exit opening 746. In this manner, the protrusion 776 can act as a spray or stream guide to influence the exit flow of the reagent R. For example, in some embodiments, the protrusion 776 can serve to deflect the exit flow of the reagent R away from a wall of the reaction chamber 732.

The protrusion 776 can also extend inwardly into the delivery path 771 by any suitable amount. For example, in some embodiments, the protrusion 776 can extend a distance into the delivery path such that a ratio of the distance to the size D of delivery path 771 is between about 0.1 and about 0.2 be at any suitable location within the delivery path 771. Moreover, although shown as including only a single protrusion, in other embodiments, a housing can include any suitable number of protrusions 776, such as, for example, two, three, four, or more protrusions.

The actuator 750 is coupled to the housing 741, and can be manipulated to convey the reagent R from the reagent volume 742 through the delivery path 771 and the exit opening 746, and into the reaction chamber 732. The actuator 750 can be any suitable mechanism for producing a pressure within the reagent volume 742 or otherwise producing a flow of the reagent R as described herein. For example, in some embodiments, the actuator 750 can be a plunger that is moved within the reagent volume 742 to push the reagent R through the delivery path 771. In some embodiments, the actuator 750 can produce a force to burst or pierce a seal between the reagent volume 742 and the delivery path 771. In other embodiments, the actuator 750 can be a squeeze bulb or other deformable member that, when deformed, produces a pressure within the reagent volume 742. In yet other embodiments, the actuator 750 can be a stored energy member (e.g., an electronic actuator, a magnetic member, or the like), that produces a flow of the reagent R when actuated.

The reagent volume 742 can be completely or partially filled with any suitable reagent R or substance. For example, the reagent volume 742 can contain transduction particles that include an engineered nucleic acid formulated to cause the target cell (e.g., bacteria) to produce one or more reporter molecules. In some embodiments, the reagent volume 742 can contain one or more transduction particles engineered to be incapable of replication (e.g., lytic replication, lysogenic replication). For example, in some embodiments, the reagent volume 742 can contain any of the transduction particles described herein and in International Patent Publication No. WO2014/160418 (appl. no. PCT/US 2014/026536), entitled "Non-Replicative Transduction Particles and Transduction Particle-Based Reporter Systems," filed Mar. 13, 2014 or International Patent Application Publication No. WO2015/164746, entitled "Reagent Cartridge and Methods for Detection of Cells," filed Apr. 24, 2015, each of which is incorporated herein by reference in its entirety.

In some embodiments, the reagent volume 742 can contain a reagent formulated to react with one or more reporter molecules to generate and/or enhance production of a signal. For another example, the reagent volume 742 can include a substrate, such as tridecanal, that can interact with a reporter molecule (e.g., luciferase), to produce a measurable signal, e.g., via a luminescence reaction. The tridecanal solution can be, for example, CAS No. 10486-19-8, which has a density of 0.835 g/mL at 25 C and a dynamic viscosity of 0.0002323 Pa-sec. For yet another example, in some embodiments, the reagent volume 742 can include a nutrient, an antibiotic (e.g., Beta-lactams, extended-spectrum beta-lactams, Aminoglycosides, Ansamycins, Carbacephem, Carbapenems, any generation of Cephalosporins, Glycopeptides, Lincosamides, Lipopeptide, Macrolides, Monobactams, Nitrofurans, Oxazolidonones, Penicillins, Polypeptides, Quinolones, Fluoroquinolones, Sulfonamides, Tetracyclines, mycobacterial antibiotics, Chloramphenicol, Mupirocin), a lysis reagent, a sterilizing reagent, a colorant and/or the like.

In use, the sample S is conveyed into the reaction chamber 732. The reagent module 710 is assembled to the reaction chamber 732, and the assembly is then placed into the instrument. Specifically, a distal portion of the reaction chamber 732 is moved into proximity of the detector 212. The actuator 750 is manipulated to produce a flow of the reagent R within the flow path 771, through the exit opening 746 and into the reaction chamber 732. The actuator 750 can be manipulated by any suitable mechanism. For example, in some embodiments, the actuator 750 can be manipulated by a portion of the instrument 100, such as, for example, a gripper, a plunger or the like. In other embodiments, the actuator 750 can be manipulated manually (e.g., by hand). As shown in FIG. 2, the flow of the reagent R into the reaction chamber 732 is a plume (also referred to as a stream or jet). As the contents of the reagent volume 742 are delivered through the delivery path 771, the protrusion 776 controls the behavior of the reagent plume such that it exits the delivery path 771 in a controlled and/or repeatable manner. In other words, the spray geometry can be influenced by any of the protrusion 776, the properties of the reagent, or the flow path through which the reagent R travels. An uncontrolled spray of the contents may result in the contents attaching to the walls of the reaction chamber 732, causing at least a portion of the contents to reach the sample S gradually or not reach the sample S at all. Because a detectable flash reaction requires that the reagent R reach the sample quickly and in a controlled manner, an uncontrolled spray may cause inconsistent results and/or false negatives that a reporter molecule is present in the sample. Additionally, an uncontrolled spray of the contents can cause aeration of the sample, production of bubbles, and splashing, which can reduce visibility of the reaction or slow the reaction to levels that are not consistently detectable. That is, the signal SIG (see FIG. 2) may not be repeatable or consistent for a given level of reporter molecules within the sample S.

There are many mechanisms by which the protrusion 776 can control the flow (e.g. the plume, stream or jet) of the reagent R. For example, the protrusion 776 can direct the reagent R distally toward the sample S in the reaction chamber 732, thereby reducing attachment of the contents to the end surface 745 or the walls of the reaction chamber 732. The protrusion 776 cause the flow of reagent R to be directed toward the sample S and to control the plume or jet such that even if there are a small number of reporter molecules present in the sample S, the reagent R will mix with the sample quickly enough that a detectable signal SIG from the flash reaction will be produced. Additionally, the protrusion 776 controls the spray of the contents so that the aeration of the sample, production of bubbles, and splashing are minimized and do not disrupt the detection of the flash reaction.

In some embodiments, for example, the stream or plume of the reagent can have a maximum width W. The ratio of the maximum width W to the size D of the delivery path 771 can be any suitable value, for example, to limit impingement of the reagent R onto the walls of the reaction chamber. In some embodiments, the ratio of the maximum width W to the size D of the delivery path 771 can be less than about 2. In other embodiments, the ratio of the maximum width W to the size D of the delivery path 771 can be less than about 4.

Additionally, the reagent and/or substrate R can be conveyed at a velocity and/or flow rate to promote mixing and/or reduce turbulence. For example, a step in a luciferase reaction includes the first formation of a complex between luciferase and flavin mononucleotide. In the absence of a suitable aldehyde (i.e., the substrate R), this complex is unable to proceed in the luminescence reaction. The luciferase reaction proceeds and emits light upon the addition of the aldehyde, and ideally, it is preferable that all complexed luciferases be triggered to emit photons simultaneously. This would result in a large flux of photons being emitted in a short period of time—i.e., a flash of light (indicated by the signal SIG in FIG. 2) that can be readily detected by the detector 212. As supported by the test results presented herein, however, if the reagent and/or substrate is conveyed into the reaction chamber at a rate that is too high, the amount of light detected will decrease and/or the amount of light detected from replicates will exhibit increased variability resulting in an increase in the coefficient of variation associated with light detection. This reduction in performance is related to splashing and/or formation of bubbles in the solution that can result when the reagent and/or substrate is conveyed at a high velocity. Accordingly, the mixing of the reagent and/or substrate can be controlled to produce the desired light output performance. For example, in some embodiments, the mixing of the reagent and/or substrate includes conveying the reagent and/or substrate into the reaction chamber by moving the actuator 750 linearly at a rate of between about 63 mm per second and about 81 mm per second.

In other embodiments, the mixing of the reagent and/or substrate includes conveying the reagent and/or substrate into the reaction chamber by moving the actuator 750 linearly at a rate of between about 30 mm per second and about 50 mm per second. The slower rate can produce a laminar flow of the reagent R at the exit opening 746. A laminar flow of the reagent R can produce a more repeatable delivery of the substrate as discussed herein. It is understood that the flow characteristics (i.e., laminar vs. turbulent) for a flow within an internal channel, such as the delivery path 771 can be assessed by evaluating the Reynolds number:

$$\mathrm{Re} = \frac{\rho v D}{\mu} \quad (1)$$

Where $\rho$ is the density of the fluid, $\mu$ is the viscosity of the fluid, $v$ is the velocity of the fluid within the channel, and D is the diameter (or hydraulic diameter) of the channel (e.g., the delivery path 771). By controlling (i.e., reducing) the Reynolds number, the exit flow can be maintained as a laminar flow. Thus, in some embodiments, the size D of the delivery path 771, the kinematic viscosity of the reagent R (the kinematic viscosity being $\mu/\rho$), and the actuation speed can be such that the exit flow of the reagent R is laminar. The inclusion of the protrusion 776 can, for example, act to reduce the characteristic (or hydraulic) diameter D of the delivery path 771, thereby reducing the Reynolds number as compared to that which would be for a delivery path 771 without any protrusion 776.

In some embodiments, a housing (or reagent module) can include a seal between a reagent volume (e.g., reagent volume 742) and the delivery path (e.g., delivery path 771) to maintain the reagent R in fluidic isolation before actuation of the reagent module. For example, in some embodiments, the reagent module 710 can include a thin, breakable film between the reagent volume 742 and the delivery path 771 that ruptures when the actuator 750 is manipulated. In other embodiments, a reagent module can include a separate reagent container that includes a portion that is broken, punctured or disrupted to place the reagent therein in fluid communication with the delivery path. For example, FIGS.

Figure 4:
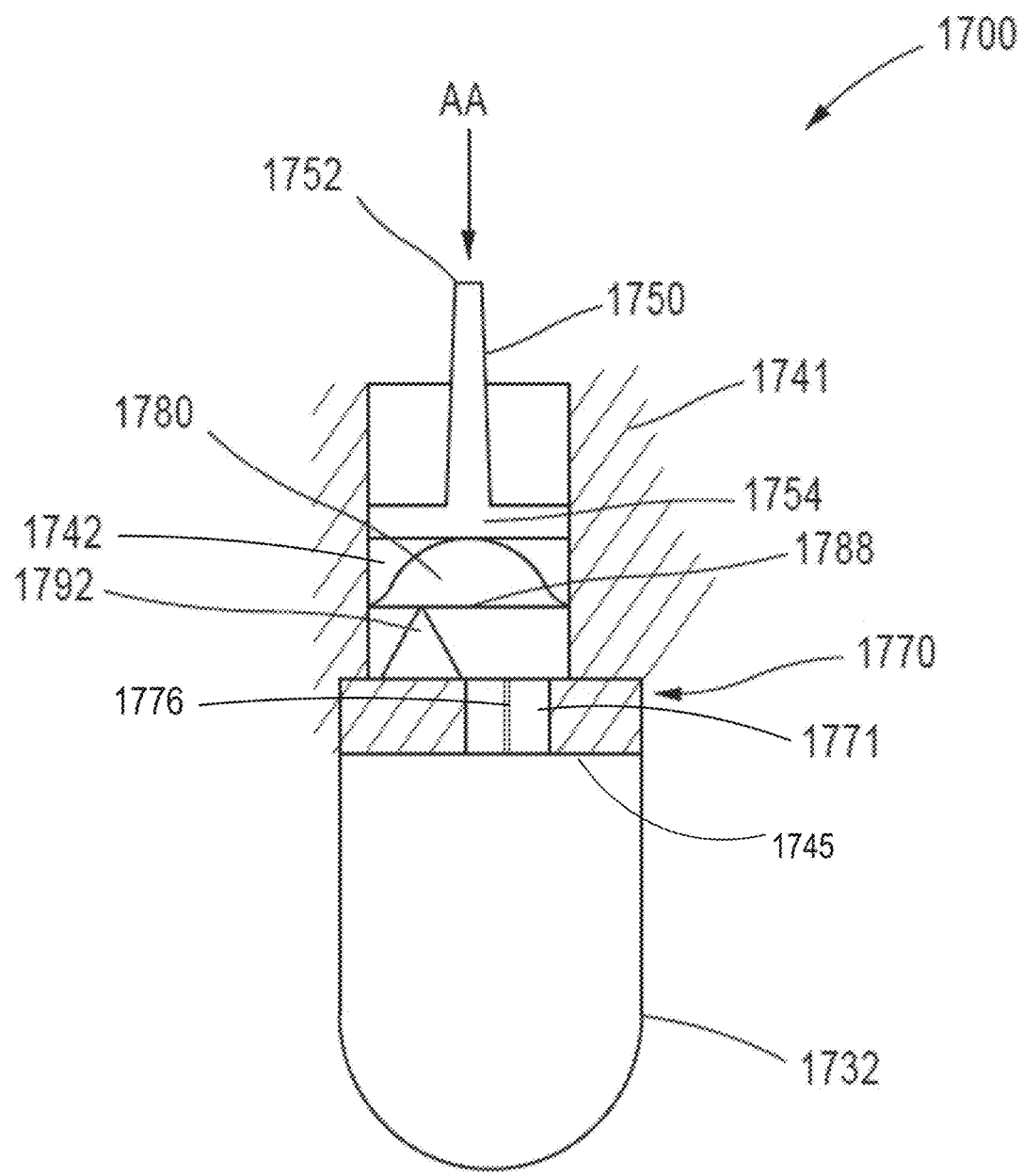
Figure 5:
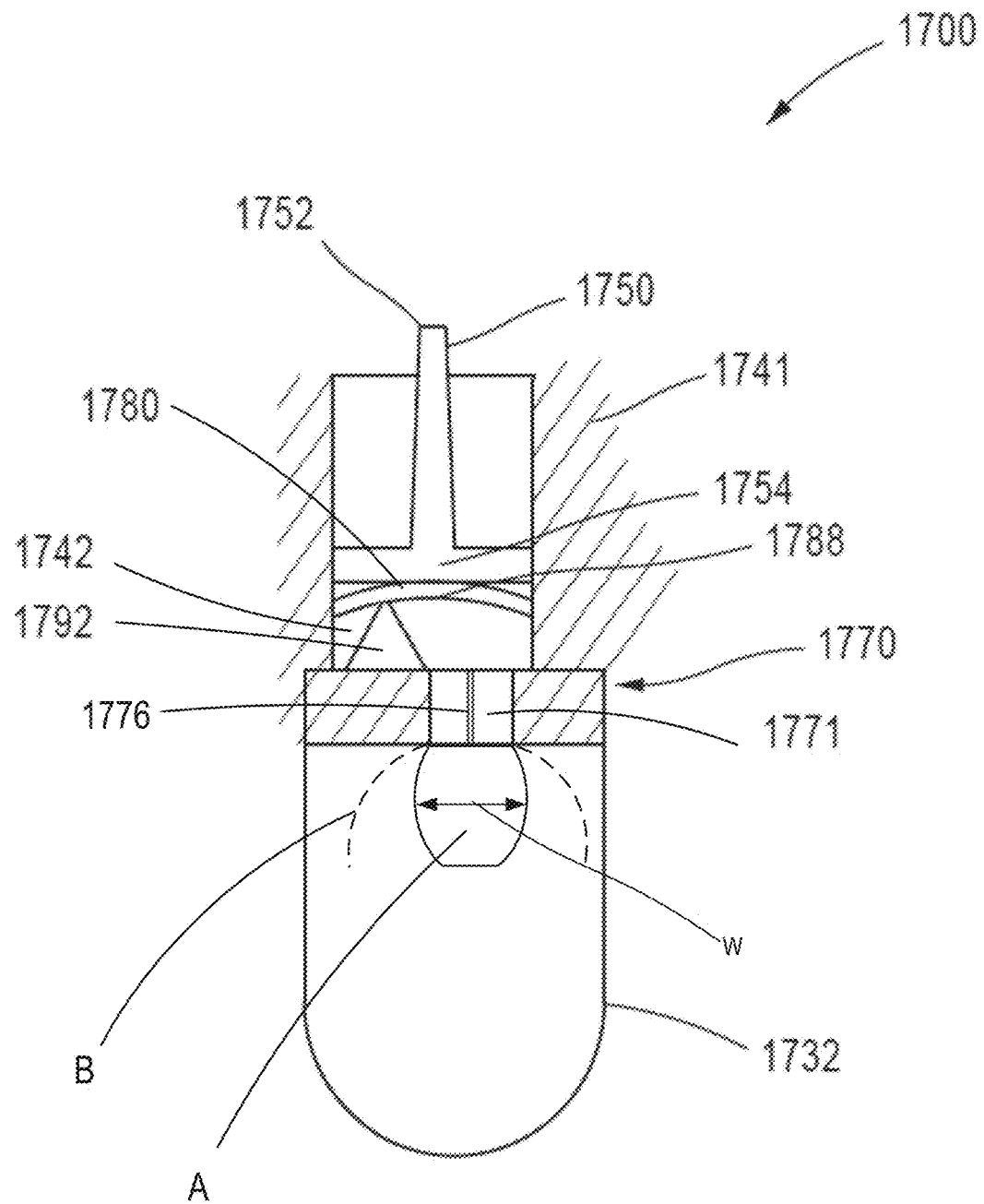

3-5 show a schematic illustration of a container assembly 1700 according to an embodiment in a first configuration (FIG. 3), a second configuration (FIG. 4), and a third configuration (FIG. 5). The container assembly 1700 can be used with and manipulated by any suitable instrument (e.g., the detection instrument 100) and/or any of the components described herein, or in U.S. Patent Publication No. 2014/0272928, entitled "Systems and Methods for Detection of Cells using Engineered Transduction Particles" ("the '928 publication"), which is incorporated herein by reference in its entirety, and in International Patent Publication No. WO2015/164746, entitled "Reagent Cartridge and Methods for Detection of Cells," which is incorporated herein by reference in its entirety. In this manner, the container assembly 1700 and any of the container assemblies described herein can be used to detect and/or identify target cells (e.g., bacteria) within a sample according to any of the methods described herein or in the '928 publication. For example, in some embodiments, the container assembly 1700 can be used to dispose and/or mix a reagent into a sample while maintaining fluidic isolation between the container and an outside region. In this manner, the method of cell identification can be performed in a closed system and/or a homogeneous assay. Similarly stated, in some embodiments the container assembly 1700 is used in methods of cell identification and/or detection that do not involve removal of contents from the container assembly 1700, separation of the contents within the container assembly 1700, washing of the contents within the container assembly 1700 and/or rinsing of the contents within the container assembly 1700.

The container assembly 1700 includes a housing 1741, an actuator 1750, and a reaction chamber 1732 that is defined by a sample container (e.g., a sample tube or the like). The housing 1751, the actuator 1750 and the reagent stored within the housing 1741 are referred to as the reagent module 1710. The housing 1741 (and/or the reagent module 1710) is removably coupled to the reaction chamber 1732. For example, in some embodiments, the housing 1741 can be threadedly coupled to the reaction chamber 1732. In other embodiments, the housing 1741 and the reaction chamber 1732 can form an interference fit to couple the housing 1741 to the reaction chamber 1732. The housing 1741 defines a reagent volume 1742 configured to receive a reagent container 1780. The housing 1741 includes a puncturer 1792 and a delivery portion 1770. In some embodiments, the housing 1741, the delivery portion 1770 and/or the puncturer 1792 can be monolithically constructed. In other embodiments, the housing 1741, the delivery portion 1770 and/or the puncturer 1792 can be formed separately and then joined together.

Figure 3:
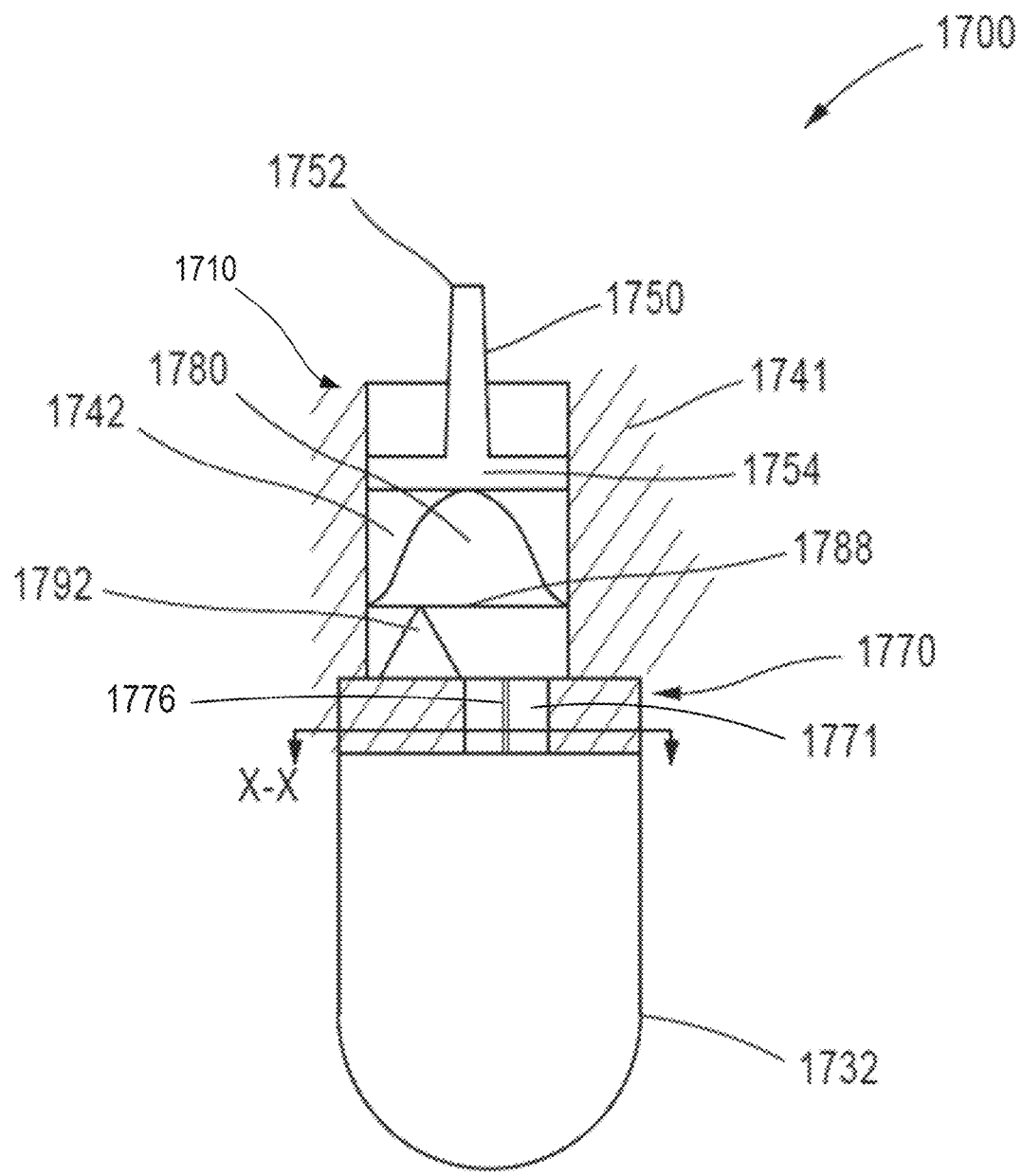
FIGS. 3-5 are schematic illustrations of a container assembly according to an embodiment, in a first configuration, second configuration, and third configuration, respectively.

The puncturer 1792 is configured to pierce (e.g., rupture) a frangible portion 1788 of the reagent container 1780 to convey a reagent from the reagent container 1780 into the reaction chamber 1732. As shown in FIG. 3, the puncturer 1792 includes a structure that terminates in a single sharp point configured to pierce the reagent container 1780. Although shown as including a single sharp point, in other embodiments, a puncturer can include a sharp edge (e.g., a linear edge) and/or series of protrusions configured to pierce the reagent container. In some embodiments, although not shown, the puncturer 1792 can include a transfer pathway in fluid communication with the reagent volume 1742. Thus, when the puncturer 1792 pierces the reagent container 1780, the transfer pathway can provide a pathway through which the contents of the reagent container 1780 can flow into the delivery portion 1770.

Figure 6:
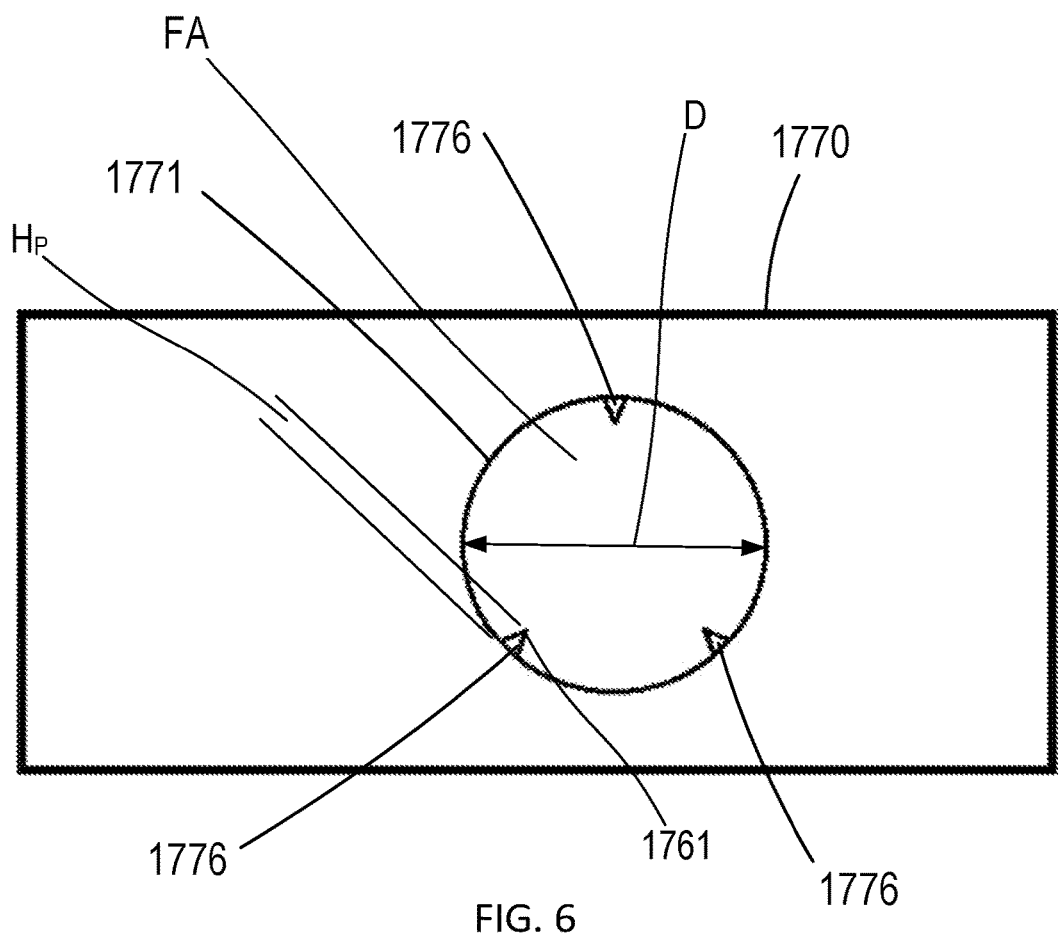
FIG. 6 is a cross-sectional view of a portion of the container assembly shown in FIGS. 3-5 taken along the line X-X in FIG. 3.

The delivery portion 1770 is configured to facilitate the delivery of the contents from the reagent container 1780 and/or the reagent volume 1742 into the reaction chamber 1732. Thus, as shown, the delivery portion 1770 can provide any suitable pathway and/or mechanism for delivering transduction particles and/or reagents disposed in the reagent container 1780 and/or reagent volume 1742 into the reaction chamber 1732. In particular, the delivery portion 1770 defines a delivery path 1771 between the reagent volume 1742 and the reaction chamber 1732. The delivery path 1771 can have any suitable size and/or shape, and can accommodate any desired flow rate therethrough. For example, in some embodiments, the delivery path 1771 can accommodate any suitable flow rate, e.g., 1 ml/sec, 2 ml/sec, 3 ml/sec, 4 ml/sec, 5 ml/sec. The delivery path has a length and a cross-sectional size. In some embodiments, a cross-sectional shape normal to a longitudinal center line is substantially circular, and the size of the delivery path 1771 is a diameter D (as shown in FIG. 6). The ratio of the length to the cross-sectional size (e.g., the diameter D) of the delivery path 1771 can be any suitable value to produce the desired properties of the exit flow of the reagent therethrough. For example, in some embodiments, the ratio the length to the size (e.g., the diameter D) of the delivery path 1771 is between about 2 and about 4. In other embodiments, the ratio the length to the size (e.g., the diameter D) of the delivery path 1771 is between about 2.5 and about 3.5.

The delivery path 1771 includes elongated protrusions 1776 (also referred to as elongated protrusions, vanes, flow structures, or flow members) that are substantially parallel with respect to a longitudinal axis of the delivery path 1771. As shown in FIG. 6, which is a cross-sectional view taken along line X-X in FIG. 3, the delivery path 1771 includes three protrusions 1776. However, the delivery path 1771 can include any suitable number of protrusions 1776, such as, for example, one protrusion, to protrusion, or four protrusions. Although shown as being disposed from a proximal end of the delivery path 1771 to a distal end of the delivery path 1771, the protrusions 1776 can be disposed such that one, some, or all of the protrusions extend only partially through the length of the delivery path 1771, such as, for example, through the distal half of the delivery path. In some embodiments, the protrusion length can be less than the total length of the delivery path 1771. For example, in some embodiments, the protrusion length can be at least ten percent of the length of the delivery path 1771. In other embodiments, the protrusion length can be at least about fifty percent of the length of the delivery path 1771. In yet other embodiments, the protrusion length can be the same length, or even greater than the length of the delivery path 1771. For example, the protrusions 1776 can be fully within, or even extend outside of, an exit opening of the housing 1741. In this manner, the protrusions 1776 can act as a spray or stream guide to influence the exit flow of the reagent.

As shown in FIG. 6, the protrusions 1776 include an inwardly projecting sharp edge 1761. The protrusions 1776 can also extend inwardly into the delivery path 1771 by any suitable amount $H_P$ (e.g., the height of the protrusions 1776). For example, in some embodiments, the protrusions 1776 can extend a distance into the delivery path such that a ratio of the height $H_P$ to the size D of delivery path 1771 is between about 0.1 and about 0.2.

The actuator 1750 has a plunger portion 1754 disposed within the reagent volume 1742 and an engagement portion 1752. The engagement portion 1752 of the actuator 1750 is configured to be manipulated to move the plunger portion 1754 within the reagent volume 1742 to deform the reagent container 1780. In this manner, movement of the plunger portion 1754 can urge the frangible portion 1788 of the reagent container 1780 against the puncturer 1792 to pierce and/or rupture the frangible portion 1788. The plunger portion 1754 of the actuator 1750 and a portion of the housing 1741 can collectively define a seal to fluidically and/or optically isolate the reagent volume 1742 from a volume outside of the housing 1741.

The reagent container 1780 can be completely or partially filled with any suitable reagent or substance. For example, the reagent container 1780 can contain transduction particles that include an engineered nucleic acid formulated to cause the target cell (e.g., bacteria) to produce one or more reporter molecules. In some embodiments, the reagent container 1780 can contain one or more transduction particles engineered to be incapable of replication (e.g., lytic replication, lysogenic replication). For example, in some embodiments, the reagent container 1780 can contain any of the transduction particles described herein and in International Patent Publication No. WO2014/160418 (appl. no. PCT/US 2014/026536), entitled "Non-Replicative Transduction Particles and Transduction Particle-Based Reporter Systems," filed Mar. 13, 2014 or International Patent Application Publication No. WO2015/164746, entitled "Reagent Cartridge and Methods for Detection of Cells," filed Apr. 24, 2015, each of which is incorporated herein by reference in its entirety.

In some embodiments, the reagent container can contain a reagent formulated to react with one or more reporter molecules to generate and/or enhance production of a signal. For another example, the reagent container 1780 can include a substrate, such as tridecanal, that can interact with a reporter molecule (e.g., luciferase), to produce a measurable signal, e.g., via a luminescence reaction. The tridecanal solution can be, for example, CAS No. 10486-19-8, which has a density of 0.835 g/mL at 25 C and a dynamic viscosity of 0.0002323 Pa-sec. For yet another example, in some embodiments, the reagent volume 742 can include a nutrient, an antibiotic (e.g., Beta-lactams, extended-spectrum beta-lactams, Aminoglycosides, Ansamycins, Carbacephem, Carbapenems, any generation of Cephalosporins, Glycopeptides, Lincosamides, Lipopeptide, Macrolides, Monobactams, Nitrofurans, Oxazolidonones, Penicillins, Polypeptides, Quinolones, Fluoroquinolones, Sulfonamides, Tetracyclines, mycobacterial antibiotics, Chloramphenicol, Mupirocin), a lysis reagent, a sterilizing reagent, a colorant and/or the like.

The reagent container 1780 can be shaped and sized to be disposed substantially inside the reagent volume 1742. The reagent container 1780 can be constructed from materials that are substantially impermeable to and/or substantially chemically inert from the substance contained therein (e.g., transduction particle, substrate, antibiotics, buffers, surfactants, or any other reagent that can be used with the detection assay) and the outside environment. At least a portion of the reagent container 1780 (e.g., the frangible portion 1788) can be constructed from a material (e.g., polymer film, such as any form of polypropylene) having certain temperature characteristics such that the desired properties and integrity are maintained over a certain temperature. For example, in some instances, it can be desirable to store the reagent container 1780 containing reagent and/or substrate in a refrigerated condition. In some embodiments, a portion of the reagent container 1780 can be constructed from bi-axially oriented polypropylene (BOP). In some embodiments, a portion of the reagent container 1780 can be constructed from aluminum. In some embodiments, a portion of the reagent container 1780 can be constructed from polyvinyl chloride (PVC), ethylene vinyl alcohol (EVOH), polyethylene (PE) and/or polychlorotrifluoroethene (PCTFE or PTFCE).

The reaction chamber 1732 is configured to contain a sample and/or other reagents, and can be formed from any suitable material, for example, glass, plastic (e.g., polypropylene), acrylic, etc. In some embodiments, the reaction chamber 1732 can be formed from a lightweight, rigid and/or inert material. At least a portion of the reaction chamber 1732 (e.g., the distal end portion) can be at least partially transparent to allow viewing, optical access and/or detection of the internal volume of the reaction chamber 1732 via a detector (e.g., the detector 212 or any other suitable detector). In some embodiments, the distal end portion of the reaction chamber 1732 can be polished to promote optimal transmission of light therethrough. Although shown as being shaped as a cylinder with a rounded bottom, in other embodiments, the reaction chamber 1732 can have any other suitable shape, e.g., square, rectangular, oval, polygonal, elliptical, conical, etc. For example, in some embodiments, the reaction chamber 1732 can have a substantially flat bottom. In some embodiments, the reaction chamber 1732 can have a diameter of 12 mm and a height of 75 mm. In some embodiments, the container assembly 1700 can be provided with one or more solutions/reagents in liquid and/or dried form (e.g., bacterial nutrient solution, buffers, surfactants, transduction particle, colorants and/or antibiotics), predisposed within the reaction chamber 1732. In some instances, the reaction chamber 1732 can contain any suitable reagent and/or substance. For example, in some embodiments, the reaction chamber 1732 can contain one or more transduction particles, a reagent formulated to react with one or more reporter molecules in a sample to generate and/or enhance production of a signal, a nutrient, an antibiotic, a lysis reagent, a sterilizing reagent, a colorant and/or the like.

As shown in FIG. 3, the container assembly 1700 is in a first configuration. In the first configuration, the actuator 1750 is positioned such that the reagent container 1780 disposed within the housing 1741 is substantially undeformed. Similarly stated, the actuator 1750 is positioned such that it does not cause puncturer 1792 to pierce the reagent container 1780. Thus, the container assembly 1700 is in a "ready" state when in the first configuration. In some embodiments, the container assembly 1700 can include a safety mechanism (not shown) to prevent and/or limit movement of the actuator 1750 relative to the housing 1741 until desired by the operator.

To actuate the container assembly 1700, a force is applied to the engagement portion 1752 of the actuator 1750, thus causing the actuator 1750 to move as shown by the arrow AA in FIG. 4. As shown in FIG. 4, the container assembly 1700 is in a second (or "intermediate") configuration. In the second configuration, the actuator 1750 is positioned such that the reagent container 1780 is partially deformed. Similarly stated, the actuator 1750 is positioned such that at least a portion of the force is transferred to the reagent container 1780. As such, at least a portion of the reagent container 1780 becomes deformed. In some instances, in the second configuration, the puncturer 1792 can at least partially pierce a portion (e.g., the frangible portion 1788) of the reagent container 1780, thereby placing the internal volume of the reagent container 1780 in fluid communication with the delivery path 1771.

As shown in FIG. 5, the container assembly 1700 is in a third (or "deployed") configuration. In the third configuration, the actuator 1750 is positioned such that the reagent container 1780 is substantially deformed. Similarly stated, the actuator 1750 is positioned such that at least a portion of the force is transferred to the reagent container 1780. In such a configuration, the puncturer 1792 has pierced the reagent container 1780 (e.g., the frangible portion 1788), such that the contents of the reagent container have substantially exited the reagent container 1780 and entered the delivery portion 1770 and the reaction chamber 1732, as indicated by controlled plume A.

In use, the actuator 1750 (e.g., the engagement portion 1752) is manipulated to move the plunger portion 1754 within the housing 1741 such that the plunger portion 1754 engages a contact portion (not identified in FIGS. 3-5) of the reagent container 1780 to partially deform the reagent container 1780 from the first configuration to the second configuration. As the plunger portion 1754 engages the contact portion of the reagent container 1780, the puncturer 1792 pierces a portion of the reagent container 1780 (e.g., a frangible portion 1788) to convey the contents (e.g., a reagent) from the reagent container 1780 into the reaction volume 1742, the delivery portion 1770, and/or the reaction chamber 1732. From the second configuration to the third configuration, the actuator 1750 is manipulated to move the plunger portion 1754 within the housing 1741 such that the plunger portion 1754 engages a contact portion of the reagent container 1780 to deform the reagent container 1780 from the second configuration to the third configuration. As the reagent container 1780 deforms from the second configuration to the third configuration, substantially all of its contents is conveyed from the reagent container 1780 into the reaction volume 1742, the delivery portion 1770, and/or the reaction chamber 1732, such that "dead volume" in the reagent container 1780 is limited. In this manner, substantially repeatable delivery of the contents from the reagent container 1780 to the reaction chamber 1732 can be obtained. For example, in some embodiments, a deformation of a first reagent container at a first time and a deformation of a second reagent container at a second time after the first time can be substantially similar, thereby allowing for substantially all of the contents to be transferred from the reagent container 1780 at the first time and the second time. Moreover, this arrangement can limit clogging or obstructions that may result from the piercing of the reagent container 1780, thus providing a more repeatable delivery of the contents of the reagent container 1780.

As the contents of the reagent container 1780 and/or the reaction volume 1742 are delivered through the delivery path 1771 of the delivery portion 1770, the protrusions 1776 control the behavior of the contents such that the contents exit the delivery path 1771 in the controlled plume A (also referred to as a stream or jet of the contents and/or reagent). In other words, the spray geometry can be influenced by any of the protrusions 1776, the properties of the reagent, or the flow path through which the reagent travels. An uncontrolled spray of the contents may result in the contents attaching to the walls of the reaction chamber 1732, causing at least a portion of the contents to reach the sample gradually or not reach the sample at all. Because a detectable flash reaction requires that the reagent reach the sample quickly and in a controlled manner, an uncontrolled spray may cause inconsistent results and/or false negatives that a reporter molecule is present in the sample. Additionally, an uncontrolled spray of the contents can cause aeration of the sample, production of bubbles, and splashing, which can reduce visibility of the reaction or slow the reaction to levels that are not consistently detectable. That is, the signal may not be repeatable or consistent for a given level of reporter molecules within the sample.

There are many mechanisms by which the protrusions 1776 can control the flow (e.g. the plume, stream or jet) of the reagent. For example, the protrusions 1776 can direct the reagent distally toward the sample in the reaction chamber 1732, thereby reducing attachment of the contents to the end surface 1745 of the housing or the walls of the reaction chamber 1732. The protrusions 1776 cause the flow of reagent to be directed toward the sample and to control the plume or jet such that even if there are a small number of reporter molecules present in the sample, the reagent will mix with the sample quickly enough that a detectable signal from the flash reaction will be produced. Additionally, the protrusions 1776 control the spray of the contents so that the aeration of the sample, production of bubbles, and splashing are minimized and do not disrupt the detection of the flash reaction.

In some embodiments, for example, the stream or plume of the reagent can have a maximum width W. The ratio of the maximum width W to the size D of the delivery path 1771 can be any suitable value, for example, to limit impingement of the reagent onto the walls of the reaction chamber 1732. In some embodiments, the ratio of the maximum width W to the size D of the delivery path 1771 can be less than about 2. In other embodiments, the ratio of the maximum width W to the size D of the delivery path 1771 can be less than about 4.

Additionally, the reagent and/or substrate can be conveyed at a velocity and/or flow rate to promote mixing and/or reduce turbulence. For example, a step in a luciferase reaction includes the first formation of a complex between luciferase and flavin mononucleotide. In the absence of a suitable aldehyde (i.e., the substrate R), this complex is unable to proceed in the luminescence reaction. The luciferase reaction proceeds and emits light upon the addition of the aldehyde, and ideally, it is preferable that all complexed luciferases be triggered to emit photons simultaneously. This would result in a large flux of photons being emitted in a short period of time—i.e., a flash of light that can be readily detected by the detector (e.g., the detector 212). As supported by the test results presented herein, however, if the reagent and/or substrate is conveyed into the reaction chamber at a rate that is too high, the amount of light detected will decrease and/or the amount of light detected from replicates will exhibit increased variability resulting in an increase in the coefficient of variation associated with light detection. This reduction in performance is related to splashing and/or formation of bubbles in the solution that can result when the reagent and/or substrate is conveyed at a high velocity. Accordingly, the mixing of the reagent and/or substrate can be controlled to produce the desired light output performance. For example, in some embodiments, the mixing of the reagent and/or substrate includes conveying the reagent and/or substrate into the reaction chamber by moving the actuator 1750 linearly at a rate of between about 63 mm per second and about 81 mm per second.

In other embodiments, the mixing of the reagent and/or substrate includes conveying the reagent and/or substrate into the reaction chamber by moving the actuator 1750 linearly at a rate of between about 30 mm per second and about 50 mm per second. The slower rate can produce a laminar flow of the reagent at the exit opening. A laminar flow of the reagent R can produce a more repeatable delivery of the substrate as discussed herein. It is understood that the flow characteristics (i.e., laminar vs. turbulent) for a flow within an internal channel, such as the delivery path 1771 can be assessed by evaluating the Reynolds number:

$$\text{Re} = \frac{\rho v D}{\mu} \quad (2)$$

Where ρ is the density of the fluid, μ is the viscosity of the fluid, v is the velocity of the fluid within the channel, and D is the diameter (or hydraulic diameter) of the channel (e.g., the delivery path 1771). By controlling (i.e., reducing) the Reynolds number, the exit flow can be maintained as a laminar flow. Thus, in some embodiments, the size D of the delivery path 1771, the kinematic viscosity of the reagent R (the kinematic viscosity being μ/ρ), and the actuation speed can be such that the exit flow of the reagent R is laminar. The inclusion of the protrusions 1776 can, for example, act to reduce the characteristic (or hydraulic) diameter D of the delivery path 1771, thereby reducing the Reynolds number as compared to that which would be for a delivery path 1771 without any protrusions.

Figure 7:
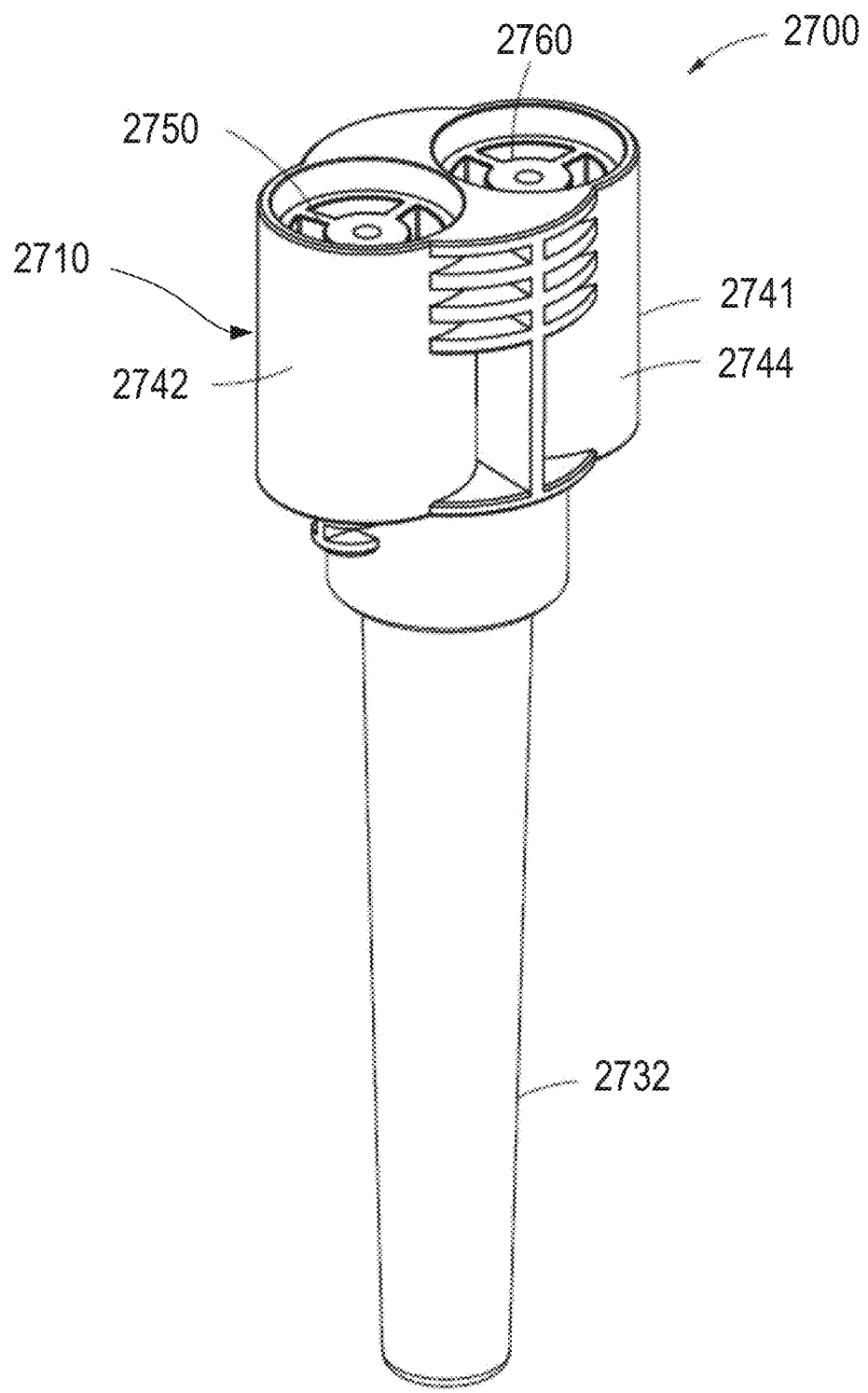
FIGS. 7 and 8 show a perspective view and an exploded view, respectively, of a container assembly, according to an embodiment.
Figure 8:
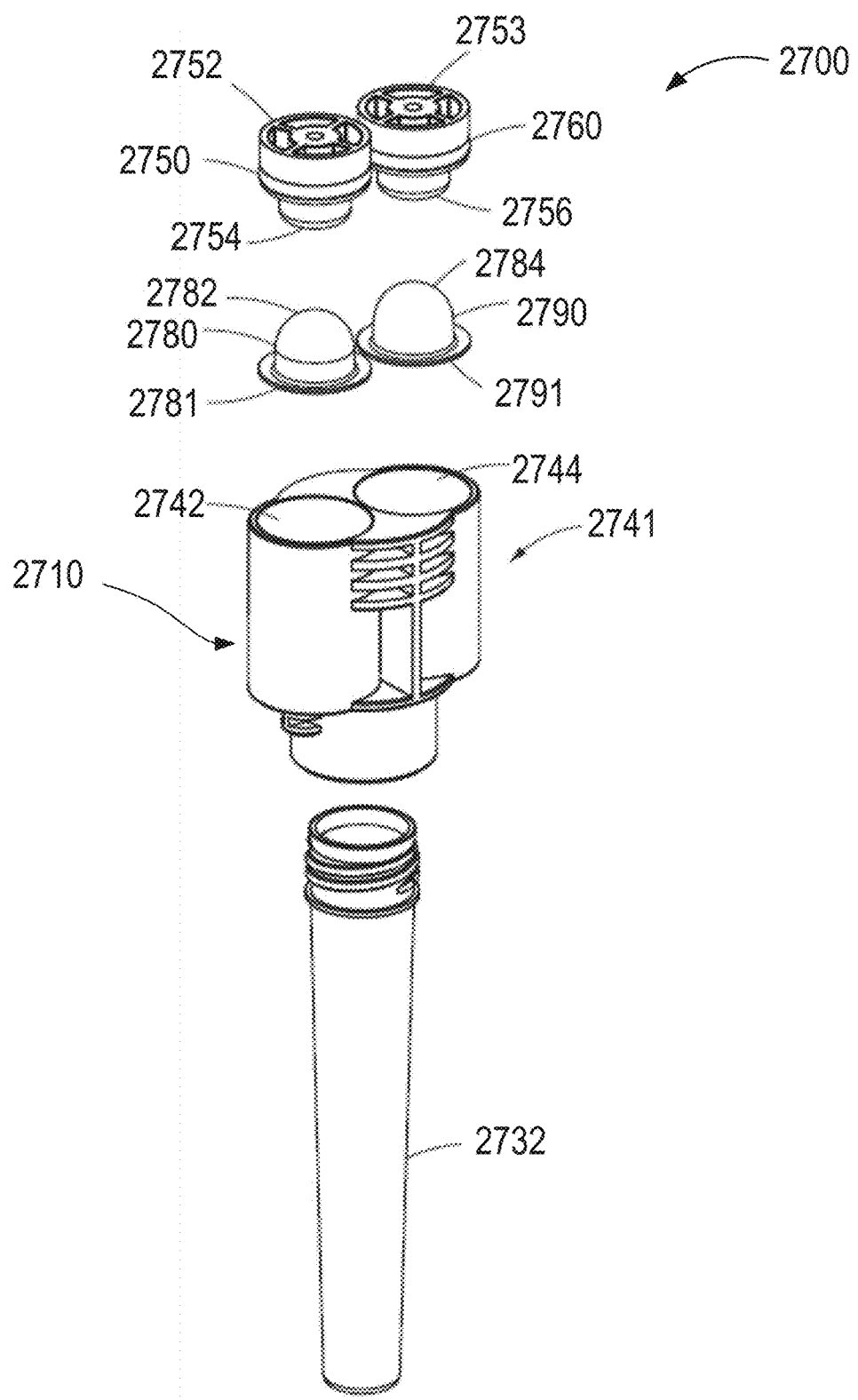
Figure 9:
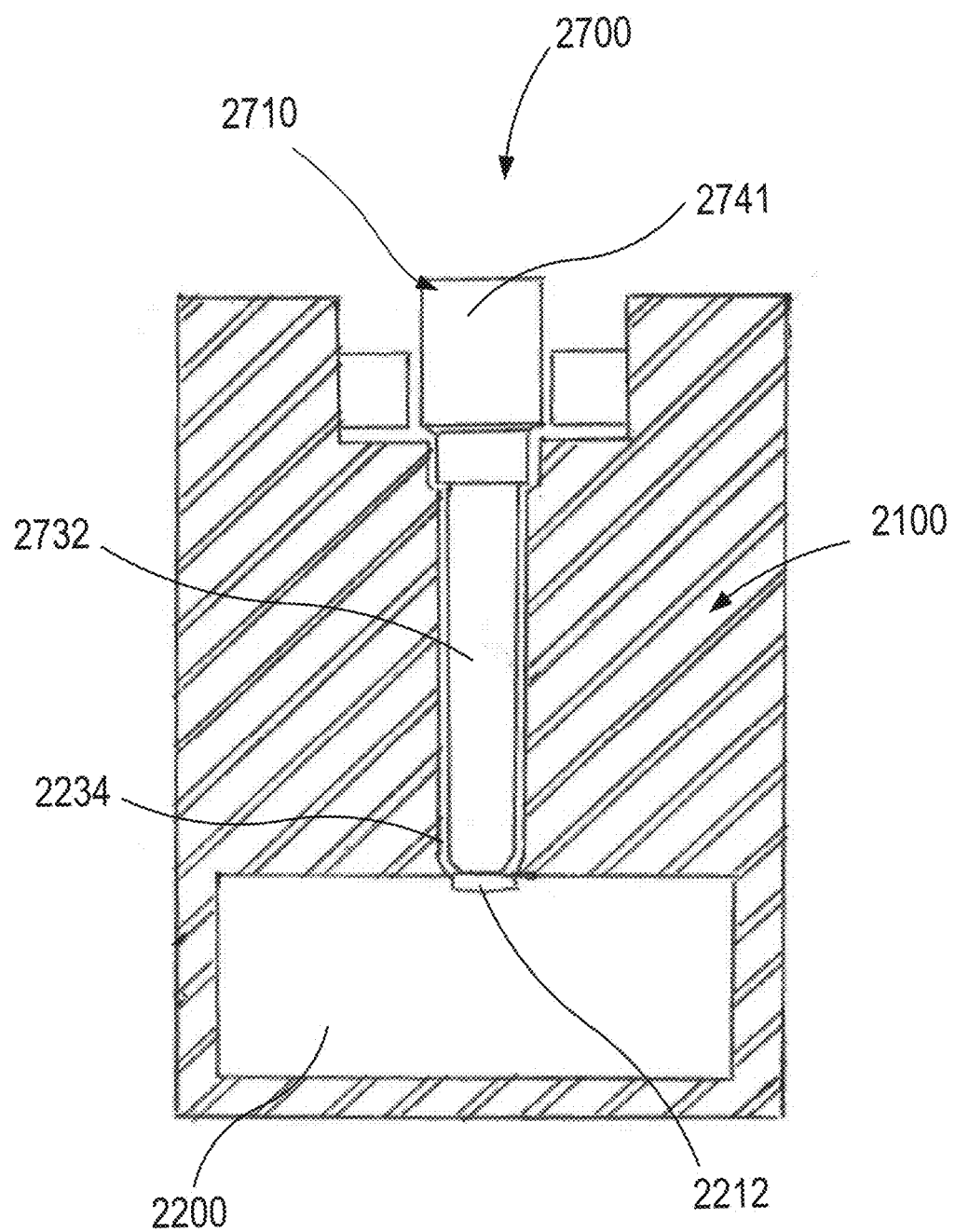
FIG. 9 is a cross-sectional view of the container assembly shown in FIGS. 7 and 8 in an instrument according to an embodiment.

FIGS. 7 and 8 show a perspective view of a container assembly 2700 and an exploded view of the container assembly 2700, respectively, according to an embodiment. The container assembly 2700 can be used with and manipulated by the instrument 2100, or any suitable instrument and/or any of the components described herein, or in U.S. Patent Publication No. 2014/0272928, entitled "Systems and Methods for Detection of Cells using Engineered Transduction Particles" ("the '928 publication"), which is incorporated herein by reference in its entirety, and in International Patent Publication No. WO2015/164746, entitled "Reagent Cartridge and Methods for Detection of Cells," which is incorporated herein by reference in its entirety. As shown in FIG. 9 and described in detail below, the container assembly 2700 can be placed into a detection volume 2234 of the instrument 2100. The detection volume 2234 can be optically coupled to a detection module 2200, which includes a detector 2212. In use, the container assembly 2700 can be actuated to add one or more reagents to the sample therein to induce a light reaction (e.g., a flash reaction) that is detected by the detection module 2200 and/or the detector 2212. Moreover, the container assembly 2700 and any of the container assemblies described herein can be used to detect and/or identify target cells (e.g., bacteria) within a sample according to any of the methods described herein or in the '928 publication. For example, in some embodiments, the container assembly 2700 can be used to dispose and/or mix a reagent into a sample while maintaining fluidic isolation between the container and an outside region. In this manner, the method of cell identification can be performed in a closed system and/or a homogeneous assay. Similarly stated, in some embodiments the container assembly 2700 is used in methods of cell identification and/or detection that do not involve removal of contents from the container assembly 2700, separation of the contents within the container assembly 2700, washing of the contents within the container assembly 2700 and/or rinsing of the contents within the container assembly 2700.

The container assembly 2700 includes a housing 2741, a first actuator 2750, a second actuator 2760, and a reaction chamber 2732 that is defined by a sample container (e.g., a sample tube or the like). The housing 2741 defines a first reagent volume 2742 configured to receive a first reagent container 2780 and a second reagent volume 2744 configured to receive a second reagent container 2790. The assembly of the housing 2741, the first actuator 2750, the first reagent container 2780, the second actuator 2760 and the second reagent container 2790 can be referred to as a cap assembly or reagent assembly (or reagent module) 2710. The housing 2741 (and/or the cap assembly) is removably coupled to the reaction chamber 2732. The reagent module 2710 and the reaction chamber 2732 can be stored in a decoupled configuration (e.g., as a part of a sample collection or processing kit). A test sample can be placed into the reaction chamber 2732, and the housing 2741 can be coupled to the reaction chamber 2732 to form the container assembly 2700. For example, as shown in FIG. 8, the housing 2741 can be threadedly coupled to a proximal portion of the reaction chamber 2732. In other embodiments, the housing 2741 and the reaction chamber 2732 can form an interference fit to couple the housing 2741 to the reaction chamber 2732. Thus, the housing 2741 (or cap assembly) can be stored separately from and/or spaced apart from the reaction chamber 2732. In this manner, a user can then dispose a sample into the reaction chamber 2732 in accordance with the methods described herein (and in the '928 publication, which is incorporated herein by reference in its entirety), and can then assemble the housing 2741 (or cap assembly) to the reaction chamber 2732 (or "tube") and complete the steps for cell identification, as described herein.

Figure 10:
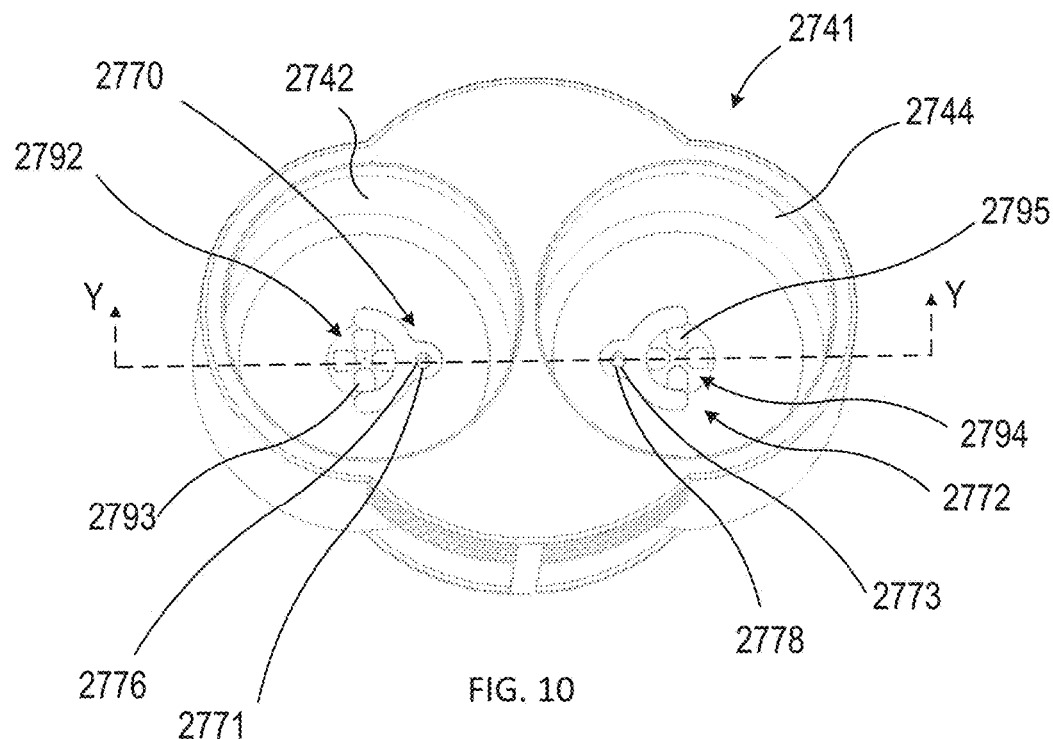
FIG. 10 is a top perspective view of a housing of the container assembly shown in FIGS. 7 and 8.
Figure 11:
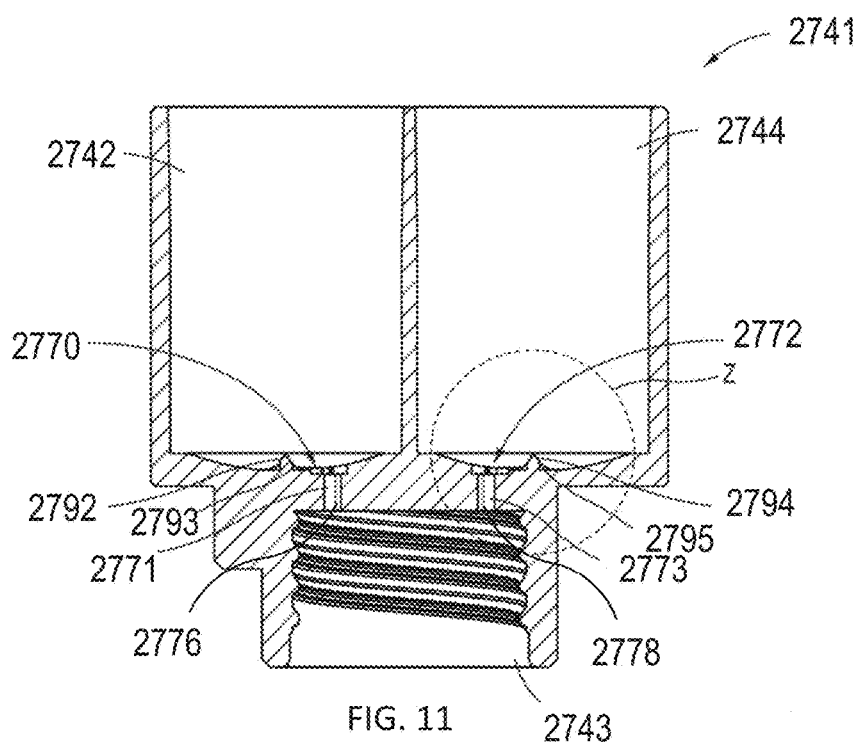
FIG. 11 is a cross-sectional view of the housing of the container assembly shown in FIGS. 7-8, and 10, taken along the line Y-Y in FIG. 10.

FIGS. 10-12 show a view of an interior portion of the housing 2741, a cross-sectional side view taken along line Y-Y in FIG. 10, and a detailed view of the cross-sectional side view shown in FIG. 11, respectively. As shown, the housing 2741 defines the first reagent volume 2742 configured to receive the first reagent container 2780 (not shown) and the second reagent volume 2744 configured to receive the second reagent container 2790 (not shown). The housing 2741 includes a first puncturer 2792, a second puncturer 2794, a first delivery portion 2770, and a second delivery portion 2772. In some embodiments, the housing 2741, the first delivery portion 2770, the second delivery portion 2772, the first puncturer 2792, and/or the second puncturer 2794 can be monolithically constructed. In other embodiments, the housing 2741, the first delivery portion 2770, the second delivery portion 2772, the first puncturer 2792, and/or the second puncturer 2794 can be formed separately and then joined together. In addition, as shown, the first delivery portion 2770 defines a first delivery path 2771 in fluid communication with the first puncturer 2792. Similarly, the second delivery portion 2772 defines a second delivery path 2773 in fluid communication with the second puncturer 2794. Each of the delivery paths 2771, 2773 defines a longitudinal center line CL, and has a length L and a size D. The longitudinal center line CL, and has a length L and a size D are shown in FIG. 12 for the delivery path 2773, but it is understood that the delivery path 2771 also has a length, a size, and a center line. Although shown as having a substantially circular cross-sectional shape (i.e., flow area), each of the delivery paths 2771, 2773 can have any suitable size and/or shape, and can accommodate any desired flow rate of the reagent R therethrough. For example, in some embodiments, each of the delivery paths 2771, 2773 can accommodate any suitable flow rate, e.g., 1 ml/sec, 2 ml/sec, 3 ml/sec, 4 ml/sec, 5 ml/sec. The ratio of the length L to the size D of each of the delivery paths 2771, 2773 can be any suitable value to produce the desired properties of the exit flow of the reagents therethrough. For example, in some embodiments, the ratio the length L to the size D of the delivery path 2771 or the delivery path 2773 is between about 2 and about 4. In other embodiments, the ratio the length L to the size D of the delivery path 2771 or the delivery path 2773 is between about 2.5 and about 3.5.

Figure 14:
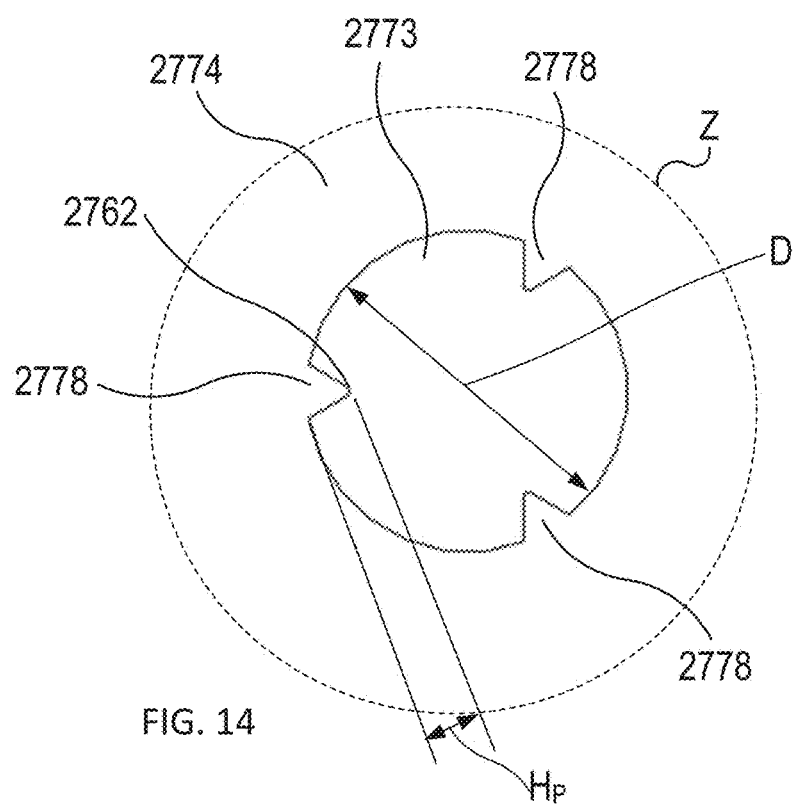
FIG. 14 is an enlarged view of the portion of the housing identified as region Z in FIG. 13.
Figure 15:
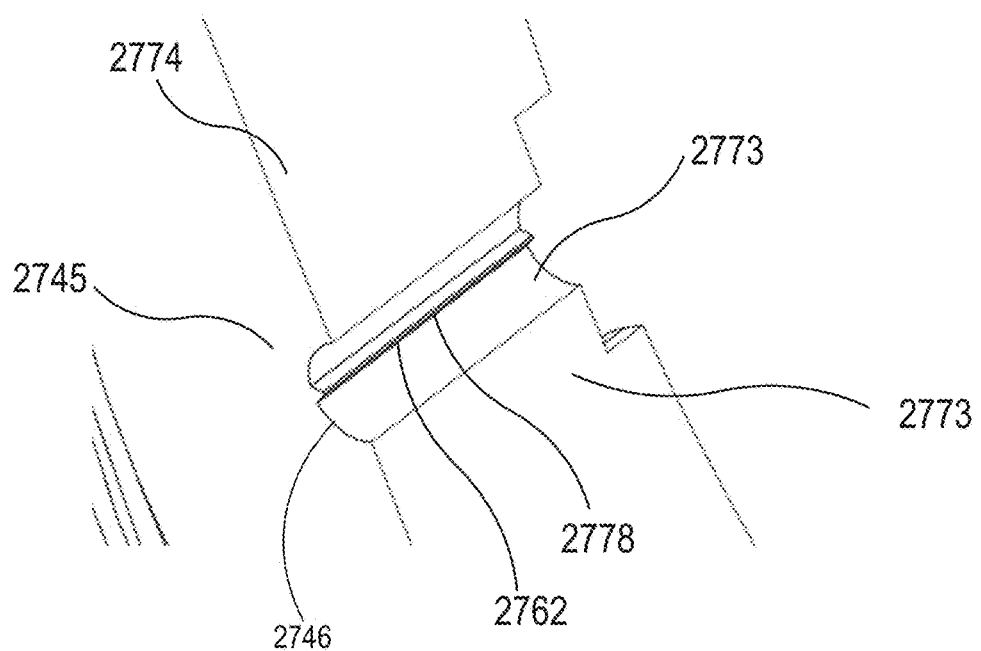
FIG. 15 is a perspective cross-sectional view of the portion of the housing shown in FIG. 14.

The side wall 2774 includes a first set of protrusions 2776 (also referred to as elongated protrusions, vanes, flow structures, or flow members) within the delivery path 2771, and a second set of protrusions 2778 (also referred to as elongated protrusions, vanes, flow structures, or flow members) within the delivery path 2773. FIGS. 14 and 15 show zoomed views of the portion of the side wall 2774 that defines the delivery path 2773 and the second set of protrusion 2776 therein. The first set of protrusions 2776 can be similar in shape, size and design to the second set of protrusions 2773 shown in FIGS. 14 and 15 and described below. As shown, the first delivery path 2771 includes three first protrusions 2776 evenly spaced around the circumference of the first delivery path 2771, and the second delivery path 2773 includes three second protrusions 2778 evenly spaced around the circumference of the second delivery path 2773. However, the first delivery path 2771 and the second delivery path 2773 can include any suitable number of first protrusions 2776 and second protrusions 2778, such as, for example, one protrusion, two protrusions, or four protrusions in each of the first delivery path 2771 and the second delivery path 2773. Additionally, the first protrusions 2776 and the second protrusions 2778 can be spaced in any arrangement in each of the first delivery path 2771 and the second delivery path 2773. For example, the first protrusions 2776 can be spaced so that all three of the first protrusions 2776 are on one side of the first delivery path 2771 or so that two of the first protrusions 2776 are spaced closer together compared to the third first protrusion 2776.

Although shown as being disposed from a proximal end of the delivery path 2773 to a distal end of the delivery path 2773, the protrusions 2778 can be disposed such that one, some, or all of the protrusions extend only partially through the length of the delivery path 2773, such as, for example, through the distal half of the delivery path. In some embodiments, the protrusion length $L_P$ can be less than the total length L of the delivery path 2773. For example, in some embodiments, the protrusion length $L_P$ can be at least ten percent of the length L of the delivery path 2773. In other embodiments, the protrusion length $L_P$ can be at least about fifty percent of the length L of the delivery path 2773. In yet other embodiments, the protrusion length $L_P$ can be the same length, or even greater than the length L of the delivery path 2773. For example, the protrusions 2778 can be fully within, or even extend outside of, an exit opening 2746 of the housing 2741. In this manner, the protrusions 2778 can act as a spray or stream guide to influence the exit flow of the reagent.

As shown in FIG. 14, the protrusions 2778 include an inwardly projecting sharp edge 2762. The protrusions 2778 can also extend inwardly into the delivery path 2773 by any suitable amount $H_p$ (e.g., the height of the protrusions 2778). For example, in some embodiments, the protrusions 2778 can extend a distance into the delivery path such that a ratio of the height $H_p$ to the size D of delivery path 2778 is between about 0.1 and about 0.2. Although the first protrusions 2776 and the second protrusions 2778 are shown as having an inwardly projecting sharp edge (e.g., the edge 2762), the first protrusions 2776 and the second protrusions 2778 can include any suitable shape and/or structure that creates a protuberance in a flow, such as a rounded inward projection.

The first puncturer 2792 and/or the second puncturer 2794 are configured to pierce (e.g., rupture) a first frangible portion 2788 of the first reagent container 2780 (not shown in FIG. 10, see FIGS. 8 and 12) and a second frangible portion of the second reagent container 2790 (not shown in FIG. 10, see FIGS. 8 and 12), respectively, to convey reagent from the first reagent container 2780 and/or the second reagent container 2790 into the reaction chamber 2732. Thus, the puncturer 2792 and the puncturer 2794 each include a sharp point, sharp edge and/or a protrusion, as shown, to pierce the first reagent container 2780 and the second reagent container 2790, respectively. Moreover, the first puncturer 2792 defines a first series of transfer pathways 2793 in fluid communication with the first reagent volume 2742, and the second puncturer 2794 defines a second series of transfer pathways 2795 in fluid communication with the second reagent volume 2744. In particular, each of the first series of transfer pathways 2793 and the second series of transfer pathways 2795 includes four channels spaced at approximately 90 degree intervals about the center point of the respective puncturer. Thus, as shown, the inclusion of the first series of transfer pathways 2793 and/or the second series of transfer pathways 2795 produces a discontinuous cross-sectional shape in the first puncturer 2792 and the second puncturer, respectively 2794. When the first puncturer 2792 pierces the first reagent container 2780, the first series of transfer pathways 2793 provides pathways through which the contents of the first reagent container 2780 can flow. Similarly, when the second puncturer 2794 pierces the second reagent container 2790, the second series of transfer pathways 2795 provides pathways through which the contents of the second reagent container 2790 can flow. Moreover, the arrangement of the first series of transfer pathways 2793, the second series of transfer pathways 2795, the cross-sectional shape of the first puncturer 2792, and/or the cross-sectional shape of the second puncturer 2794 can limit clogging or obstructions that may result from the piercing, thus providing a more repeatable delivery of the contents of the first reagent container 2780 and/or the second reagent container 2790.

As shown, the puncturer 2792 and/or the puncturer 2794 are disposed along and/or aligned with an axial centerline of the reagent volume 2742 and the reagent volume 2744, respectively. Similarly stated, the puncturer 2792 and the puncturer 2794 are centered with respect to the first reagent container 2780 and the second reagent container 2790, respectively. Such a configuration promotes repeatable, substantially complete delivery of the contents from the first reagent container 2780 and/or the second reagent container 2790, as described herein. In other embodiments, however, the puncturer 2792 and/or the puncturer 2794 can be offset from an axial centerline of the reagent volume 2742 and the reagent volume 2744, respectively. In such embodiments, for example, the offset can be based on a shape, size, slope, and/or configuration of the first delivery portion 2770, the second delivery portion 2772, and/or the reaction chamber 2732.

Although the cross-sectional shapes of the first series of transfer pathways 2793 and the second series of transfer pathways 2795 are shown in FIG. 10 as being curved and/or semi-circular, in other embodiments, the first series of transfer pathways 2793 and/or the second series of transfer pathways 2795 can have any suitable shape and configuration, such as for example, a helical shape, a tapered shape and/or the like. Moreover, although the shape and/or size of the first series of transfer pathways 2793 and/or the second series of transfer pathways 2795 are shown in FIG. 11 as having a vertical orientation and a constant diameter (cross-sectional area, flow area), in other embodiments the first series of transfer pathways 2793 and/or the second series of transfer pathways 2795 can have any suitable orientation, configuration, and size. For example, in some embodiments, the first series of transfer pathways 2793 and/or the second series of transfer pathways 2795 can have varying cross-sectional (or flow) areas (e.g., as a function of the distance from the puncturing tip) and/or non-vertical orientations (e.g., sloped). In this manner, the first series of transfer pathways 2793 and/or the second series of transfer pathways 2795 can be configured to promote a controlled and/or desired flow rate of the substances flowing therethrough. Moreover, although the first series of transfer pathways 2793 and the second series of transfer pathways 2795 are each shown in FIG. 10 as defining four channels, in other embodiments, a transfer pathway can define any suitable number of transfer channels.

FIGS. 11 and 12 show a cross-sectional view of the housing 2741 and a close-up cross-sectional view of a portion of the housing 2741 identified as region Z in FIG. 10, respectively. As shown, the first delivery path 2771 is in fluid communication with the first series of transfer pathways 2793, the first reagent volume 2742, and the interior volume of a connection portion 2743 of the housing 2741. Similarly, the second delivery path 2773 is in fluid communication with the second series of transfer pathways 2795, the second reagent volume 2744, and the connection portion 2743 of the housing 2741. As such, the first series of transfer pathways 2793 and the second series of transfer pathways 2795 are configured to place the reaction chamber 2732 in fluid communication with the first delivery path 2771 and the second delivery path 2773, respectively, and the reagent volume 2742 and the reagent volume 2744, respectively. In this manner, the contents of the first reagent container 2780 can be conveyed from the first reagent container 2780 to the reaction chamber 2732 via the reagent volume 2742, the first series of transfer pathways 2793, and/or the first delivery path 2771. Similarly, the contents of the second reagent container 2790 can be conveyed from the second reagent container 2790 to the reaction chamber 2732 via the reagent volume 2744, the second series of transfer pathways 2795, and/or the second delivery path 2773.

Moreover, although the housing 2741 is shown as having a first series of transfer pathways 2793 and a second series of transfer pathways 2795, in other embodiments, the housing 2741 can have (or define) any suitable number of transfer pathways and/or series of transfer pathways. Although not shown, in some embodiments, the first series of transfer pathways 2793 (or a portion thereof) and the second series of transfer pathways 2795 (or a portion thereof) can be in fluid communication with each other. For example, in some embodiments, the first series of transfer pathways 2793 and the second series of transfer pathways 2795 can be in fluid communication with each other via a transfer header pathway (not shown), wherein the transfer header pathway is in fluid communication with the reaction chamber 2732. In such embodiments, for example, the contents of the first reagent container 2780 can communicate (e.g., mix) with the contents of the second reagent container 2790 before reaching the reaction chamber 2732 or a portion thereof. Such an arrangement, in some embodiments, can promote mixing and/or minimize aeration, overspray and/or undesirable turbulence of the contents from the first reagent container 2780 and/or the second reagent container 2790. Additionally, the transfer header pathway can include protrusions similar to the first protrusions 2776 and/or the second protrusions 2778 to guide fluid from the first series of transfer pathways 2793 and the second series of pathways 2795.

Figure 16:
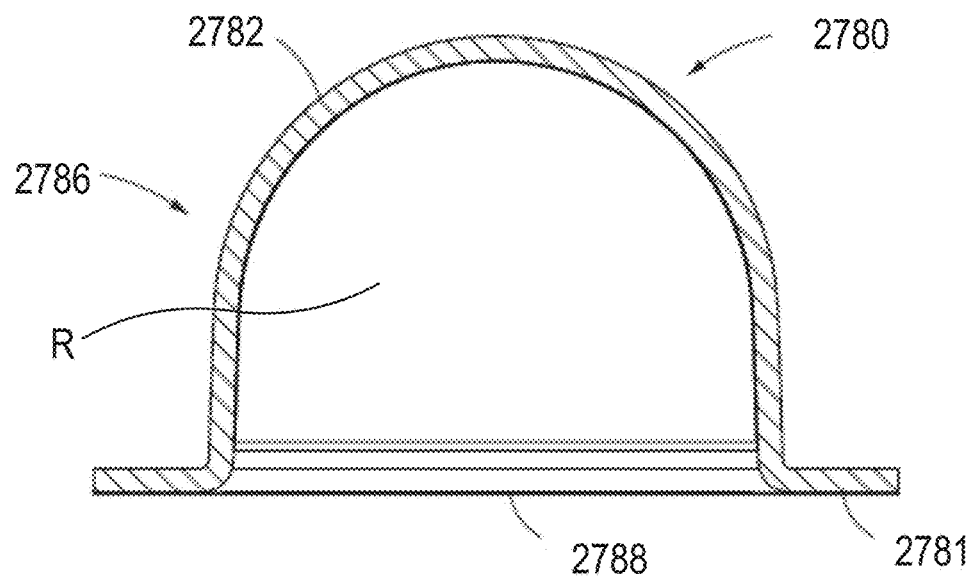
FIG. 16 is a cross-sectional view of a reagent container of the container assembly shown in FIGS. 7 and 8.
Figure 17:
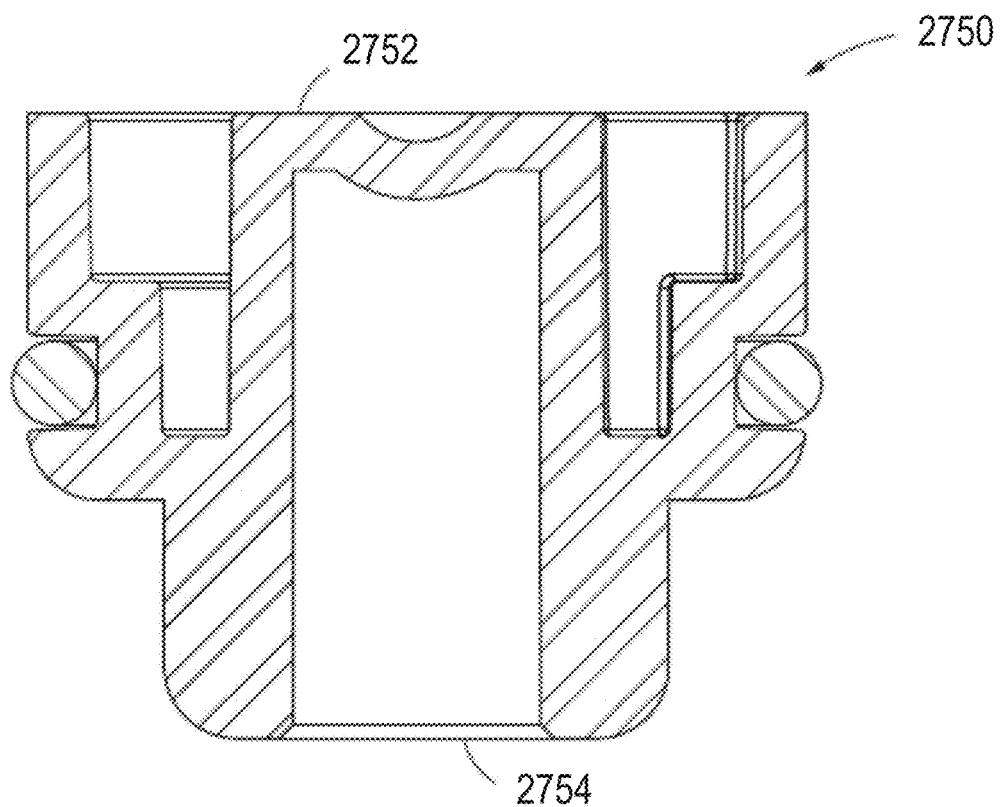
FIG. 17 is a cross-sectional view of an actuator of the container assembly shown in FIGS. 7 and 8.

Referring to FIGS. 8 and 17-19, the first actuator 2750 has a first plunger portion 2754 disposed within the first reagent volume 2742, and a first engagement portion 2752. The second actuator 2760 (not shown in FIG. 16) has a second plunger portion 2756 disposed within the second reagent volume 2744, and a second engagement portion 2753. Although the actuator shown in FIG. 17 is described herein with reference to actuator 2750 for ease of explanation, it should be understood that any feature described with reference to the first actuator 2750 can also, or alternatively, apply to the second actuator 2760, and vice-versa.

The first engagement portion 2752 of the first actuator 2750 is configured to be manipulated to move the first plunger portion 2754 within the first reagent volume 2742 to deform the first reagent container 2780. The second engagement portion 2753 of the second actuator 2760 is configured to be manipulated to move the second plunger portion 2756 within the second reagent volume 2744 to deform the second reagent container 2790. In this manner, movement of the plunger portion 2754 can urge the frangible portion 2788 of the first reagent container 2780 against the puncturer 2792 to pierce and/or rupture the frangible portion 2788. Similarly, movement of the plunger portion 2756 can urge the frangible portion 2789 of the second reagent container 2790 against the puncturer 2794 to pierce and/or rupture the frangible portion 2789. The plunger portion 2754 of the actuator 2750 and a portion of the housing 2741 can collectively define a seal to fluidically and/or optically isolate the reagent volume 2742 from a volume outside of the housing 2741. Similarly, the plunger portion 2756 of the actuator 2760 and a portion of the housing 2741 can collectively define a seal to fluidically and/or optically isolate the reagent volume 2744 from a volume outside of the housing 2741.

Moreover, although the plunger portion 2754 shown in FIG. 17 has a substantially planar surface for contacting the first reagent container 2780, in other embodiments, the plunger portion 2754 can be any suitable shape, size, and/or configuration. For example, in some embodiments, the plunger portion 2754 can correspond to (e.g., share a similar shape, cooperatively function) the first reagent container 2780 (e.g., the contact portion of the reagent container) and/or the puncturer 2792. For example, in some embodiments, the plunger portion 2754 can be curved (e.g., concave) so as to mate with a curved (e.g., concave) portion of the first reagent container 2780. In this manner, the plunger portion 2754 and the first reagent container 2780 can collectively and/or cooperatively function to limit dead volume. Moreover, such cooperation (e.g., mating) can promote repeatable delivery of the contents of the first reagent container 2780. Similarly, in some embodiments, for example, the plunger portion 2754 can be curved so as to mate with a curved portion of the puncturer 2792. In this manner, the plunger portion 2754 and the puncturer 2792 can collectively and/or cooperatively function to limit dead volume. Moreover, such cooperation (e.g., mating) can promote repeatable delivery of the contents of the reagent containers 2780.

As shown in FIG. 16, the first reagent container 2780 includes the first frangible portion 2788 and a sidewall 2786, which together define an internal volume. The internal volume can be completely or partially filled with a reagent and/or substance, as described herein. In addition, the first reagent container 2780 has a skirt 2781 (referred to as a "first skirt"), and a contact portion 2782 (referred to as a "first contact portion"). The skirt 2781 surrounds at least a portion of the first frangible portion 2788. In some embodiments, the sidewall 2786 can also be frangible. The second reagent container 2790 includes the second frangible portion 2789, a skirt 2791 (referred to as a "second skirt"), and a contact portion 2784 (referred to as a "second contact portion"). The second skirt 2791 surrounds at least a portion of the second frangible portion 2789. It should be noted that although the reagent container shown in FIG. 16 is described with reference to reagent container 2780 for ease of explanation, any feature described with reference to reagent container 2780 can also, or alternatively, apply to reagent container 2790 and vice-versa.

The first skirt 2781 and/or the second skirt 2791 can be any suitable size and/or shape, and can include any suitable surface design (e.g., smooth, rough and/or the like). For example, in some embodiments, the first skirt 2781 and/or the second skirt 2791 can be sized and/or shaped to correspond to a portion of the housing 2741. The first contact portion 2782 of the first reagent container 2780 and/or the second contact portion 2784 of the second reagent container 2790 can be any suitable size and/or shape. For example, in some embodiments, the first contact portion 2782 and/or the second contact portion 2784 can be sized and/or shaped to correspond to the first actuator 2750 and/or the second actuator 2760, respectively. For example, in such embodiments, the first contact portion 2782 and/or the second contact portion 2784 can include a concave portion, and the first actuator 2750 and/or the second actuator 2760 can be sized and/or shaped to correspond to the concave portion of the first contact portion 2782 and/or the concave portion of the second contact portion 2784, respectively. In this manner, the first reagent container 2780 and/or the second reagent container 2790 can be configured to promote substantially complete dispensation of their respective contents (e.g., reagents, substances, etc.), and/or promote a preferred pathway for the contents to travel from the first reagent container 2780 and/or the second reagent container 2790 when the first reagent container 2780 and/or the second reagent container 2790 are pierced.

Figure 18:
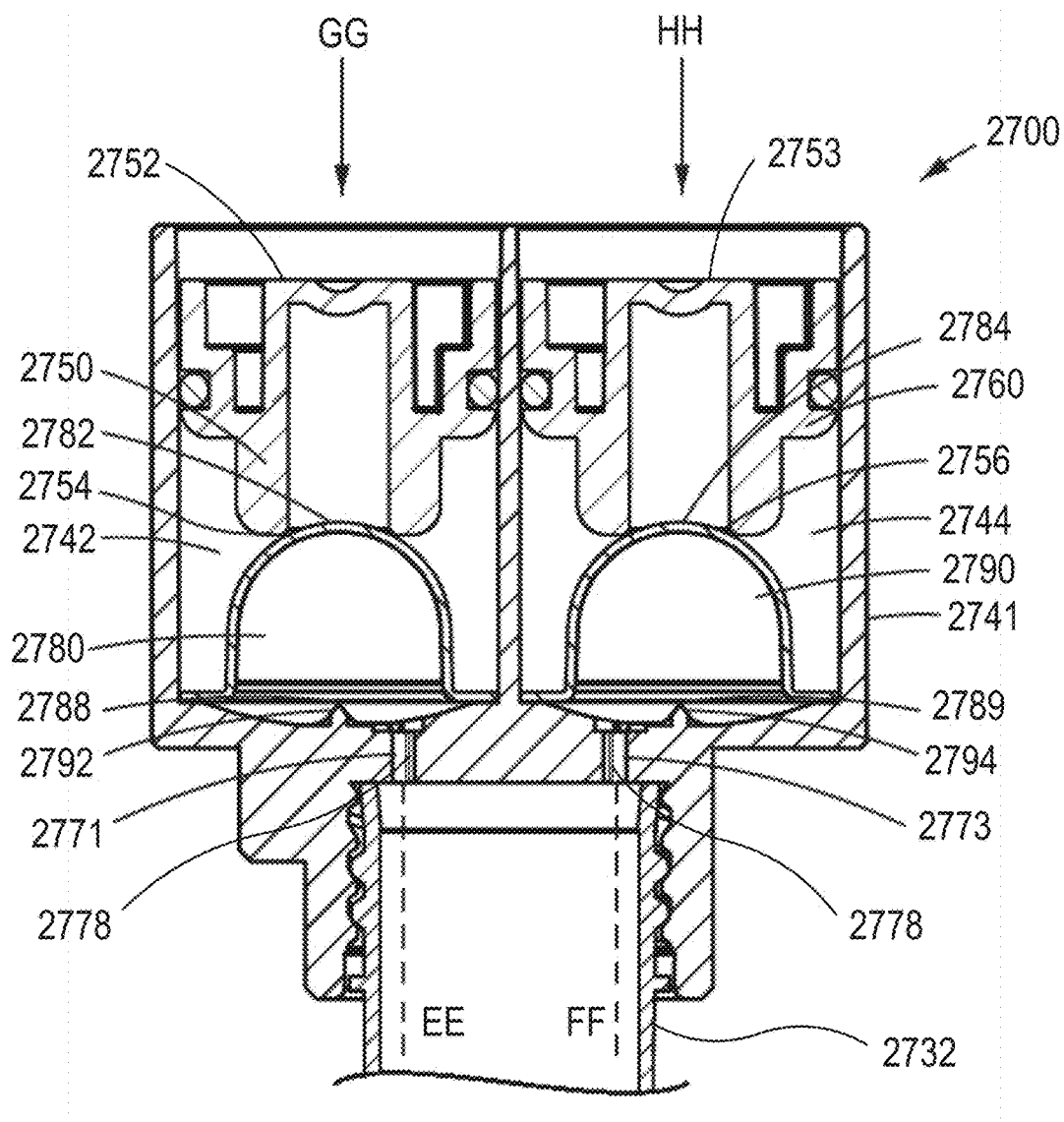
FIGS. 18 and 19 are cross-sectional views of a portion of the container assembly shown in FIGS. 7 and 8 in a first configuration and a second configuration, respectively.
Figure 19:
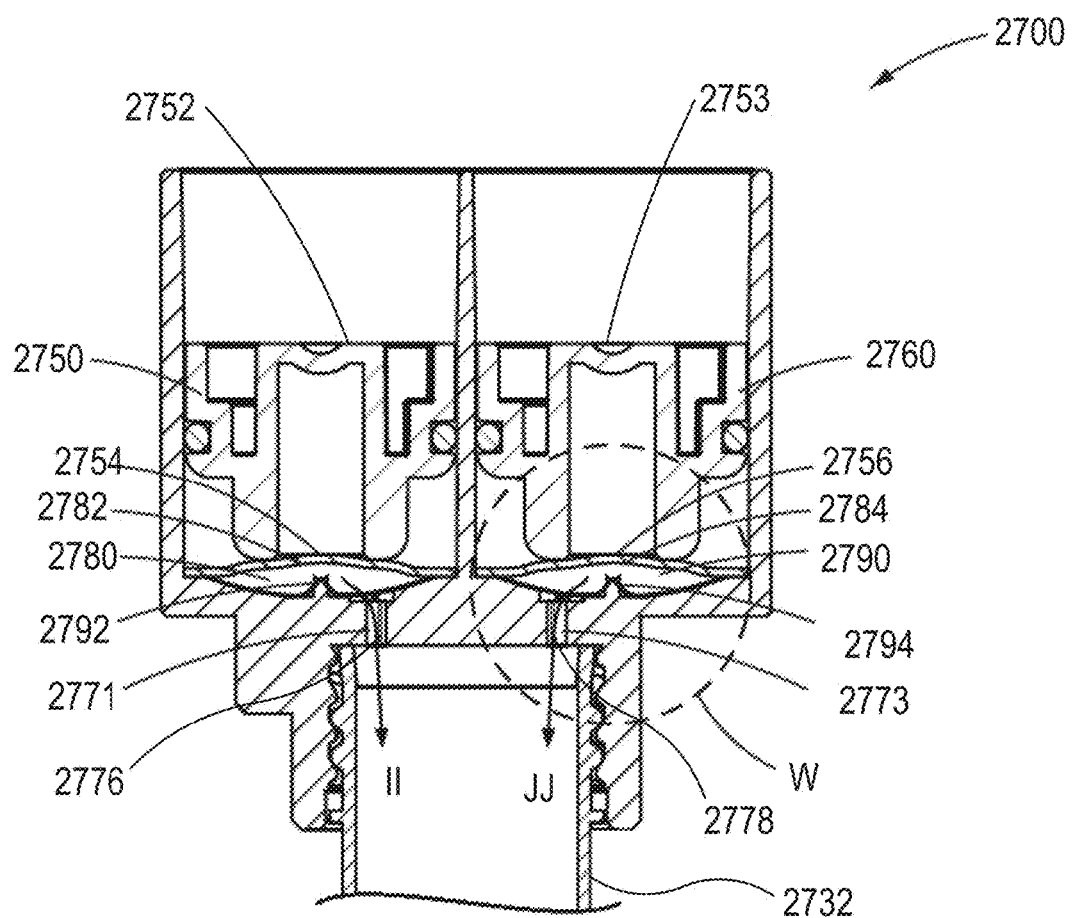

The first reagent container 2780 is shaped and sized to be disposed substantially inside the first reagent volume 2742. The second reagent container 2790 is shaped and sized to be disposed substantially inside the second reagent volume 2744. As best illustrated in FIGS. 18 and 19, the first reagent container 2780 can be maintained in a desired position by an interference fit between the first skirt 2781 and a portion of the housing 2741. Similarly, the second reagent container 2790 can be maintained in a desired position by an interference fit between the second skirt 2791 and a portion of the housing 2741. In this manner, a desired position of the first reagent container 2780 and/or the second reagent container 2790 can be substantially maintained relative to the housing 2741 during use.

In some embodiments, the first reagent container 2780 can be maintained in a desired position by a lock member (not shown) and by an interference fit between the first skirt 2781 and a portion of the housing 2741 and/or a portion of the lock member. Similarly, in such embodiments, the second reagent container 2790 can be maintained in a desired position by a lock member (not shown) and by an interference fit between the second skirt 2791 and a portion of the housing 2741 and/or a portion of the lock member.

The first reagent container 2780 and/or the second reagent container 2790 can have any suitable size and/or volume. For example, in some embodiments, the first reagent container 2780 and/or the second reagent container 2790 can have an internal volume of about 400 µL when in the expanded configuration. In such embodiments, the first reagent container 2780 and/or the second reagent container 2790 can initially contain about 300 µL to about 350 µL (and more particularly, about 325 µL) of any of the reagents described herein. Thus, when the first reagent container 2780 and/or the second reagent container 2790 are in their respective expanded configurations, they have a fill percentage of about 75 percent to about 88 percent. The first reagent container 2780 and/or the second reagent container 2790 are configured, along with their respective plungers and portions of the housing, such that when in their respective collapsed configurations, the dispensed volume is about 250 µL to about 300 µL (and more particularly, about 285 µL). Similarly stated, when the first reagent container 2780 and/or the second reagent container 2790 are in their respective collapsed configurations, they have a dispensation percentage of between about 76 percent and about 92 percent.

The first reagent container 2780 and the second reagent container 2790 can be completely or partially filled with any suitable reagent or substance. In some embodiments, the first reagent container 2780 and the second reagent container 2790 can include the same contents (e.g., the same reagent). In other embodiments, the first reagent container 2780 and the second reagent container 2790 can include dissimilar contents (e.g., the first reagent container 2780 contains a first reagent and the second reagent container contains a second reagent different than the first reagent). In some embodiments, for example, the first reagent container 2780 and/or the second reagent container 2790 can contain transduction particles that include an engineered nucleic acid formulated to cause the target cell (e.g., bacteria) to produce one or more reporter molecules. In some embodiments, the first reagent container 2780 and/or the second reagent container 2790 can contain one or more transduction particles engineered to be incapable of replication (e.g., lytic replication, lysogenic replication). For example, in some embodiments, the first reagent container 2780 and/or the second reagent container 2790 can contain any of the transduction particles described herein and in International Patent Publication No. WO2014/160418 (appl. no. PCT/US 2014/026536), entitled "Non-Replicative Transduction Particles and Transduction Particle-Based Reporter Systems," filed Mar. 13, 2014 or International Patent Application Publication No. WO2015/164746, entitled "Reagent Cartridge and Methods for Detection of Cells," filed Apr. 24, 2015, each of which is incorporated herein by reference in its entirety.

In some embodiments, the first reagent container 2780 and/or the second reagent container 2790 can contain a reagent formulated to react with one or more reporter molecules to generate and/or enhance production of a signal. For another example, the first reagent container 2780 and/or the second reagent container 2790 can include a substrate, such as tridecanal, that can interact with a reporter molecule (e.g., luciferase), to produce a measurable signal, e.g., via a luminescence reaction. The tridecanal solution can be, for example, CAS No. 10486-19-8, which has a density of 0.835 g/mL at 25 C and a dynamic viscosity of 0.0002323 Pa-sec. For yet another example, in some embodiments, the first reagent container 2780 and/or the second reagent container 2790 can include a nutrient, an antibiotic (e.g., Beta-lactams, extended-spectrum beta-lactams, Aminoglycosides, Ansamycins, Carbacephem, Carbapenems, any generation of Cephalosporins, Glycopeptides, Lincosamides, Lipopeptide, Macrolides, Monobactams, Nitrofurans, Oxazolidonones, Penicillins, Polypeptides, Quinolones, Fluoroquinolones, Sulfonamides, Tetracyclines, mycobacterial antibiotics, Chloramphenicol, Mupirocin), a lysis reagent, a sterilizing reagent, a colorant and/or the like.

The first reagent container 2780 and/or the second reagent container 2790 can be constructed from any suitable materials having any suitable dimensions. The thickness of the sidewall of the first reagent container 2780 and/or the second reagent container 2790 can be, for example, between about 0.010 inches and 0.020 inches. Moreover, the first reagent container 2780 and/or the second reagent container 2790 can be constructed from materials that are substantially impermeable to and/or substantially chemically inert from the substance(s) contained therein, e.g., transduction particle, substrate, antibiotics, buffers, surfactants, or any other reagent that can be used with the detection assay. At least a portion of the first reagent container 2780 (e.g., the frangible portion 2788) and/or at least a portion of the second reagent container 2790 (e.g., the frangible portion 2789) can be constructed from a material (e.g., polymer film, such as any form of polypropylene) having certain temperature characteristics such that the desired properties and integrity are maintained over a certain temperature. For example, in some instances, it can be desirable to store the first reagent container 2780 and/or the second reagent container 2790 containing reagent and/or substrate in a refrigerated condition. In some embodiments, a portion of the first reagent container 2780 and/or a portion of the second reagent container 2790 can be constructed from bi-axially oriented polypropylene (BOP). In some embodiments, a portion of the first reagent container 2780 and/or a portion of the second reagent container 2790 can be constructed from aluminum. In some embodiments, a portion of the first reagent container 2780 and/or a portion of the second reagent container 2790 can be constructed from polyvinyl chloride (PVC), ethylene vinyl alcohol (EVOH), polyethylene (PE), polychlorotrifluoroethene (PCTFE or PTFCE), a pharmaceutical-grade copolymer, cyclic olefin copolymer film, Tekniflex, COC P12P, PCTFE film lamination, and/or Tekniflex VA10200.

For example, in some embodiments, the first reagent container 2780 and/or the second reagent container 2790 can be constructed from PVC having a laminate of polyethylene EVOH on the interior surface of the sidewalls. In this manner, the laminate can function as an oxygen barrier to preserve the reagents contained within the first reagent container 2780 and/or the second reagent container 2790. In some embodiments, an outer surface can include a PCTFE coating to function as a moisture barrier. In some embodiments, the frangible portion 2788 and/or the frangible portion 2789 are weld sealed to the sidewalls. Moreover, in some embodiments, the frangible portion 2788 and/or the frangible portion 2789 can be devoid of the coatings to provide sufficient "puncturability" or minimum rupture strength for repeatable operation. In other embodiments, the frangible portion 2788 and/or the frangible portion 2789 can include a lacquer coating.

The reaction chamber 2732 can be removably coupled to the housing 2741. As shown, the reaction chamber 2732 is threadedly coupled to the housing 2741. In other embodiments, however, the reaction chamber 2732 can form an interference fit to couple the reaction chamber 2732 to the housing 2741. In this manner, the reagent module 2710 and the reaction chamber 2732 can be stored in a decoupled configuration (e.g., as a part of a sample collection or processing kit). A test sample can be placed into the reaction chamber 2732, and the housing 2741 can be coupled to the reaction chamber 2732 to form the container assembly 2700.

The reaction chamber 2732 includes a sidewall portion 2734 and a distal portion (including a bottom surface) 2736, and can be any suitable chamber for containing a clinical sample (e.g., a patient sample) in a manner that permits the monitoring, identification, and/or detection of a target cell (e.g., bacteria) within the sample via an instrument (such as the instrument 100 having a detector 212). In some embodiments, at least a portion of the reaction chamber 2732, such as the distal portion 2736, can be substantially transparent, for example, to allow viewing, and/or optical monitoring of the contents contained therein. In some embodiments, a portion of the reaction chamber 2732 (e.g., a distal portion) can be substantially transparent while the remainder of the reaction chamber 2732 can be substantially opaque. In this manner, the reaction chamber 2732 can be configured to convey light through the substantially transparent portion of the reaction chamber 2732, but block light at the substantially opaque portion of the reaction chamber 2732. In some embodiments, the sidewall portion 2734 of the reaction chamber 2732 can include a coating to allow for optimal transmission of light through the distal portion 2736 of the reaction chamber 2732. In some embodiments, the coating can be any suitable material configured to block and/or reflect light, for example, a label. In particular, in some embodiments, the label can be a white label to reflect light. Moreover, in some embodiments, the distal portion 2736 of the reaction chamber 2732 can be polished to promote optimal transmission of light therethrough.

As shown in FIG. 7, the distal portion of the reaction chamber 2732 includes a substantially flat bottom surface. The flat bottom surface promotes substantially uniform delivery of light therethrough. Specifically, in use, light can be transmitted through the distal portion substantially uniformly to a detector, such as for example, the detector 2212 shown in FIG. 9. Similarly stated, this arrangement allows a "bottom read" of the container assembly 2732 by the detector 2212 or any other suitable detector. Moreover, in use, such a substantially flat surface at the distal portion 2736 can result in the container assembly 2700 being placed consistently closer to and/or in contact with an optical detection window in the instrument 2100. In this manner, such a configuration can minimize the distance in the signal path between signal production and signal detection and/or minimize an interface between mismatched dialectic mediums in the signal path, both of which can contribute to loss in signal reaching the sensor, e.g., due to light scattering and/or light refraction. Moreover, in some embodiments, for example, the flat surface can be configured to contact the optical detection window.

The reaction chamber 2732 can be constructed from any suitable material, for example, glass, plastic (e.g., polypropylene), acrylic, etc. In some embodiments, the reaction chamber 2732 can be gamma sterilizable. In some embodiments, the reaction chamber 2732 can be a commercially available container, for example a centrifuge tube, an Eppendorf® tube, a glass vial, flat-bottomed vial/tube, round bottomed vial/tube, or any other suitable container. Although the reaction chamber 2732 is shown as being tapered in FIGS. 7 and 8, the reaction chamber 2732 can be shaped so that it has a constant diameter from the proximal end of the reaction chamber 2732 to the distal end of the reaction chamber 2732. Moreover, the reaction chamber 2732 can be shaped so that the exit axis EE and the exit axis FF do not intersect a sidewall of the reaction chamber, in order for the contents to flow directly from the first delivery path 2771 and the second delivery path 2773 to the sample.

In use, a sample is conveyed into the reaction chamber 2732 by any suitable mechanism. For example, the sample can be collected using a swab, such as those described in International Patent Application Publication No. WO2015/

164746, entitled "Reagent Cartridge and Methods for Detection of Cells," filed Apr. 24, 2015, which is incorporated herein by reference in its entirety. The reagent module 2710 is then assembled to the reaction chamber 2732. Specifically, as shown, the housing 2741 is threadedly coupled to the reaction chamber 2732 to form the container assembly 2700. The container assembly 2700 is then placed into an instrument, such as the instrument 2100 shown in FIG. 9, to manipulate the container assembly 2700 to detect the target molecules within the sample. For example, in some embodiments, the instrument 2100 can include a heating module (not shown) configured to heat the sample within the reaction chamber to promote cell replication, which results in higher production of the reporter molecules, for example, to generate a signal that is greater than a minimum signal threshold.

The heating, incubation and/or any mixing operations performed on the container assembly 2700 can be performed by the instrument 2100 when the container assembly 2700 is in any suitable configuration. For example, in some embodiments, any heating, incubation and/or mixing operation can be performed when the container assembly 2700 is in an initial (or first) configuration in which the first actuator 2750 and the second actuator 2760 are both in their initial position. In other embodiments, any heating, incubation and/or mixing operation can be performed when the container assembly 2700 is in an initial configuration in which the first actuator 2750 and the second actuator 2760 are in a final (or second) configuration, in which the first actuator 2750 and the second actuator 2760 are both in their final position and the reagents have been delivered into the reaction chamber 2732. In yet other embodiments, any heating, incubation and/or mixing operation can be performed when the container assembly 2700 is in any suitable intermediate configuration between the initial (or first) configuration and the final (or second) configuration.

FIGS. 18 and 19 show a cross-sectional side view of a portion of the container assembly 2700 in the initial (or first) configuration (FIG. 18) and the final (or second) configuration (FIG. 19), respectively. In the first configuration, the first actuator 2750 and the second actuator 2760 are positioned such that the first reagent container 2780 and the second reagent container 2790 disposed within the housing 2741 are substantially undeformed. Similarly stated, the first actuator 2750 and the second actuator 2760 are positioned such that they do not cause puncturer 2793 and puncturer 2794 to pierce the first reagent container 2780 and the second reagent container 2790, respectively. Thus, the container assembly 2700 is in a "ready" state when in the first configuration. In some embodiments, the container assembly 2700 can include a safety mechanism (not shown) to prevent and/or limit movement of the first actuator 2750 and/or the second actuator 2760 relative to the housing 2741 until desired by the operator.

In some embodiments, to facilitate the production of reporter molecules, a first reagent (e.g. from the first reagent container 2780) can be conveyed into the sample within the reaction chamber 2732. This operation can be performed before, during, or after a mixing, heating or incubation operation performed by the instrument 2100. To actuate the container assembly 2700, a force is applied to the engagement portion 2752 of the first actuator 2750, thus causing the first actuator 2750 to move as shown by the arrow GG in FIG. 18. The force can be applied by any suitable mechanism within instrument 2100, such as those shown and described in the '928 publication. More particularly, the first actuator 2750 is manipulated (e.g., at the first engagement portion 2752) to move the first plunger portion 2754 within the housing 2741 such that the first plunger portion 2754 engages the contact portion 2782 of the first reagent container 2780 to partially deform the first reagent container 2780 from the first configuration to the second configuration. As the first plunger portion 2754 engages the first reagent container 2780, the first puncturer 2792 pierces a portion of the first reagent container 2780 (e.g., the frangible portion 2788) to convey reagent from the first reagent container 2780 into the first reagent volume 2742, the first delivery portion 2770, and/or the reaction chamber 2732.

At the desired time, the instrument 2100 can then manipulate the container assembly 2700 to detect the presence of a target molecule (e.g., via a reporter molecule) within the sample. Such manipulation can include, for example, exerting a force on the container assembly 2700 and/or the reagent module 2710 to move a distal end portion of the reaction chamber 2732 into the detection volume 2234 of the instrument 2100 (see e.g., FIG. 9). In some embodiments, the force can be maintained such that the distal end portion of the reaction chamber 2732 is maintained in a constant and/or repeatable position relative to the detector 2212. The container assembly 2700 can then be actuated at a second time to deliver a second reagent into the reaction chamber 2732 to facilitate a detection operation. In some embodiments, the detector 2212 can begin receiving a signal (e.g., "reading") after the distal end portion of the reaction chamber 2732 is in within the detection volume 2234, and can continue receiving the signal before, during, and after the addition of the reagent. In other embodiments, the container assembly 2700 can be actuated at any time during the detection operation.

To actuate the container assembly 2700 at the second time, a force is applied to the engagement portion 2753 of the second actuator 2760, thus causing the second actuator 2760 to move as shown by the arrow HH in FIG. 18. The force can be applied by any suitable mechanism within instrument 2100, such as those shown and described in the '928 publication. More particularly, the second actuator 2760 is manipulated (e.g., at the second engagement portion 2753) to move the second plunger portion 2756 within the housing 2741 such that the second plunger portion 2756 engages the second contact portion 2784 of the second reagent container 2790 to partially deform the second reagent container 2790 from the first configuration to the second configuration. As the second plunger portion 2756 engages the second reagent container 2790, the second puncturer 2794 pierces a portion of the second reagent container 2790 (e.g., the frangible portion 2789) to convey reagent from the second reagent container 2790 into the second reagent volume 2744, the second delivery portion 2772, and/or the reaction chamber 2732.

Figure 20:
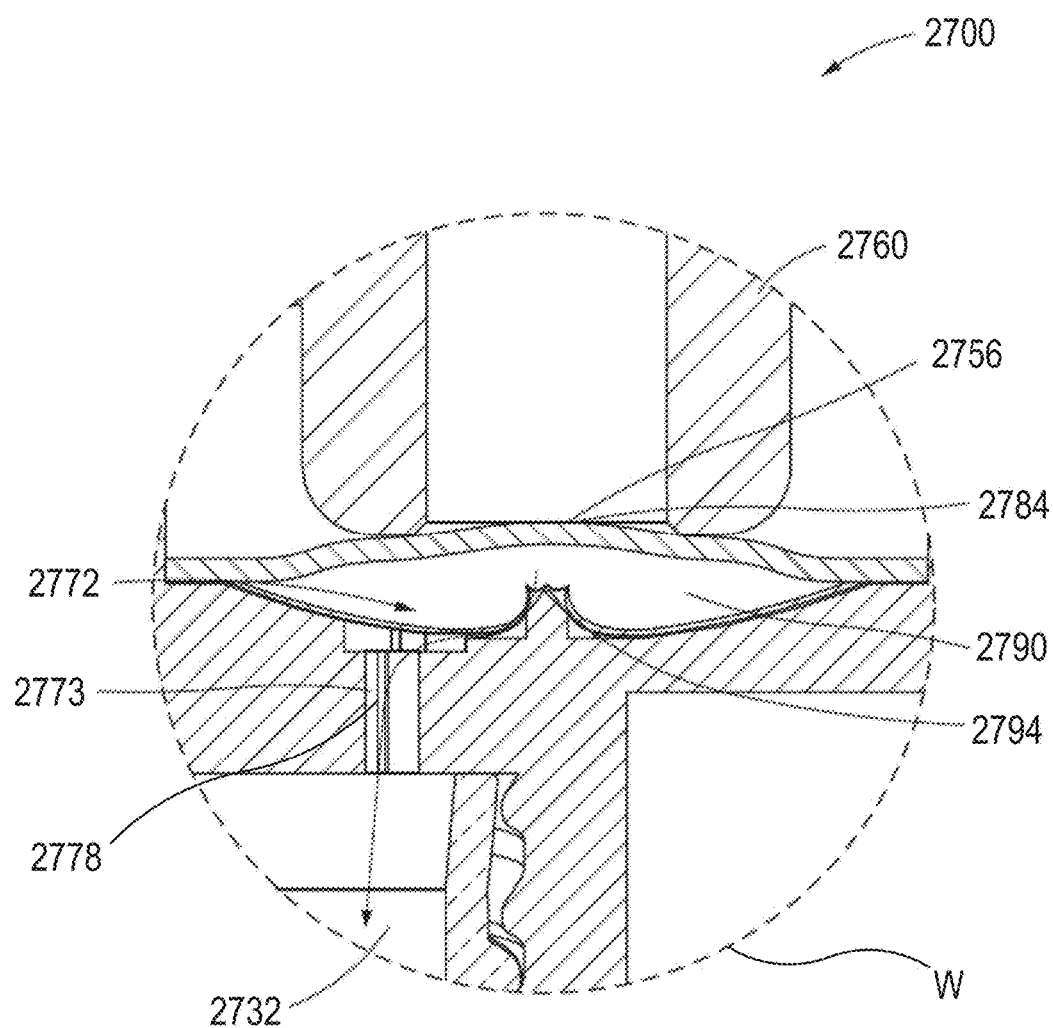
FIG. 20 is an enlarged view of the portion of the container assembly identified as region W in FIG. 19.

FIG. 19, and in greater detail in FIG. 20, shows the portion indicated by region W in FIG. 19, the container assembly 2700 in the final (or second) configuration. In the second configuration, the first actuator 2750 and the second actuator 2760 are positioned such that the first reagent container 2780 and the second reagent container 2790 are substantially deformed and/or collapsed. Similarly stated, the first actuator 2750 and the second actuator 2760 are positioned such that at least portions of the respective forces are transferred to the first reagent container 2780 and the second reagent container 2790, respectively. In such a configuration, as shown, the first puncturer 2792 has pierced the first reagent container 2780 such that a desired amount of the contents of the first reagent container 2780 have substantially exited the first reagent container 2780, and entered the first delivery portion 2770 and/or the reaction chamber 2732, as shown by the arrow II. Similarly, the second puncturer 2794 has pierced the second reagent container 2790 such that a desired amount of the contents of the second reagent container 2790 have substantially exited the second reagent container 2790, and entered the second delivery portion 2772 and/or the reaction chamber 2732, as shown by the arrow JJ. Although described above as being actuated at two different times, in some embodiments, the first actuator 2750 and the second actuator 2760 can be actuated substantially simultaneously, in accordance with the desired assay.

In some embodiments, the container assembly 2700 can be used in conjunction with an assay produces a luciferase reaction that includes the formation of a complex between luciferase and flavin mononucleotide. In the absence of a suitable aldehyde (i.e., the reagent R, also referred to as the substrate), this complex is unable to proceed in the luminescence reaction. The luciferase reaction proceeds and emits light upon the addition of the aldehyde, and ideally, it is preferable that all complexed luciferases be triggered to emit photons simultaneously. Thus, by conveying the reagent (e.g., tridecanal) from the second reagent container 2790 during the detection operation, a flux of photons can be emitted in a short period of time. Similarly stated, the addition of the reagent from the second reagent container 2790 can facilitate the production of a flash of light that can be readily detected by the detector 2212.

As supported by the test results presented herein, however, if the reagent and/or substrate is conveyed into the reaction chamber at a rate that is too high, the amount of light detected will decrease and/or the amount of light detected from replicates will exhibit increased variability resulting in an increase in the coefficient of variation associated with light detection. This reduction in performance is related to splashing and/or formation of bubbles in the solution that can result when the reagent and/or substrate is conveyed at a high velocity. Conversely, if the reagent and/or substrate is conveyed into the reaction chamber at a rate that is too low, the emitted light may be slow to develop and may not reach the peak levels for accurate detection. Such reduction in light output can be related to slow delivery of the reagent, delivery of the reagent in a manner that does not facilitate rapid mixing with the sample, delivering the reagent in a manner such that the reagent adheres to the walls of the housing 2741 and/or the reaction chamber 2732 (and does not reach the sample), or the like. Accordingly, the mixing of the reagent and/or substrate can be controlled to produce the desired light output performance.

As described above with respect to the protrusion 776 and the protrusions 1776, the first set of protrusions 2776 and the second set of protrusions 2778 control the behavior of the contents of the first reagent container 2780, the second reagent container 2790, the first reaction volume 2742, and/or the second reaction volume 2744 as the contents travel through the first delivery portion 2770 and/or the second delivery portion 2772, respectively. In other words, the spray or jet geometry can be influenced by any of the protrusions 2776, 2778, the properties of the reagents, or the flow paths through which the reagents travel. An uncontrolled spray of the contents may result in the contents attaching to the walls of the reaction chamber 2732, causing at least a portion of the reagents (either from the first reagent container 2780 or the second reagent container 2790) to reach the sample gradually or not reach the sample at all. Because a detectable flash reaction requires that the reagent reach the sample quickly and in a controlled manner, an uncontrolled spray may cause inconsistent results and/or false negatives that a reporter molecule is present in the sample. Additionally, an uncontrolled spray of the contents can cause aeration of the sample, production of bubbles, and splashing, which can reduce visibility of the reaction or slow the reaction to levels that are not consistently detectable. That is, the signal produced by the luciferase reaction may not be repeatable or consistent for a given level of reporter molecules within the sample.

There are many mechanisms by which the protrusions 2776, 2778 can control the flow (e.g. the plume, stream or jet) of the reagents upon actuation of the reagent module 2710. For example, the first set of protrusions 2776 and/or the second set of protrusions 2778 can direct the reagent distally toward the sample in the reaction chamber 2732, thereby reducing attachment of the contents to the end surface 2745 or the walls of the reaction chamber 2732. This is shown, for example, by the arrows II and JJ in FIG. 19. The first set of protrusions 2776 and/or the second set of protrusions 2778 can cause the flow of reagents to be directed toward the sample and to control the plume or jet such that even if there are a small number of reporter molecules present in the sample, the reagent (e.g., tridecanal) will mix with the sample quickly enough that a detectable signal from the flash reaction will be produced. Additionally, the first set of protrusions 2776 and/or the second set of protrusions 2778 can control the spray of the contents so that the aeration of the sample, production of bubbles, and splashing are minimized and do not disrupt the detection of the flash reaction.

In some embodiments, for example, the first set of protrusions 2776 and/or the second set of protrusions 2778 can limit the vorticity (or "swirling motion") of the reagent as it flows through the first delivery path 2771 and the second delivery path 2773, respectively. By limiting the non-longitudinal velocity of the flow, the plume (also referred to as a jet or stream) can be a narrow, but high speed stream conveyed into the reaction chamber. The stream or plume of the reagent can have a maximum width, similar to the maximum width W shown and described above with respect to the actuation of the container assembly 700 and the container assembly 1700. The ratio of the maximum width to the size D of the delivery path 2771 (or the size D of the delivery path 2773) can be any suitable value, for example, to limit impingement of the reagent onto the walls of the reaction chamber 2732. In some embodiments, the ratio of the maximum width to the size D of the delivery path 2771 and/or the delivery path 2773 can be less than about 2. In other embodiments, the ratio of the maximum width to the size D of the delivery path 2771 and/or the delivery path 2773 can be less than about 4.

Additionally, the reagents and/or substrate can be conveyed from the reagent module 2710 at a velocity and/or flow rate to promote mixing and/or reduce turbulence. By reducing flow turbulence, the plume, jet or stream exiting the flow path can have limited non-longitudinal velocity components, and thus, can mix more effectively with the sample, as described herein. For example, in some embodiments, the mixing of the reagent and/or substrate includes conveying the reagent and/or substrate into the reaction chamber by moving the first actuator 2750 and/or the second actuator 2760 linearly at a rate of between about 20 mm per second and about 90 mm per second. The delivery rates for conveying the contents of the first reagent container 2780 (e.g., the transduction particles) can be different than the delivery rate for conveying the contents of the second reagent container 2790 (e.g., the substrate) because of the different mixing requirements, timing, and the like. In some embodiments, for example, the first actuator 2750 can be moved at a rate of between about 10 mm/sec and about 30 mm/sec. The length of travel in such embodiments can be between about 8 mm and about 10 mm, thus the delivery time for conveying the reagent from the first reagent container 2780 can be between about 0.25 seconds and about 1.0 seconds. As described below, the delivery volume of reagent (e.g., transduction particles) can be about 0.3 ml, thus the flow rate of delivery can be between about 0.3 ml/sec and about 1.2 ml/sec. In some embodiments, the second actuator 2760 can be moved at a rate of between about 30 mm/sec and about 50 mm/sec. In particular, in some embodiments, the second actuator 2760 can be moved at a rate of about 38 mm/sec. The length of travel in such embodiments can be between about 8 mm and about 10 mm, thus the delivery time for conveying the reagent from the second reagent container 2790 can be between about 0.2 seconds and about 0.26 seconds. In other embodiments, the delivery time for conveying the reagent from the second reagent container 2790 can be between about 0.2 seconds and about 0.3 seconds. As described herein, reducing the delivery time to shorter values can cause aeration of the sample, production of bubbles, and splashing, all of which can disrupt the detection of the flash reaction. As described below, the delivery volume of reagent (e.g., substrate) can be about 0.3 ml, thus the flow rate of delivery can be between about 1.1 ml/sec and about 1.5 ml/sec. In other embodiments, the flow rate of delivery can be between about 0.5 ml/sec and about 1.5 ml/sec.

As described above, in some embodiments, it is desirable to produce a laminar flow of the reagent at the exit openings. A laminar flow of the reagent R can produce a more repeatable delivery of the substrate (e.g., by limiting the non-longitudinal flow components) as discussed herein. It is understood that the flow characteristics (i.e., laminar vs. turbulent) for a flow within an internal channel, such as the delivery path 2771 and/or the delivery path 2773 can be assessed by evaluating the Reynolds number:

$$\text{Re} = \frac{\rho v D}{\mu} \quad (3)$$

Where $\rho$ is the density of the fluid, $\mu$ is the viscosity of the fluid, $v$ is the velocity of the fluid within the channel, and $D$ is the diameter (or hydraulic diameter) of the channel (e.g., the delivery paths 2771, 2773). By controlling (i.e., reducing) the Reynolds number, the exit flow can be maintained as a laminar flow. Thus, in some embodiments, the size D of the delivery paths 2771, 2773, the kinematic viscosity of the reagent (the kinematic viscosity being $\mu/\rho$), and the actuation speed can be such that the exit flow of the reagent is laminar. The inclusion of the protrusions 2776, 2778 can, for example, act to reduce the characteristic (or hydraulic) diameter D of the delivery paths, thereby reducing the Reynolds number as compared to that which would be for a delivery path without any protrusion.

When the first reagent container 2780 and/or the second reagent container 2790 are deformed, a desired amount of its contents are conveyed into the reaction chamber 2732 in a manner such that "dead volume" is limited and/or substantially eliminated. As used herein the "dead volume" is the volume of reagent that is dispensed from the first reagent container 2780 and/or the second reagent container 2790 but that is not conveyed into reaction chamber 2732. The dead volume can include, for example, the volume of the delivery paths and the transfer pathways. In some embodiments, the first reagent container 2780 and/or the second reagent container 2790 can be configured to limit the dead volume therein when the assembly 2700 is actuated. For example, in some embodiments, the contact portion 2782 and/or the contact portion 2784 can be configured, along with the corresponding engagement portions of the actuator 2750 and actuator 2760, respectively, to deform in a controlled manner that reduces the dead volume. In this manner, the first reagent container 2780 and/or the second reagent container 2790 can be configured to promote a consistent and/or repeatable dispensation of their contents (e.g., reagents).

In some embodiments, the cap assembly (i.e., the first reagent container 2780 and/or the second reagent container 2790 along with their respective plungers and portions of the housing) is configured such that the "dead volume" is between about 30 μL and about 50 μL. In some embodiments, the cap assembly is configured such that the "dead volume" about 40 μL±9 μL. By limiting the part-to-part variation in the dead volume, the accuracy of reagent delivery, and thus, the accuracy of the assay, can be improved. In some embodiments, for example, the cap assembly is configured such that the dispensed volume is about 285 μL with a coefficient of variation of about three percent.

Figure 21:
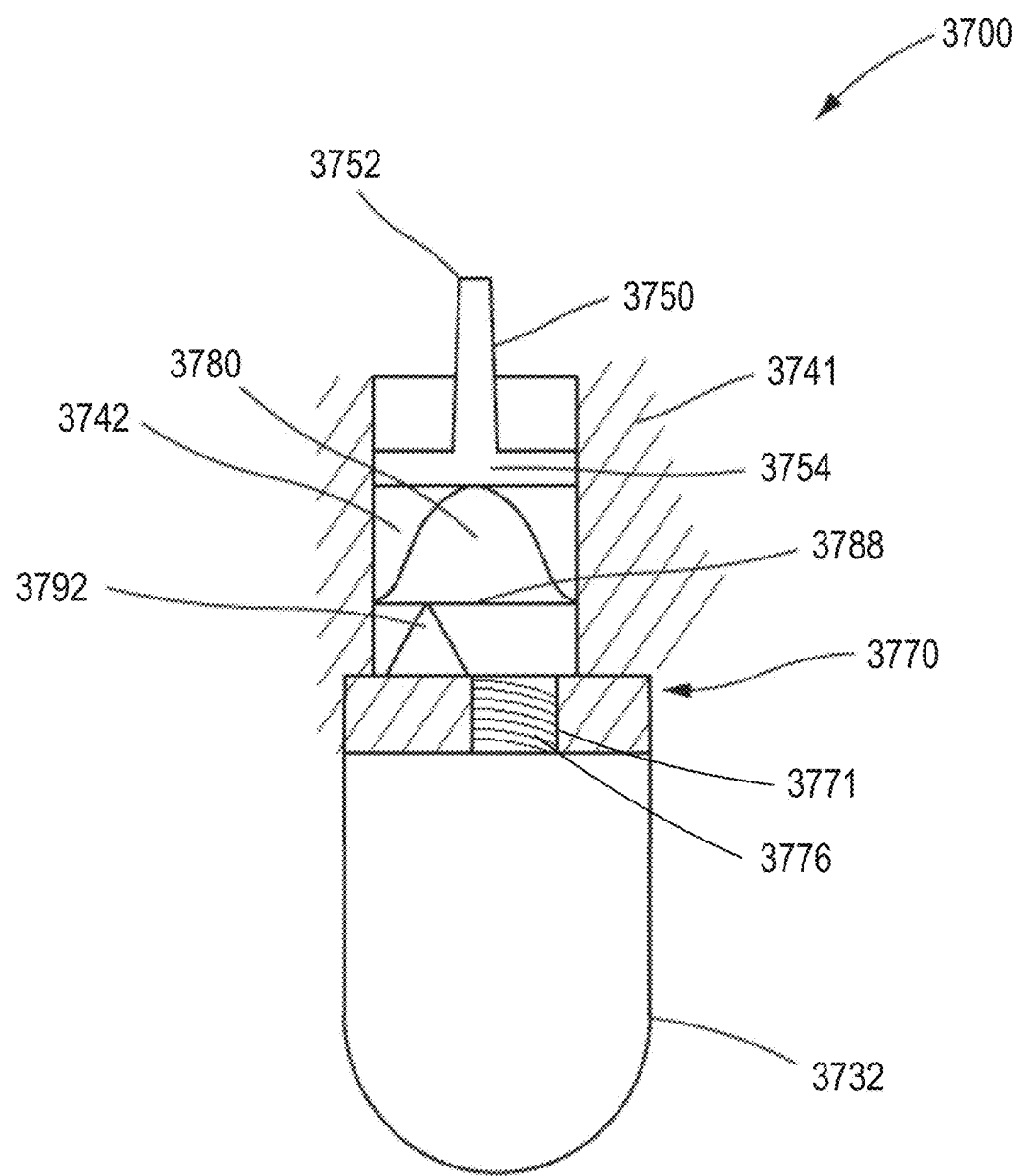
FIG. 21 is a schematic illustration of a container assembly, according to an embodiment.

Although the first protrusions 2776 of the first delivery path 2771 and the second protrusions 2778 of the second delivery path 2773 are shown as being elongated protrusions that lie parallel to the longitudinal axis of the first delivery path 2771 and the second delivery path 2773, respectively, the protrusions 2776, 2778 can also be shaped in a helical configuration around the longitudinal central axis of the first delivery path 2771 or the second delivery path 2773. Such embodiments can be useful, for example, where a swirl or rotational velocity component is desired (e.g., to affect mixing with the sample). For example, FIG. 21 is a schematic illustration of a container assembly 3700. The container assembly 3700 can be used with and manipulated by any of the instruments and/or any of the components described herein and in U.S. Patent Publication No. 2014/0272928, entitled "Systems and Methods for Detection of Cells using Engineered Transduction Particles" ("the '928 publication"), which is incorporated herein by reference in its entirety, and in International Patent Publication No. WO2015/164746, entitled "Reagent Cartridge and Methods for Detection of Cells," which is incorporated herein by reference in its entirety. In this manner, the container assembly 3700 and any of the container assemblies described herein can be used to detect and/or identify target cells (e.g., bacteria) within a sample according to any of the methods described herein or in the '928 publication. For example, in some embodiments, the container assembly 3700 can be used to dispose and/or mix a reagent into a sample while maintaining fluidic isolation between the container and an outside region. In this manner, the method of cell identification can be performed in a closed system and/or a homogeneous assay. Similarly stated, in some embodiments the container assembly 3700 is used in methods of cell identification and/or detection that do not involve removal of contents from the container assembly 3700, separation of the contents within the container assembly 3700, washing of the contents within the container assembly 3700 and/or rinsing of the contents within the container assembly 3700.

The container assembly 3700 includes a housing 3741, an actuator 3750, and a reaction chamber 3732 that is defined by a sample container (e.g., a sample tube or the like). The housing 3741 is removably coupled to the reaction chamber 3732. For example, in some embodiments, the housing 3741 can be threadedly coupled to the reaction chamber 3732. In other embodiments, the housing 3741 and the reaction chamber 3732 can form an interference fit to couple the housing 3741 to the reaction chamber 3732. The housing 3741 defines a reagent volume 3742 configured to receive a reagent container 3780. The housing 3741 includes a puncturer 3792 and a delivery portion 3770. In some embodiments, the housing 3741, the delivery portion 3770 and/or the puncturer 3792 can be monolithically constructed. In other embodiments, the housing 3741, the delivery portion 3770 and/or the puncturer 3792 can be formed separately and then joined together. The delivery portion 3770 includes delivery path 3771 for transfer of the contents of the reagent volume 3742 and/or the reagent container 3780 to the reaction chamber 3732. The delivery path 3771 includes a helical protrusion 3776 (also referred to as an elongated protrusion, a vane, a flow structure, or a flow member), which is shaped such that the helical protrusion 3776 curves around the longitudinal central axis of the delivery path 3771. Although shown and described as including only one continuous helical protrusion 3776, the delivery path 3771 can include any suitable number of helical protrusions 3776, such as, for example, one or four. Additionally, although shown as extending from the proximal end of the delivery path 3771 to the distal end of the delivery path 3771, the helical protrusion 3776 can extend through only a portion of the delivery path 3771. Although described and shown in FIG. 21 as including a protrusion, in some alternative implementations, the housing 3741 need not include a protrusion, similar to the embodiment shown in FIGS. 1 and 2.

The actuator 3750 has a plunger portion 3754 disposed within the reagent volume 3742 and an engagement portion 3752. The engagement portion 3752 of the actuator 3750 is configured to be manipulated to move the plunger portion 3754 within the reagent volume 3742 to deform the reagent container 3780. In this manner, movement of the plunger portion 3754 can urge the frangible portion 3788 of the reagent container 3780 against the puncturer 3792 to pierce and/or rupture the frangible portion 3788. The plunger portion 3754 of the actuator 3750 and a portion of the housing 3741 can collectively define a seal to fluidically and/or optically isolate the reagent volume 3742 from a volume outside of the housing 3741. With the exception of the helical protrusion 3776, the components of the container assembly 3700 are similar in structure and function to the container assembly 1700 described above and will not be further described herein.

In use, the actuator 3750 (e.g., the engagement portion 3752) is manipulated to move the plunger portion 3754 within the housing 3741 such that the plunger portion 3754 engages a contact portion (not identified in FIG. 16) of the reagent container 3780 to partially deform the reagent container 3780 from a first configuration (shown in FIG. 16) to a second configuration (not shown). As the plunger portion 3754 engages the contact portion of the reagent container 3780, the puncturer 3792 pierces a portion of the reagent container 3780 (e.g., a frangible portion 3788) to convey the contents (e.g., a reagent) from the reagent container 3780 into the reaction volume 3742, the delivery portion 3770, and/or the reaction chamber 3732. From the second configuration to a third configuration (not shown), the actuator 3750 is manipulated to move the plunger portion 3754 within the housing 3741 such that the plunger portion 3754 engages a contact portion of the reagent container 3780 to deform the reagent container 3780 from the second configuration to the third configuration. As the reagent container 3780 deforms from the second configuration to the third configuration, substantially all of its contents is conveyed from the reagent container 3780 into the reaction volume 3742, the delivery portion 3770, and/or the reaction chamber 3732, such that "dead volume" in the reagent container 3780 is limited. In this manner, substantially repeatable delivery of the contents from the reagent container 3780 to the reaction chamber 3732 can be obtained. For example, in some embodiments, a deformation of a first reagent container at a first time and a deformation of a second reagent container at a second time after the first time can be substantially similar, thereby allowing for substantially all of the contents to be transferred from the reagent container 3780 at the first time and the second time. Moreover, this arrangement can limit clogging or obstructions that may result from the piercing of the reagent container 3780, thus providing a more repeatable delivery of the contents of the reagent container 3780.

As the contents of the reagent container 3780 and/or the reaction volume 3742 are delivered through the delivery path 3771 of the delivery portion 3770, the helical protrusion 3776 controls the behavior of the contents such that the contents exit the delivery path 3771 in a controlled plume. If the delivery path 3771 lacked a protrusion, pressure gradients that may exist near the outlet of the delivery path 3771 may cause the contents to exit the delivery path 3771 as a wide, uncontrolled spray, as described above and with reference to dashed lines B in FIGS. 3-5. An uncontrolled spray of the contents may result in the contents attaching to the walls of the reaction chamber 3732, causing at least a portion of the contents to reach the sample gradually or not reach the sample at all. Because a detectable flash reaction requires the contents to reach the sample quickly and within a short period of time, an uncontrolled spray may cause inconsistent results and/or false negatives that a reporter molecule is present in the sample. Additionally, an uncontrolled spray of the contents can cause aeration of the sample, production of bubbles, and splashing, which can reduce visibility of the reaction or slow the reaction to levels that are not consistently detectable. The helical protrusion 3776 directs the contents distally toward the sample in the reaction chamber 3732, reducing attachment of the contents to the walls of the reaction chamber 3732. The helical protrusion 3776 controls the behavior of the contents such that a substantially repeatable flash reaction occurs when reporter molecules are present, even at low signal levels. In other words, the helical protrusion 3776 causes the flow of contents to be directed toward the sample and the helical protrusion 3776 controls the spray such that even if there are a small number of reporter molecules present in the sample, the reagent and/or the substrate will mix with the sample quickly enough that a detectable flash reaction occurs. Additionally, the helical protrusion 3776 controls the spray of the contents so that the aeration of the sample, production of bubbles, and splashing are minimized and do not disrupt the detection of the flash reaction.

Although container assemblies 1700, 2700, and 3700 are shown as including delivery paths that release fluid at the outlet of the pathway, in other embodiments, a housing and/or container assembly can include conduits extending through a delivery path to direct the flow of contents from a reagent volume and/or reagent container into the reaction chamber. For example, FIGS. 22 and 23 show a top perspective view and a cross-sectional view of a housing 4741 for use with any of the container assemblies described herein, such as the container assembly 2700 shown in FIGS. 7 and 8.

The housing 4741 defines a first reagent volume 4742 configured to receive a first reagent container 4780 (shown in FIG. 25) and a second reagent volume 4744 configured to receive a second reagent container 4790 (shown in FIG. 20). The housing 4741 includes a first puncturer 4792, a second puncturer 4794, a first delivery portion 4770, and a second delivery portion 4772. In some embodiments, the housing 4741, the first delivery portion 4770, the second delivery portion 4772, the first puncturer 4792, and/or the second puncturer 4794 can be monolithically constructed. In other embodiments, the housing 4741, the first delivery portion 4770, the second delivery portion 4772, the first puncturer 4792, and/or the second puncturer 4794 can be formed separately and then joined together. In addition, as shown, the first delivery portion 4770 defines a first delivery path 4771 in fluid communication with the first puncturer 4792. Similarly, the second delivery portion 4772 defines a second delivery path 4773 in fluid communication with the second puncturer 4794.

Figure 25:
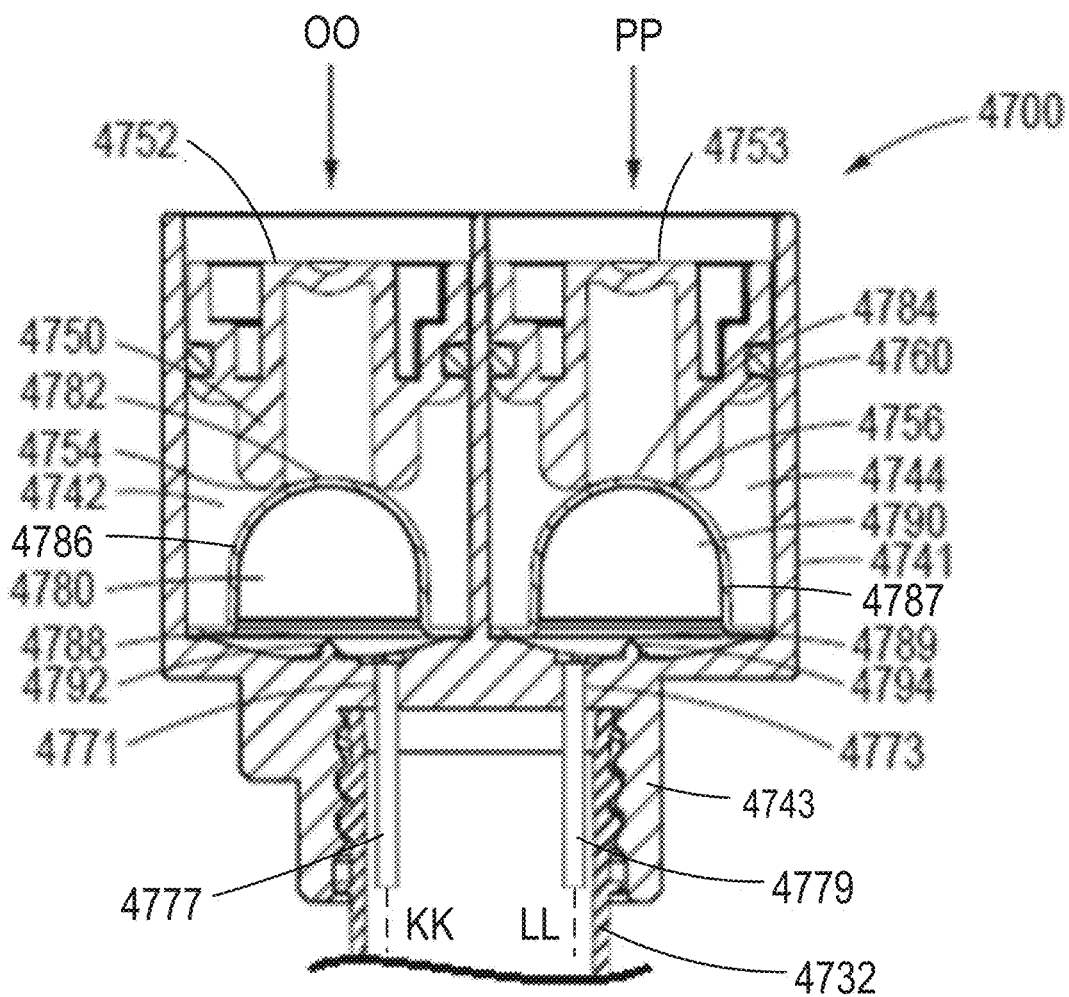
FIGS. 25 and 26 are cross-sectional views of a portion of the container assembly shown in FIGS. 22 and 23 in a first configuration and a second configuration, respectively.

The first puncturer 4792 and/or the second puncturer 4794 are configured to pierce (e.g., rupture) a first frangible portion 4788 (shown in FIG. 25) of the first reagent container 4780 and a second frangible portion 4789 (shown in FIG. 25) of the second reagent container 4790, respectively, to convey reagent from the first reagent container 4780 and/or the second reagent container 4790 into a reaction chamber 4732 (shown in FIG. 25). Thus, the first puncturer 4792 and the second puncturer 4794 include a sharp point, sharp edge and/or a protrusion, as shown, to pierce the first reagent container 4780 and the second reagent container 4790, respectively. Moreover, the first puncturer 4792 defines a first series of transfer pathways 4793 in fluid communication with the first reagent volume 4742, and the second puncturer 4794 defines a second series of transfer pathways 4795 in fluid communication with the second reagent volume 4744. In particular, each of the first series of transfer pathways 4793 and the second series of transfer pathways 4795 includes four channels spaced at approximately 90 degree intervals about the center point of the respective puncturer. Thus, as shown, the inclusion of the first series of transfer pathways 4793 and/or the second series of transfer pathways 4795 produces a discontinuous cross-sectional shape in the first puncturer 4792 and the second puncturer, respectively 4794. When the first puncturer 4792 pierces the first reagent container 4780, the first series of transfer pathways 4793 provides pathways through which the contents of the first reagent container 4780 can flow. Similarly, when the second puncturer 4794 pierces the second reagent container 4790, the second series of transfer pathways 4795 provides pathways through which the contents of the second reagent container 4790 can flow. Moreover, the arrangement of the first series of transfer pathways 4793, the second series of transfer pathways 4795, the cross-sectional shape of the first puncturer 4792, and/or the cross-sectional shape of the second puncturer 4794 can limit clogging or obstructions that may result from the piercing, thus providing a more repeatable delivery of the contents of the first reagent container 4780 and/or the second reagent container 4790. The first series of transfer pathways 4793 and the second series of transfer pathways 4795 are similar in design and function to the first series of transfer pathways 2793 and the second series of transfer pathways 2795 of the container assembly 2700 described above and will not be further described herein.

Figure 22:
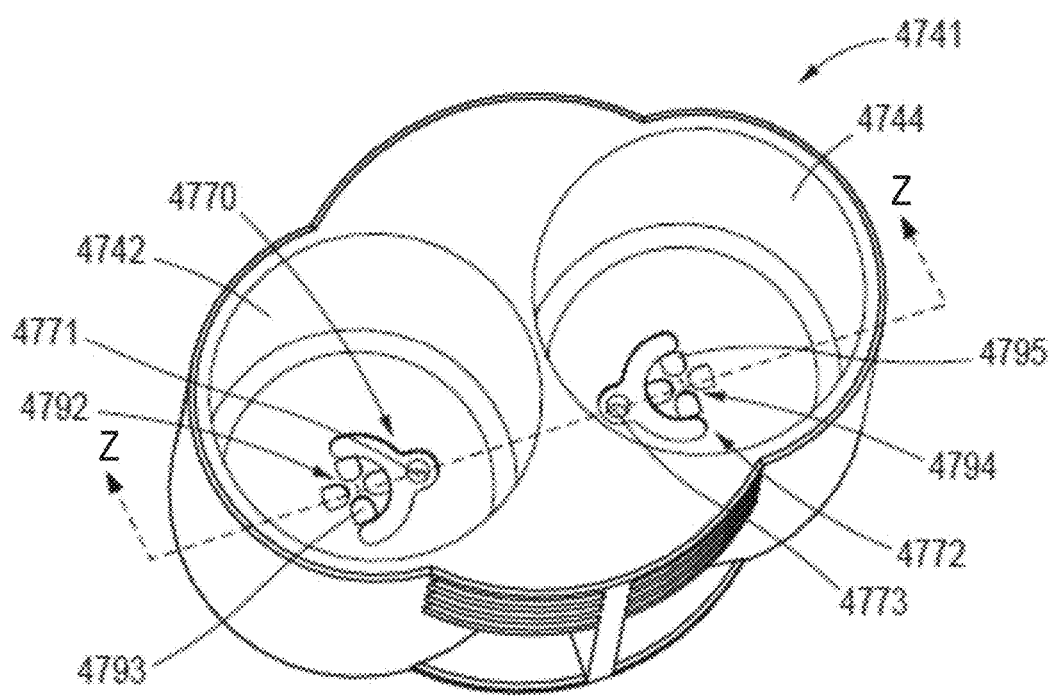
FIG. 22 is a top perspective view of a housing of a container assembly, according to an embodiment.
Figure 23:
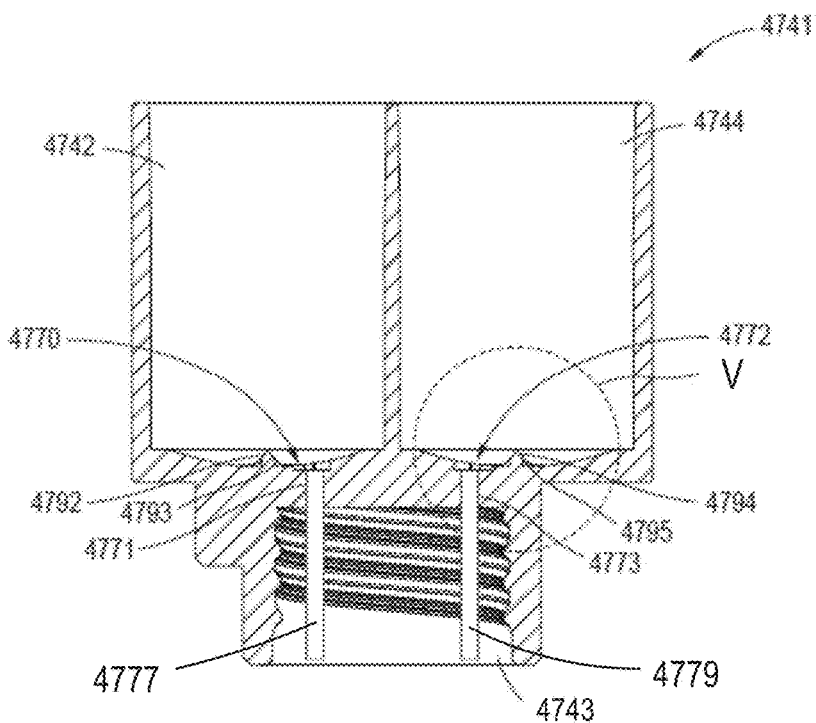
FIG. 23 is a cross-sectional view of the housing of the container assembly shown in FIG. 23, taken along line Z-Z in FIG. 23.
Figure 24:
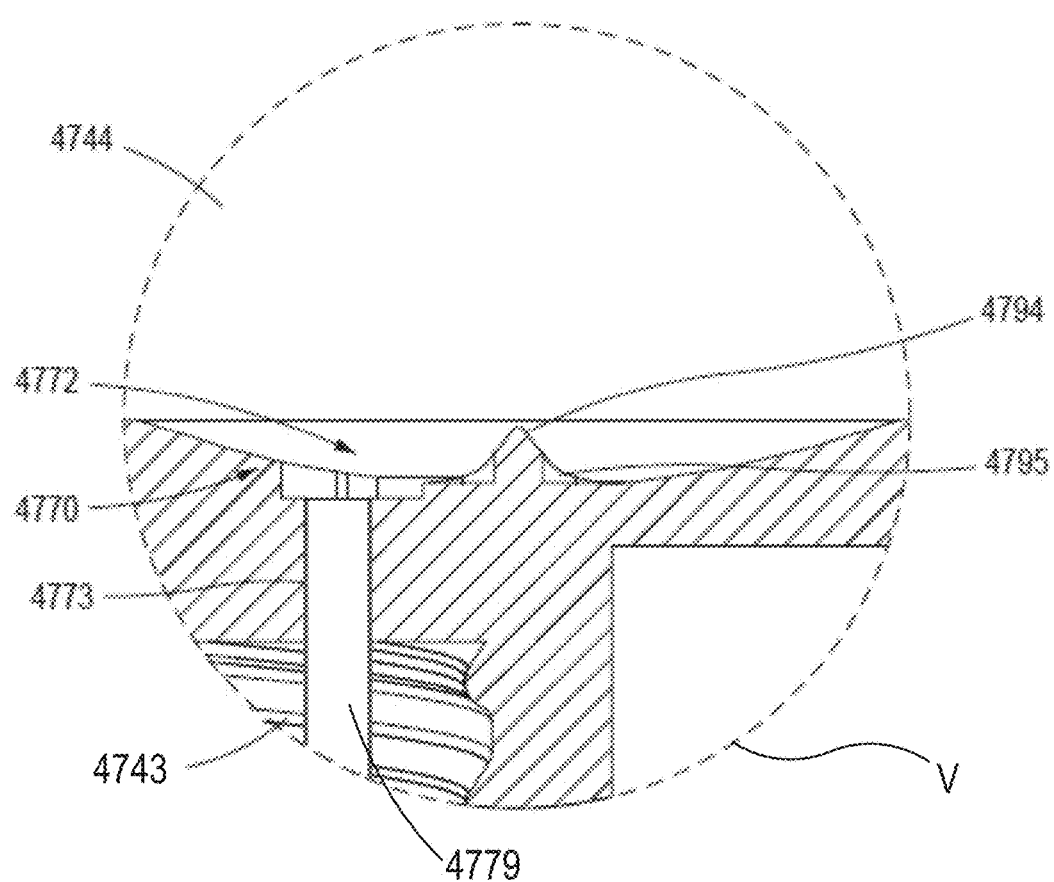
FIG. 24 is an enlarged view of the portion of the housing identified as region V in FIG. 23.

FIGS. 23 and 24 show a cross-sectional view taken along line Z-Z in FIG. 22 and a close-up cross-sectional view of the portion identified by region V in FIG. 23, respectively, of the housing 4741 shown in FIG. 22. As shown in FIG. 23, the housing 4741 includes a connection portion 4743 for connection between the housing 4741 and the reaction chamber 4732. The first delivery path 4771 includes a first conduit 4777 and the second delivery path 4773 includes a second conduit 4779. The first conduit 4777 and the second conduit 4779 extend distally into an interior volume of the connection portion 4743. The first conduit 4777 and the second conduit 4779 can be any suitable length. Although the first conduit 4777 and the second conduit 4779 are shown as extending only partially through the interior volume of the connection portion 4743, the first conduit 4777 and/or the second conduit 4779 can be formed to extend through the length of the interior volume of the connection portion 4743 or beyond the interior volume of the connection portion 4743. Additionally, although shown as being shaped as a cylinder, the first conduit 4777 and the second conduit 4779 can be any suitable shape, such as, for example, curved, helical, or having a triangular cross-section. The first conduit 4777 and the second conduit 4779 can be attached to the housing 4741 via any suitable method, such as, for example, via welding or adhesive. Similar to the protrusions 1776, 2776, 2778, and 3776 described above with reference to container assemblies 1700, 2700, and 3700, in some embodiments, the first conduit 4777 and the second conduit 4779 can include protrusions on an interior surface of the first conduit 4777 and the second conduit 4779.

As shown, the first delivery path 4771 is in fluid communication with the first series of transfer pathways 4793, the first reagent volume 4742, the first conduit 4777, and an inner volume of the connection portion 4743. Similarly, the second delivery path 4773 is in fluid communication with the second series of transfer pathways 4795, the second reagent volume 4744, the second conduit 4779, and the inner volume of the connection portion 4743. As such, the first series of transfer pathways 4793 and the second series of transfer pathways 4795 are configured to place the reaction chamber 4732 in fluid communication with the first delivery path 4771 and the second delivery path 4773, respectively, and the reagent volume 4742 and the reagent volume 4744, respectively. In this manner, the contents of the first reagent container 4780 can be conveyed from the first reagent container 4780 to the reaction chamber 4732 via the reagent volume 4742, the first series of transfer pathways 4793, and/or the first delivery path 4771. Similarly, the contents of the second reagent container 4790 can be conveyed from the second reagent container 4790 to the reaction chamber 4732 via the reagent volume 4744, the second series of transfer pathways 4795, and/or the second delivery path 4773.

Figure 26:
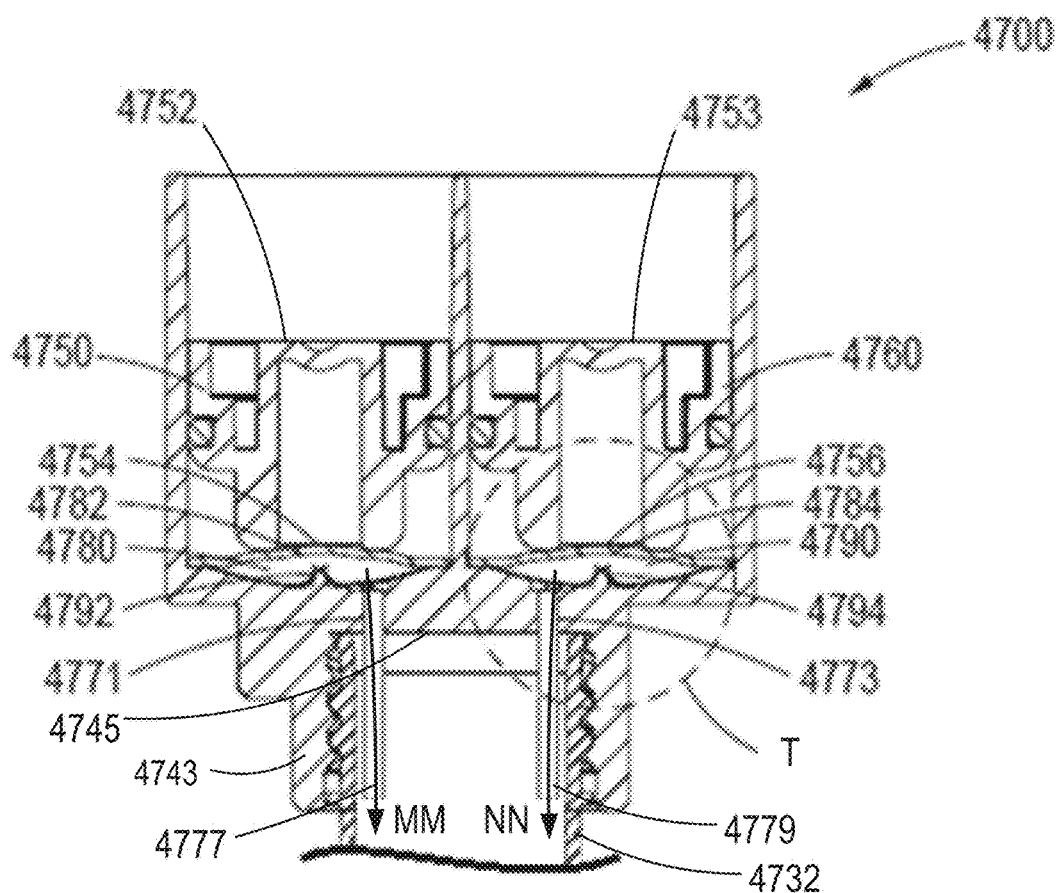

FIGS. 25 and 26 show a cross-sectional side view of a portion of the container assembly 4700 in a first configuration (FIG. 25) and a second configuration (FIG. 26), respectively. The container assembly 4700 can be used with and manipulated by any of the instruments and/or any of the components described herein (e.g., the instrument 2100) and in U.S. Patent Publication No. 2014/0272928, entitled "Systems and Methods for Detection of Cells using Engineered Transduction Particles" ("the '928 publication"), which is incorporated herein by reference in its entirety, and in International Patent Publication No. WO2015/164746, entitled "Reagent Cartridge and Methods for Detection of Cells," which is incorporated herein by reference in its entirety. In this manner, the container assembly 4700 and any of the container assemblies described herein can be used to detect and/or identify target cells (e.g., bacteria) within a sample according to any of the methods described herein or in the '928 publication. For example, in some embodiments, the container assembly 4700 can be used to dispose and/or mix a reagent into a sample while maintaining fluidic isolation between the container and an outside region. In this manner, the method of cell identification can be performed in a closed system and/or a homogeneous assay. Similarly stated, in some embodiments the container assembly 4700 is used in methods of cell identification and/or detection that do not involve removal of contents from the container assembly 4700, separation of the contents within the container assembly 4700, washing of the contents within the container assembly 4700 and/or rinsing of the contents within the container assembly 4700.

The container assembly 4700 includes the housing 4741, a first actuator 4750, a second actuator 4760, and the reaction chamber 4732. As described with reference to FIG. 23, the housing 4741 defines the first reagent volume 4742 configured to receive the first reagent container 4780 and the second reagent volume 4744 configured to receive the second reagent container 4790. The assembly of the housing 4741, the first actuator 4750, the first reagent container 4780, the second actuator 4760 and the second reagent container 4790 can be referred to as a "cap assembly" or "reagent assembly." The housing 4741 (and/or the cap assembly) is removably coupled to the reaction chamber 4732. For example, as shown in FIGS. 25 and 26, the housing 4741 can be threadedly coupled via the connection portion 4743 to a proximal portion of the reaction chamber 4732. In other embodiments, the housing 4741 and the reaction chamber 4732 can form an interference fit to couple the housing 4741 to the reaction chamber 4732. Thus, the housing 4741 (or cap assembly) can be stored separately from and/or spaced apart from the reaction chamber 4732. In this manner, a user can then dispose a sample into the reaction chamber 4732 in accordance with the methods described herein (and in the '928 publication, which is incorporated herein by reference in its entirety), and can then assemble the housing 4741 (or cap assembly) to the reaction chamber 4732 (or "tube") and complete the steps for cell identification, as described herein. The reaction chamber 4732 is similar in structure and function to the reaction chamber 2732 described with reference to the container assembly 2700 and will not be further described herein.

Figure 27:
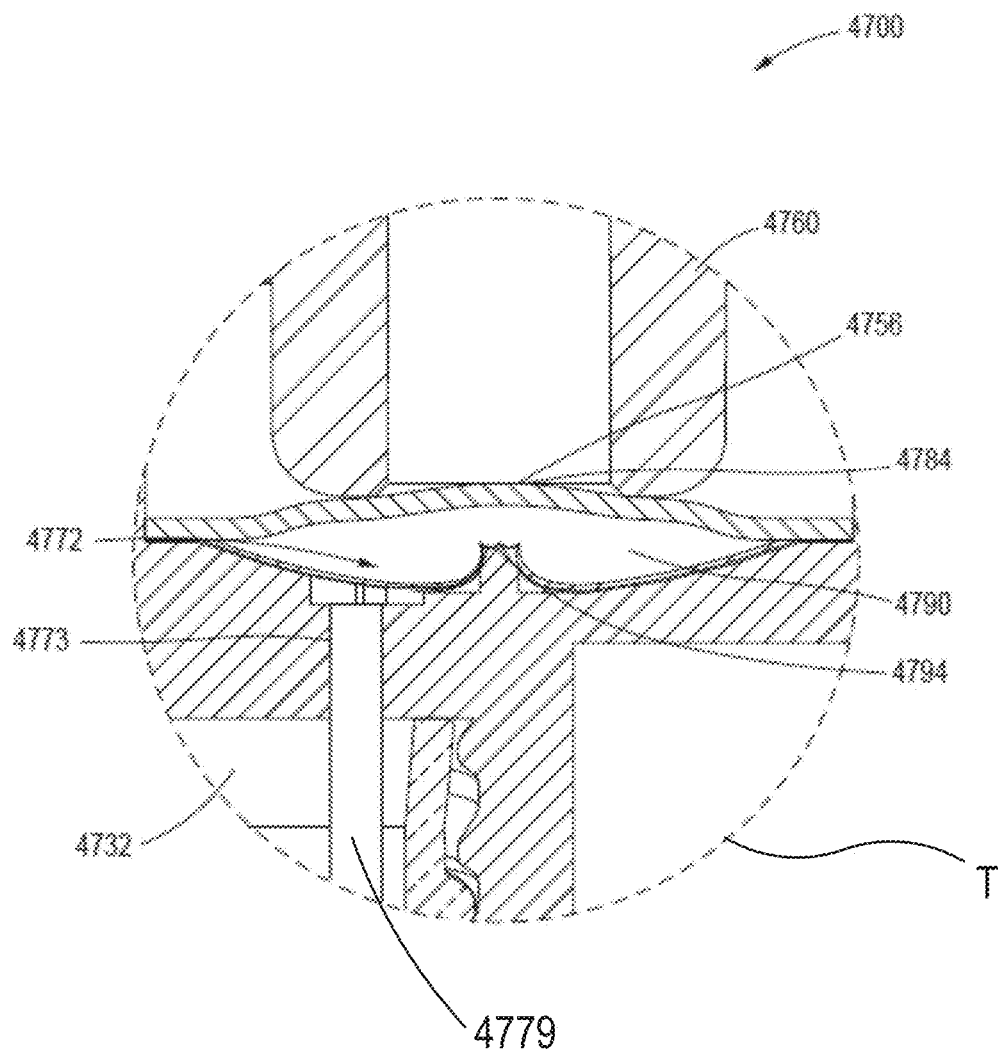
FIG. 27 is an enlarged view of the portion of the container assembly identified as region T in FIG. 26.

As shown in FIGS. 26 and 27, the first actuator 4750 has a first plunger portion 4754 disposed within the first reagent volume 4742, and a first engagement portion 4752. The second actuator 4760 has a second plunger portion 4756 disposed within the second reagent volume 4744, and a second engagement portion 4753. The first actuator 4750 and the second actuator 4760 are similar in structure and function to the first actuator 2750 and the second actuator 2760 described above with reference to container assembly 2700 and will not be further described herein. Additionally, it should be understood that any feature described with reference to the first actuator 4750 can also, or alternatively, apply to the second actuator 4760, and vice-versa.

The first engagement portion 4752 of the first actuator 4750 is configured to be manipulated to move the first plunger portion 4754 within the first reagent volume 4742 to deform the first reagent container 4780. The second engagement portion 4753 of the second actuator 4760 is configured to be manipulated to move the second plunger portion 4756 within the second reagent volume 4744 to deform the second reagent container 4790. In this manner, movement of the plunger portion 4754 can urge the frangible portion 4788 of the first reagent container 4780 against the puncturer 4792 to pierce and/or rupture the frangible portion 4788. Similarly, movement of the plunger portion 4756 can urge the frangible portion 4789 of the second reagent container 4790 against the puncturer 4794 to pierce and/or rupture the frangible portion 4789. The plunger portion 4754 of the actuator 4750 and a portion of the housing 4741 can collectively define a seal to fluidically and/or optically isolate the reagent volume 4742 from a volume outside of the housing 4741. Similarly, the plunger portion 4756 of the actuator 4760 and a portion of the housing 4741 can collectively define a seal to fluidically and/or optically isolate the reagent volume 4744 from a volume outside of the housing 4741.

As shown in FIGS. 25 and 26, the first reagent container 4780 has a sidewall 4786 and a frangible portion 4788 (referred to as a "first frangible portion"), which together define an internal volume. The internal volume can be completely or partially filled with a reagent and/or substance, as described herein. In addition, the first reagent container 4780 has a contact portion 4782 (referred to as a "first contact portion"). The second reagent container 4790 has a sidewall 4787 and a frangible portion 4789 (referred to as a "second frangible portion"). In addition, the second reagent container 4790 has a contact portion 4784 (referred to as a "second contact portion"). The first reagent container 4780 and the second reagent container 4790 are similar in structure and function to the first reagent container 2780 and the second reagent container 2790 described above with reference to container assembly 2700 and will not be further described herein. Additionally, it should be noted that any feature described with reference to the first reagent container 4780 can also, or alternatively, apply to second reagent container 4790 and vice-versa.

As shown in FIG. 25, the container assembly 4700 is in a first configuration. In the first configuration, the first actuator 4750 and the second actuator 4760 are positioned such that the first reagent container 4780 and the second reagent container 4790 disposed within the housing 4741 are substantially undeformed. Similarly stated, the first actuator 4750 and the second actuator 4760 are positioned such that they do not cause puncturer 4752 and puncturer 4794 to pierce the first reagent container 4780 and the second reagent container 4790, respectively. Thus, the container assembly 4700 is in a "ready" state when in the first configuration. In some embodiments, the container assembly 4700 can include a safety mechanism (not shown) to prevent and/or limit movement of the first actuator 4750 and/or the second actuator 4760 relative to the housing 4741 until desired by the operator.

To actuate the container assembly 4700, a force is applied to the engagement portion 4752 of the first actuator 4750, and a force is applied to the engagement portion 4753 of the actuator 4760, thus causing the first actuator 4750 and the second actuator 4760 to move as shown by the arrows OO and PP, respectively, in FIG. 25. The forces can be applied by any suitable instrument, such as the instrument 2100 described above, and those shown and described in the '928 publication. The forces can be applied substantially simultaneously or at different times, in accordance with the desired assay.

More particularly, the first actuator 4750 is manipulated (e.g., at the first engagement portion 4752) to move the first plunger portion 4754 within the housing 4741 such that the first plunger portion 4754 engages the contact portion 4782 of the first reagent container 4780 to partially deform the first reagent container 4780 from the first configuration to the second configuration. As the first plunger portion 4754 engages the first reagent container 4780, the first puncturer 4792 pierces a portion of the first reagent container 4780 (e.g., the frangible portion 4788) to convey reagent from the first reagent container 4780 into the first reagent volume 4742, the first delivery portion 4770, the first conduit 4777, and/or the reaction chamber 4732. Similarly, the second actuator 4760 is manipulated (e.g., at the second engagement portion 4753) to move the second plunger portion 4756 within the housing 4741 such that the second plunger portion 4756 engages the second contact portion 4784 of the second reagent container 4790 to partially deform the second reagent container 4790 from the first configuration to the second configuration. As the second plunger portion 4756 engages the second reagent container 4790, the second puncturer 4794 pierces a portion of the second reagent container 4790 (e.g., the frangible portion 4789) to convey reagent from the second reagent container 4790 into the second reagent volume 4744, the second delivery portion 4772, the second conduit 4779, and/or the reaction chamber 4732.

As shown in FIG. 26, and in greater detail in FIG. 27, which shows the region T indicated in FIG. 21, the container assembly 4700 is in a second configuration. In the second configuration, the first actuator 4750 and the second actuator 4760 are positioned such that the first reagent container 4780 and the second reagent container 4790 are substantially deformed and/or collapsed. Similarly stated, the first actuator 4750 and the second actuator 4760 are positioned such that at least portions of the respective forces are transferred to the first reagent container 4780 and the second reagent container 4790, respectively. In such a configuration, as shown, the first puncturer 4792 has pierced the first reagent container 4780 such that a desired amount of the contents of the first reagent container 4780 have substantially exited the first reagent container 4780, and entered the first delivery portion 4770, the first conduit 4777, and/or the reaction chamber 4732, as shown by the arrow MM. Similarly, the second puncturer 4794 has pierced the second reagent container 4790 such that a desired amount of the contents of the second reagent container 4790 have substantially exited the second reagent container 4790, and entered the second delivery portion 4772, the second conduit 4779, and/or the reaction chamber 4732, as shown by the arrow NN.

When the first reagent container 4780 and/or the second reagent container 4790 are deformed, a desired amount of its contents are conveyed into the reaction chamber 4732 in a manner such that "dead volume" is limited and/or substantially eliminated. As used herein the "dead volume" is the volume of reagent that is dispensed from the first reagent container 4780 and/or the second reagent container 4790 but that is not conveyed into reaction chamber 4732. The dead volume can include, for example, the volume of the delivery paths and the transfer pathways. In some embodiments, the first reagent container 4780 and/or the second reagent container 4790 can be configured to limit the dead volume therein when the assembly 4700 is actuated. For example, in some embodiments, the contact portion 4782 and/or the contact portion 4784 can be configured, along with the corresponding engagement portions of the actuator 4750 and actuator 4760, respectively, to deform in a controlled manner that reduces the dead volume. In this manner, the first reagent container 4780 and/or the second reagent container 4790 can be configured to promote a consistent and/or repeatable dispensation of their contents (e.g., reagents).

In some embodiments, the cap assembly (i.e., the first reagent container 4780 and/or the second reagent container 4790 along with their respective plungers and portions of the housing) is configured such that the "dead volume" is between about 30 µL and about 50 µL. In some embodiments, the cap assembly is configured such that the "dead volume" about 40 µL±9 µL. By limiting the part-to-part variation in the dead volume, the accuracy of reagent delivery, and thus, the accuracy of the assay, can be improved. In some embodiments, for example, the cap assembly is configured such that the dispensed volume is about 285 µL with a coefficient of variation of about three percent.

Moreover, the first conduit 4777 and the second conduit 4779 control the behavior of the contents of the first reagent container 4780, the second reagent container 4790, the first reaction volume 4742, and/or the second reaction volume 4744 as the contents travel through the first delivery portion 4770 and/or the second delivery portion 4772 and into the reaction chamber 4732. As the contents are delivered from the first conduit 4777 and/or the second conduit 4779, the first conduit 4777 and/or the second conduit 4779 control the behavior of the contents such that the contents exit first conduit 4777 and/or the second conduit 4779 in controlled plumes. The first conduit 4777 and the second conduit 4779 each define an exit axes (the axis KK and the axis LL, respectively) that extends toward the portion of the reaction chamber 4732 containing the sample, e.g., the bottom of the reaction chamber 4732, as shown in FIG. 20. In this way, the first conduit 4777 and the second conduit 4779 direct the contents distally toward a sample in the reaction chamber 4732, reducing attachment of the contents to the walls of the reaction chamber 4732. Additionally, by distancing the distal end openings of the first conduit 4777 and the second conduit 4779 from a proximal wall 4745 (shown in FIG. 26), the behavior of the contents will be less likely to be influenced by pressure gradients that may exist near the proximal wall 4745 and cause uncontrolled spray of the contents in the reaction chamber 4732. Thus, the first conduit 4777 and/or the second conduit 4779 control the behavior of the contents such that a substantially repeatable flash reaction occurs when reporter molecules are present, even at low signal levels. In other words, the first conduit 4777 and/or the second conduit 4779 cause the flow of contents to be directed toward the sample and control the spray such that even if there are a small number of reporter molecules in the sample, the reagent and/or the substrate will mix with the sample quickly enough that a detectable flash reaction occurs. Additionally, the first conduit 4777 and/or the second conduit 4779 also reduce the distance that the contents travel in unconstrained, free space within the reaction chamber 4732 so that the aeration of the sample, production of bubbles, and splashing are minimized and do not disrupt the detection of the flash reaction. As such, turbulence, splash, the production of bubbles, aeration, and/or the like, of the contents can be limited, and subsequent optical readings can be more accurate than if the sample contains such bubbles, aeration or the like. Thus, in use, the contents from first reagent container 4780, the second reagent container 4790, the first reaction volume 4742, and/or the second reaction volume 4744 can flow from first conduit 4777 and/or the second conduit 4779, respectively, to the sample and produce a repeatable, detectable flash reaction.

Figure 28:
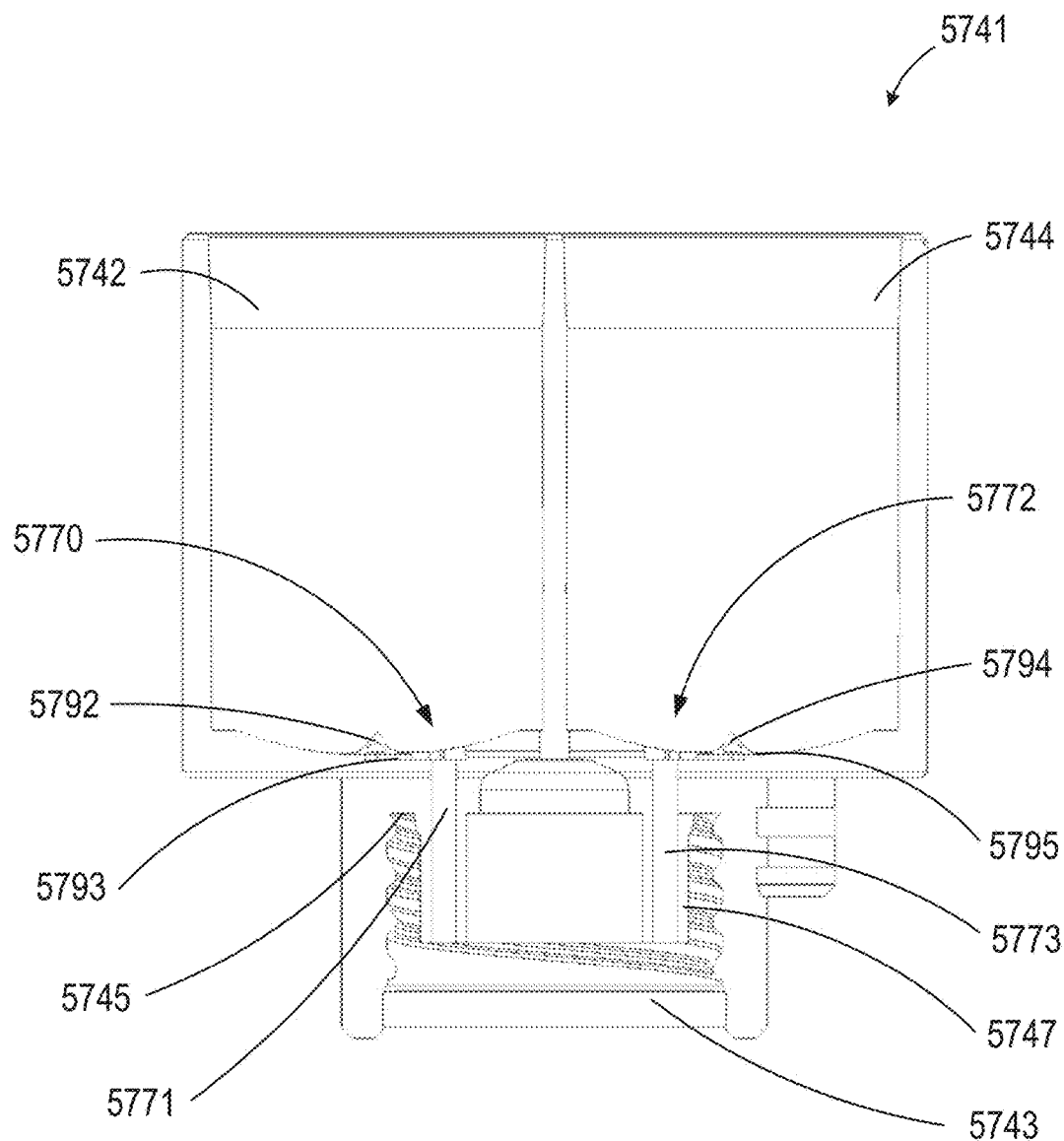
FIG. 28 is a cross-sectional view of a housing of a container assembly, according to an embodiment.
Figure 29:
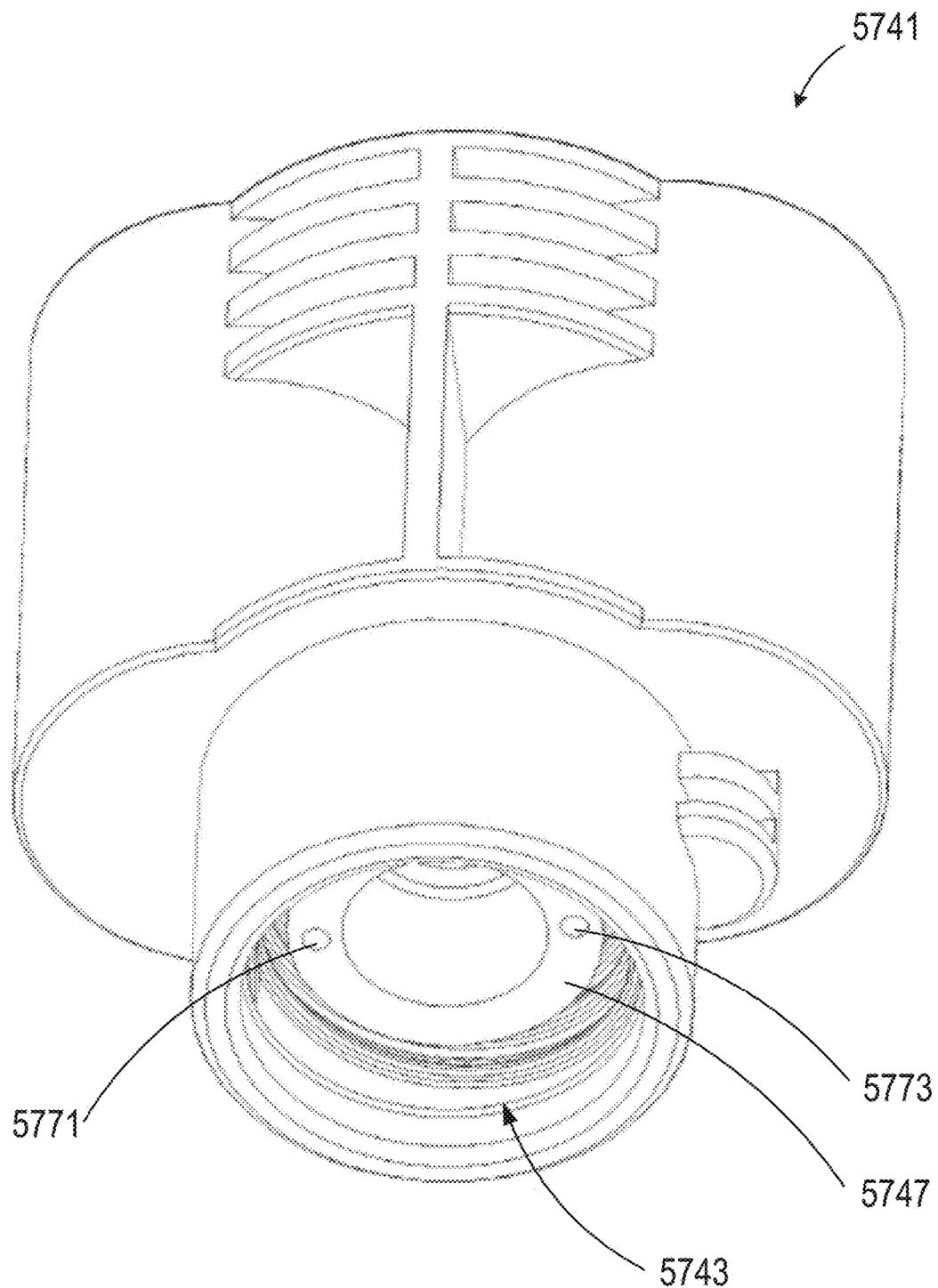
FIG. 29 is a bottom perspective view of the housing of the container assembly shown in FIG. 28.
Figure 30:
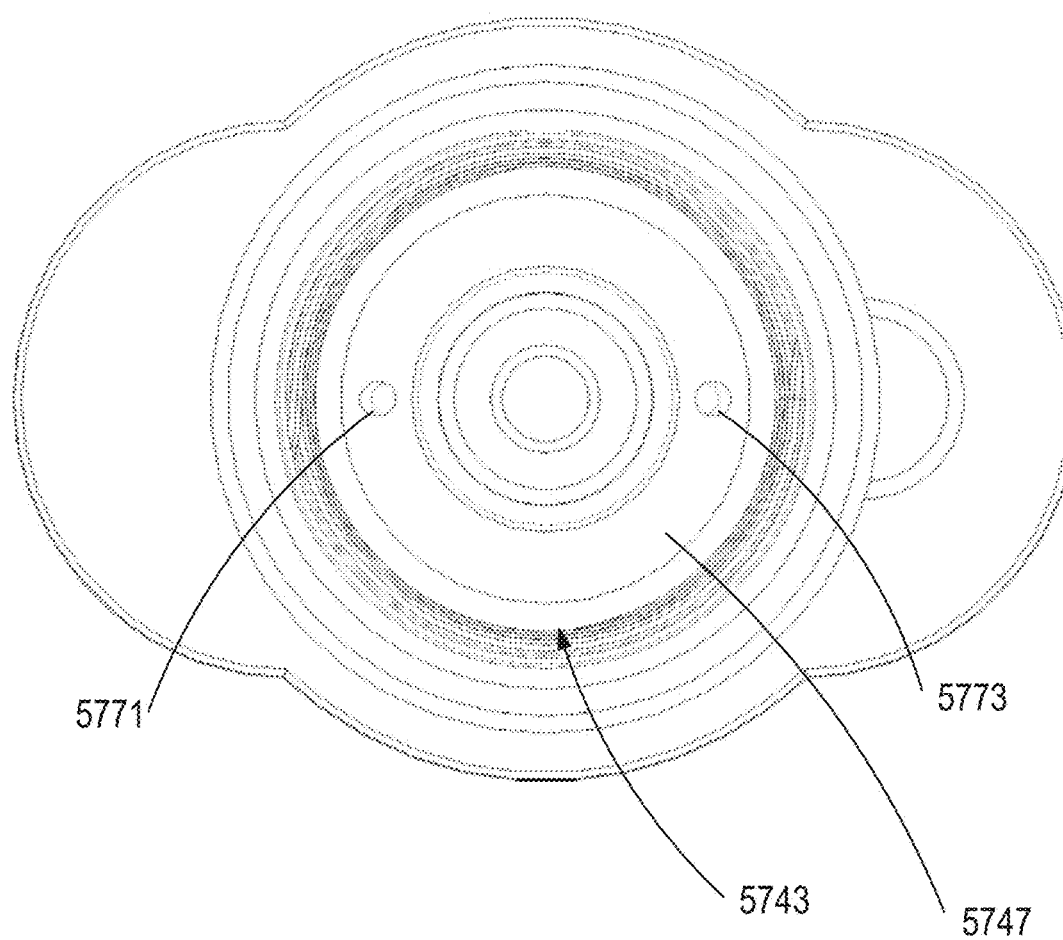
FIG. 30 is a bottom view of the housing of the container assembly shown in FIGS. 28 and 29.

Although the housing 4741 delivers fluid through the first conduit 4777 and/or the second conduit 4779, which are shown as extending from the first delivery path 4771 and the second delivery path 4773 as separate cylindrical tubes, the housing 4741 can alternatively include an interior cylindrical projection that defines a first delivery path and a second delivery path. For example, FIGS. 28-30 show a cross-sectional view, a bottom perspective view, and a bottom view of a housing 5741 for use with any of the container assemblies described herein, such as the container assembly 2700 shown in FIGS. 7 and 8.

The housing 5741 defines a first reagent volume 5742 configured to receive a first reagent container (not shown) and a second reagent volume 5744 configured to receive a second reagent container (not shown). The housing 5741 includes a first puncturer 5792, a second puncturer 5794, a first delivery portion 5770, and a second delivery portion 5772. The housing 5741 also includes a connection portion 5743 and an interior cylindrical projection 5747. The connection portion 5743 can be removably coupled to a reaction chamber (not shown). For example, in some embodiments, the connection portion 5743 can be threadedly coupled to the reaction chamber. In other embodiments, the connection portion 5743 and the reaction chamber can form an interference fit to couple the housing connection portion 5743 to the reaction chamber. In some embodiments, the housing 5741, the first delivery portion 5770, the second delivery portion 5772, the first puncturer 5792, the second puncturer 5794, the connection portion 5743, and/or the interior cylindrical projection 5747 can be monolithically constructed. In other embodiments, the housing 5741, the first delivery portion 5770, the second delivery portion 5772, the first puncturer 5792, the second puncturer 5794, the connection portion 5743, and/or the interior cylindrical projection 5747 can be formed separately and then joined together. In addition, as shown, the first delivery portion 5770 defines a first delivery path 5771 in fluid communication with the first puncturer 5792. Similarly, the second delivery portion 5772 defines a second delivery path 5773 in fluid communication with the second puncturer 5794. The first delivery path 5771 and the second delivery path 5773 are defined by the interior cylindrical projection 5747 of the housing 5741.

The first puncturer 5792 and/or the second puncturer 5794 are configured to pierce (e.g., rupture) a first frangible portion of the first reagent container and a second frangible portion of the second reagent container, respectively, to convey reagent from the first reagent container and/or the second reagent container into a reaction chamber (not shown). The first reagent container and/or the second reagent container can be similar in structure and function to any of the reagent containers described above and will not be further described herein. Additionally, the reaction chamber can be similar in structure and function to any of the reaction chambers described above and will not be further described herein. The first puncturer 5792 and the second puncturer 5794 include a sharp point, sharp edge and/or a protrusion, as shown, to pierce the first reagent container and the second reagent container, respectively. Moreover, the first puncturer 5792 defines a first series of transfer pathways 5793 in fluid communication with the first reagent volume 5742, and the second puncturer 5794 defines a second series of transfer pathways 5795 in fluid communication with the second reagent volume 5744. The first series of transfer pathways 5793 and the second series of transfer pathways 5795 can be similar in structure and function to any of the first series of transfer pathways and/or the second series of transfer pathways described above and will not be further described herein.

As shown, the first delivery path 5771 is in fluid communication with the first series of transfer pathways 5793, the first reagent volume 5742, and the inner volume of the connection portion 5743. Similarly, the second delivery path 5773 is in fluid communication with the second series of transfer pathways 5795, the second reagent volume 5744, and the inner volume of the connection portion 5743. In a configuration where the housing 5741 is coupled to a reaction chamber, the first series of transfer pathways 5793 and the second series of transfer pathways 5795 are configured to place the reagent volume 5742 and the reagent volume 5744, respectively, in fluid communication with the first delivery path 5771 and the second delivery path 5773, respectively, and the reaction chamber. In this manner, the contents of the reagent container 5780 can be conveyed from the reagent container 5780 to the reaction chamber via the reagent volume 5742, the first series of transfer pathways 5793, and/or the first delivery path 5771. Similarly, the contents of the reagent container 5790 can be conveyed from the reagent container 5790 to the reaction chamber via the reagent volume 5744, the second series of transfer pathways 5795, and/or the second delivery path 5773.

Moreover, the first delivery path 5771 and the second delivery path 5773 control the behavior of fluid flow between the first reagent volume 5742 and the reaction chamber and the second reagent volume 5744 and the reaction chamber, respectively. In other words, the first delivery path 5771 and the second delivery path 5773 control the behavior of the contents of the first reagent container, the second reagent container, the first reaction volume 5742, and/or the second reaction volume 5744 as the contents travel through the first delivery portion 5770 and/or the second delivery portion 5772 and into the reaction chamber. As the contents are delivered from the fir first delivery path 5771 and/or the second delivery path 5773, the first delivery path 5771 and/or the second delivery path 5773 control the behavior of the contents such that the contents exit the first delivery path 5771 and/or the second delivery path 5773 in controlled plumes. The first delivery path 5771 and the second delivery path 5773 direct the contents distally toward the portion of the reaction chamber containing the sample, e.g., the bottom of the reaction chamber, reducing attachment of the contents to the walls of the reaction chamber. Additionally, by distancing the distal end openings of the first delivery path 5771 and the second delivery path 5773 from a proximal wall 5745 (shown in FIG. 23), the behavior of the contents will be less likely to be influenced by pressure gradients that may exist near the proximal wall 5745 and cause uncontrolled spray of the contents in the reaction chamber. Thus, the first delivery path 5771 and/or the second delivery path 5773 control the behavior of the contents such that a substantially repeatable flash reaction occurs when reporter molecules are present, even at low signal levels. In other words, the first delivery path 5771 and/or the second delivery path 5773 cause the flow of contents to be directed toward the sample and control the spray such that even if there are a small number of reporter molecules in the sample, the reagent and/or the substrate will mix with the sample quickly enough that a detectable flash reaction occurs. Additionally, the first delivery path 5771 and/or the second delivery path 5773 also reduce the distance that the contents travel in unconstrained, free space within the reaction chamber so that the aeration of the sample, production of bubbles, and splashing are minimized and do not disrupt the detection of the flash reaction. As such, turbulence, splash, the production of bubbles, aeration, and/or the like, of the contents can be limited, and subsequent optical readings can be more accurate than if the sample contains such bubbles, aeration or the like. Thus, in use, the contents from first reagent container, the second reagent container, the first reaction volume 5742, and/or the second reaction volume 5744 can flow from first delivery path 5771 and the second delivery path 5773, respectively, to the sample and produce a repeatable, detectable flash reaction.

Analysis of the Rate of Delivery of the Substrate

In use, the container assemblies described above, including the container assembly 1700, the container assembly 2700, the container assembly 3700, the container assembly 4700 and the container assembly 5700, can employ, in some embodiments, a bacterial luciferase reporter transduction particle. These reporters cause the expression of a bacterial luciferase such as that from the organism *A. fischeri*. Bacterial luciferase is comprised of the luxA and luxB genes encoding LuxA and LuxB proteins that combine to form the active luciferase enzyme. LuxAB catalyzes a luminescent reaction in the presence of oxygen, reduced flavin mononucleotide (FMNH2, supplied by the host cell), and an aldehyde such as tridecanal (supplied exogenously and which readily penetrates into viable bacterial cells).

Accordingly, during such methods or assays, bacterial luciferase is expressed and the luciferase molecules complex FMNH2 molecules. These complexes accumulate and when an aldehyde is added, the luminescence reaction proceeds. Ideally, it is preferable that all complexed luciferases are triggered to emit photons simultaneously. In this manner, a large flux of photons is emitted in a short period of time— i.e., a flash of light is produced that can be readily detected, especially when there is a low load of target cells. It is understood that if the complexed luciferases emit light in an un-synchronized manner, the photons are emitted over an extended period of time thereby not producing a flash.

Because the light emission kinetics are mediated by the availability of aldehyde (i.e., the substrate), under ideal conditions it is desirable to deliver the aldehyde instantaneously to an entire volume of a reaction. Injecting aldehyde into the reaction at a rapid speed can approach this ideal situation. Therefore, faster injection speeds result in more optimal flash reactions. Indeed, a study (identified as the 2014 TEST) that examined the effect of injection speed of the aldehyde on light output found that increasing injection speed resulted in greater light output when measuring the peak value of light production. At a certain point, however, an increase in injection speed was found to result in lower light output and/or greater variability in the results. This phenomenon is possibly attributed to splashing and bubble formation in the reaction that serves to perturb or disrupt the detection of the light produced. Therefore, a desired range of injection speed (expressed as the speed of the actuator) was found where maximal light output is attained. The testing for the 2014 TEST was performed on prototype components and included a container assembly having an actuator (similar to the actuator 2760 shown herein) that was actuated in a similar manner to how actuation would occur within a representative instrument. Specifically, the prototype actuator was actuated by a stepper motor, and was moved at various different speed set points to determine the effect of dispensation time, dispensation flow rate, and actuator speed on the detection performance.

Figure 31:
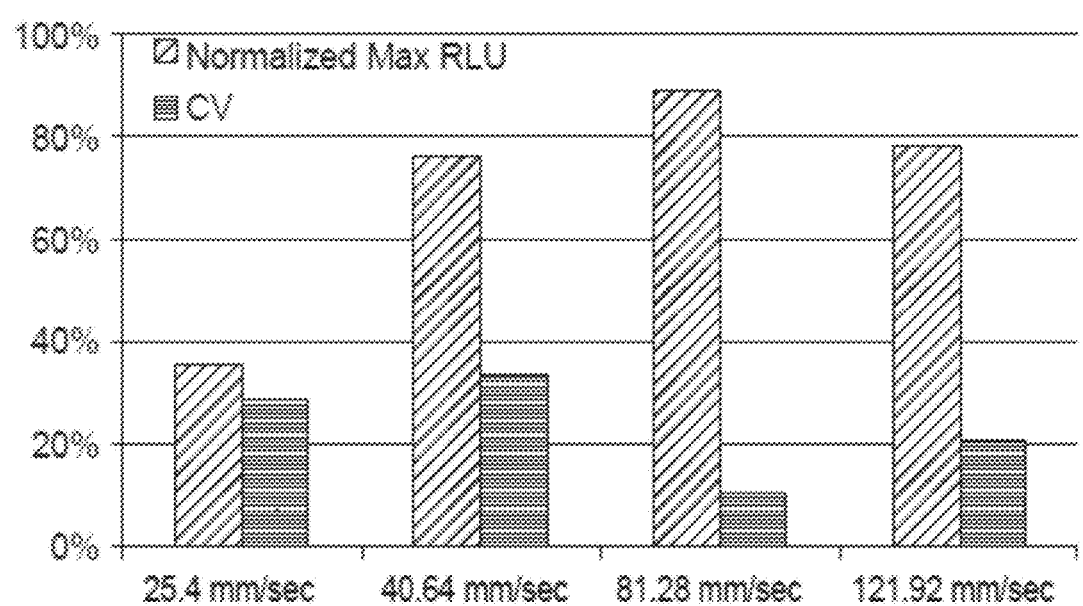
FIG. 31 is a bar chart showing the signal output for a series of different actuator speeds, which correspond to different reagent velocities.

The test results for the 2014 TEST are summarized in FIG. 31, which is a bar chart showing the average maximum signal output (i.e., Relative Light Units, or RLU) obtained from luciferase expressing cells after injecting aldehyde at varying actuator speed set points (i.e., the downward speed of the actuator). The speeds are presented as the speed set point (or commanded speed) provided to the stepper motor. Thus, for example, the speed set point of 81.28 mm/sec is based on an input command to move the stepper motor at 3,200 steps per second, where one step is 0.0254 mm. Note that the RLU values are expressed as a percentage or the maximum RLU value obtained in this study.

As shown, an optimum RLU output for the 2014 TEST was observed at 3,200 steps/sec where the RLU values were maximum and the variability in light output (expressed as a coefficient of variation) was at a minimum. Further testing identified an optimal range, for some assays, of between about 2,500 steps/sec (63.5 mm/sec) and about 3,200 steps/sec (81.3 mm/sec). Thus, in some embodiments, the substrate is mixed by moving the actuator linearly at a rate of about 2,850 steps/sec (72.4 mm/sec). The 2014 TEST confirms that there is a region of actuator speed (which is related to the dispensation time and the flow rate of reagent dispensed) at which the optimum RLU output will occur. Similarly stated, detection performance is diminished if the reagent is dispensed either too slowly or too quickly.

Figure 32:
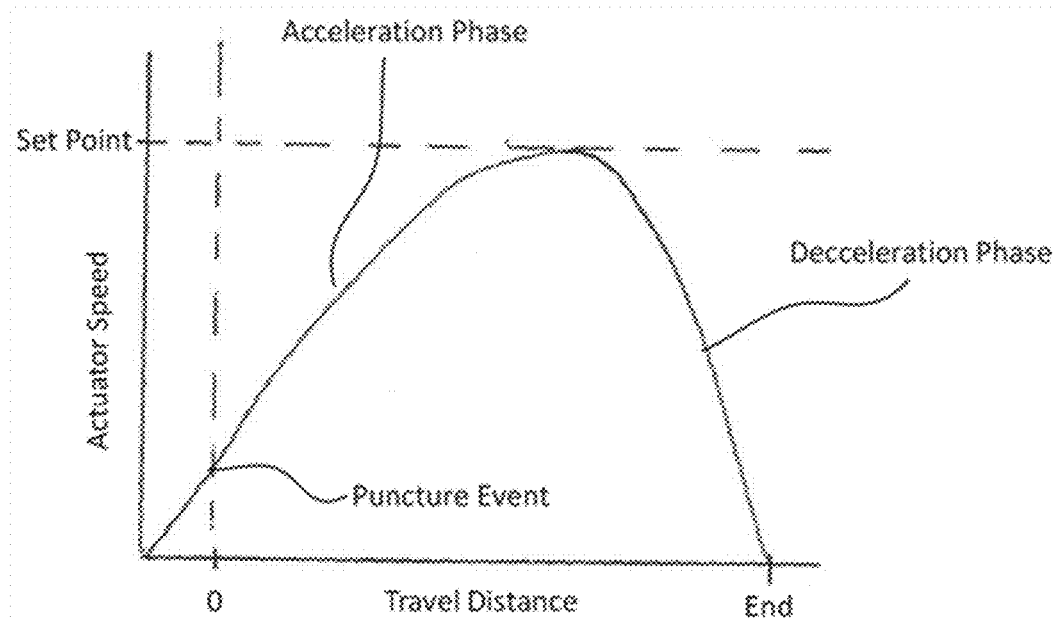
FIG. 32 is a plot showing a sample profile of actuator speed as a function of actuator travel distance.

Upon further evaluation of the equipment used in the 2014 TEST, however, it was speculated that the stepper motor did not move at the set points provided. Thus, even though the set point was for a particular actuator speed (for example, 81.28 mm/sec), it was speculated that the stepper motor was actually moving at a slower speed, possibly due to the load imparted on the stepper motor during the test. Moreover, it was speculated that the actual speed of the actuator varied over the duration of movement, and thus the actuator traveled at a near-constant speed for only a small portion of the travel duration. This is shown conceptually in FIG. 32, which is an illustrative plot of the actuator speed (y-axis) as a function of the actuator travel distance (x-axis). Note that the plot in FIG. 32 is not actual data, but rather is presented to illustrate possible behavior of the actuator during the 2014 TEST. As shown in FIG. 32, it was speculated that the profile of actuator movement included a lengthy acceleration phase followed by a lengthy deceleration phase. With such an actuator movement profile, the puncture event (i.e., the puncturing of the reagent container, similar to the reagent container 2790) occurs when the actuator is moving more slowly (i.e., during its acceleration phase), and thus does not occur as rapidly as when the puncture event occurs at higher actuator speeds.

Figure 33:
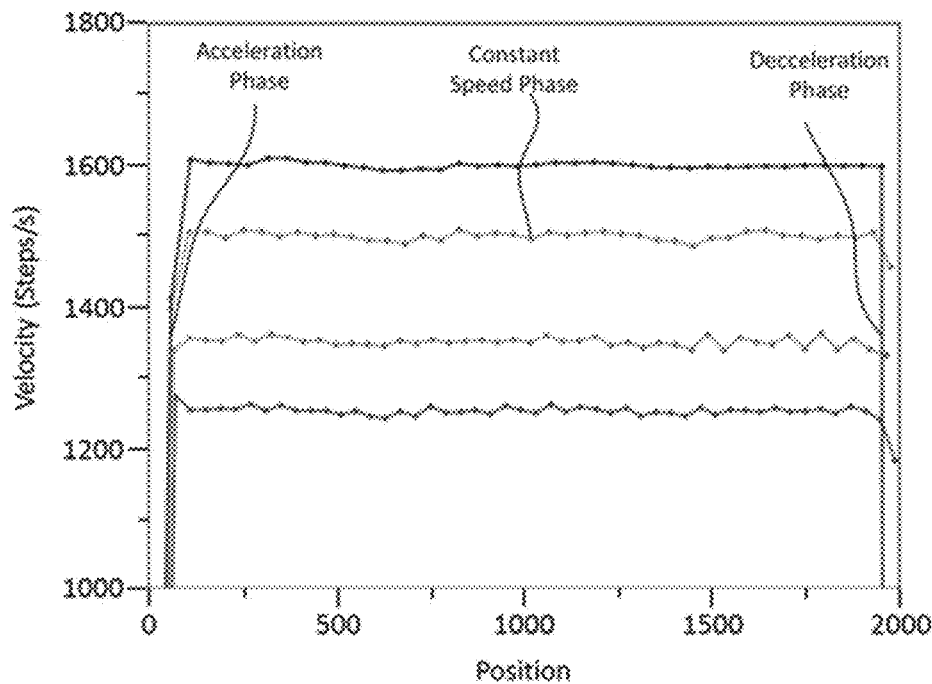
FIG. 33 is a plot of actuator speed data as a function of the actuator position during a dispensation event.

In view of the speculation surrounding the 2014 TEST, additional tests were conducted to determine the desired range of actuator speeds, reagent dispensation times and/or the flow rate of reagent during the dispensation operation. Specifically, a second study (identified as the 2015 TEST) was conducted to examine the effect of injection speed of the aldehyde on light output for three different reagent modules. The reagent modules tested included a "standard" reagent module (i.e., a reagent module devoid of protrusions within the delivery path; identified as the "0.025" regular" module), a reagent module similar to the reagent module 2710 (identified as the "0.030 fluted" module), and a reagent module similar in design to the reagent module 4710 (i.e., a reagent module having a conduit similar to the first conduit 4777 that extends the delivery path; identified as the "0.025" extended" module). Moreover, during the 2015 TEST the actual speed of the stepper motor used to actuate the actuator of the reagent module was measured via a shaft encoder on the stepper motor. Thus, the actual movement of the actuator during the tests was known. Specifically, FIG. 33 shows a plot of the actuator speed in (measured in the number of motor steps per second; y-axis) as a function of the actuator travel distance (measured in the total number of motor steps; x-axis). As shown in FIG. 33, the profile of actuator movement included very short acceleration phase followed by a lengthy constant velocity phase, concluding with a very short deceleration phase. With such an actuator movement profile, the puncture event (i.e., the puncturing of the reagent container, similar to the reagent container 2790) likely occurs when the actuator is moving consistently and rapidly (i.e., during the constant velocity phase).

Figures 34, 35:
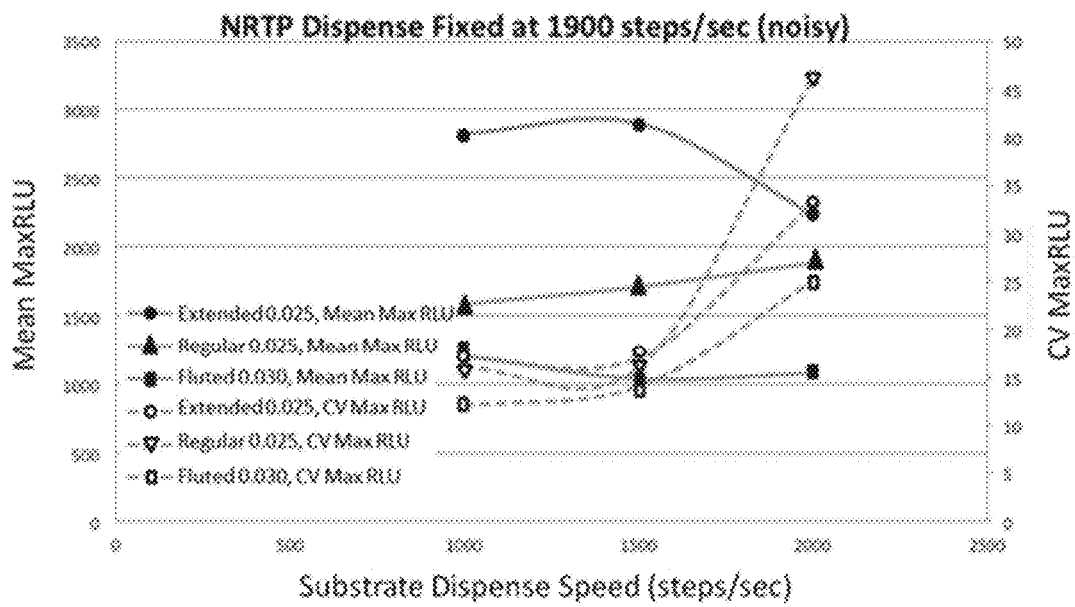
FIGS. 34 and 35 are line plots showing the signal output and coefficient of variation for a series of different reagent modules as a function of the actuator speed.

The 2015 TEST included evaluating the effect of the reagent (i.e., aldehyde) dispensation speed on the average maximum signal output (i.e., Relative Light Units, or RLU), as well as the coefficient of variation (CV) for the three different reagent modules identified above. The testing also included evaluating the dispensation speed of the transduction particles contained in the first reagent container (e.g., similar to the reagent container 2780) to determine the effects of the earlier mixing of the transduction particles on the performance of the optical detection operation. Generally, the desired performance occurs within the region where the RLU signal is maximized and the CV signal is minimized. FIGS. 34 and 35 show plots of the RLU obtained from luciferase expressing cells after injecting aldehyde at varying actuator speeds for each of the three reagent modules tested. FIGS. 34 and 35 also include the CV for each reagent module, shown in the dashed lines. FIG. 34 is data for an assay in which the transduction particle dispensation occurred at a speed of 1900 steps per second, and FIG. 35 is data for an assay in which the transduction particle dispensation occurred at a speed of 2400 steps per second.

As shown, increasing the actuator speed can produce higher RLU (see, e.g., FIG. 35 showing a peak output for the 0.030" fluted module. Increasing the actuator speed beyond about 1500 steps per second, however, was shown to potentially have diminishing returns for the RLU values, but generally higher CV. Thus, the 2015 TEST identified an optimal range, for some assays, of between about 30 mm/sec (about 1200 steps per second) and about 50 mm/sec (about 1970 steps per second), and particularly at a rate of about 38 mm/sec (1500 steps per second). As described herein, the delivery volume of reagent (e.g., substrate) can be about 0.3 ml, thus the flow rate of delivery for such assays can be between about 1.1 ml/sec and about 1.5 ml/sec.

Figure 36:
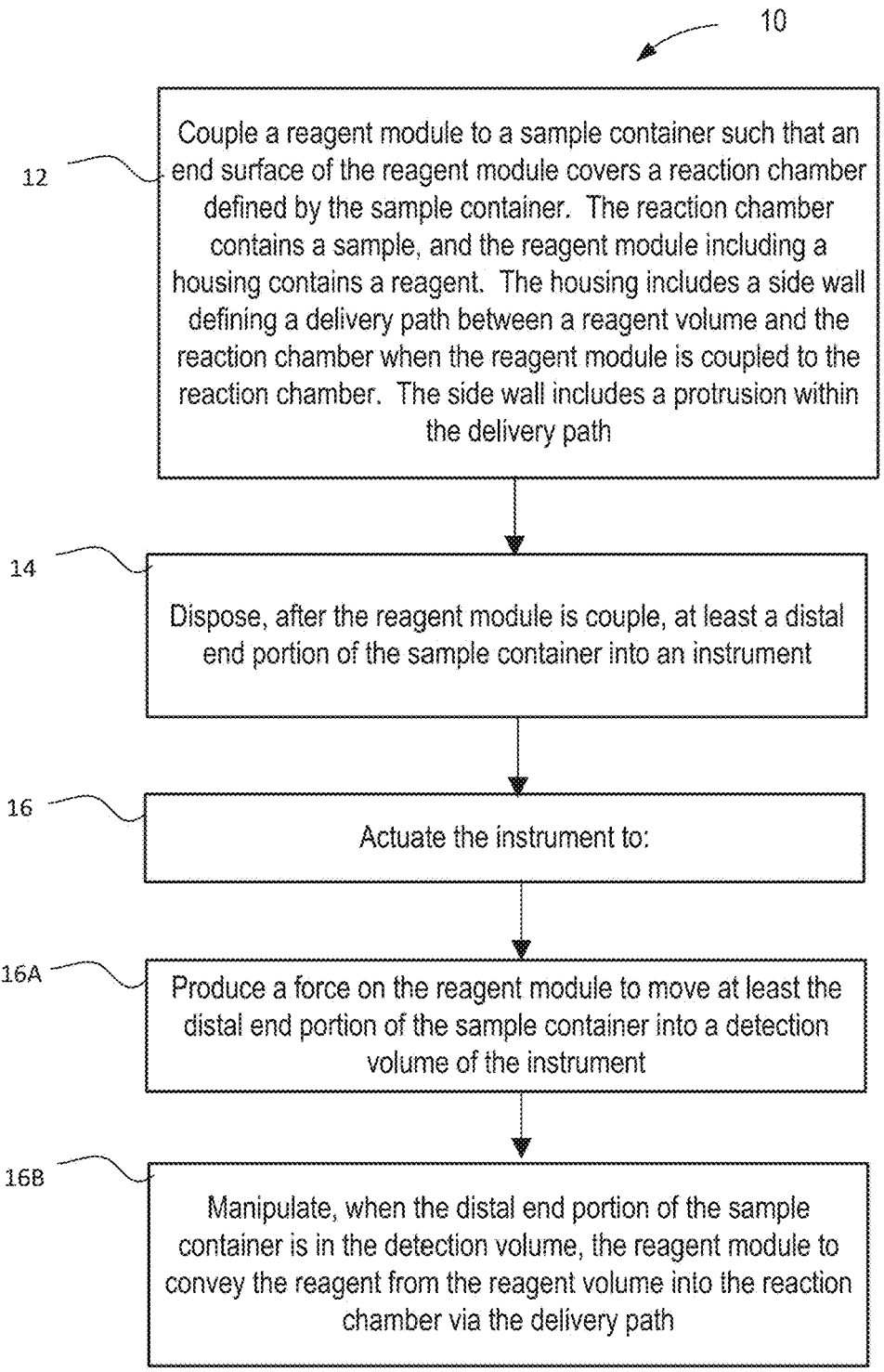
FIG. 36 is a flow chart of a method, according to an embodiment.

Methods of delivering a reagent and performing a detection operation are also described herein. For example, FIG. 36 is a flow chart of a method 10 of delivering a reagent, according to an embodiment. The method 10 can be performed as a part of an assay or molecular diagnostic test of the types described herein, and can be performed as a part of repeatably detecting the presence of a reporter molecule within a sample. The method 10 can be performed using any of the container assemblies and instruments described herein. For example, the method 10 can be performed using any of the container assembly 700, the container assembly 1700, the container assembly 2700, the container assembly 3700, the container assembly 4700, or the container assembly 5700. The method 10 can be performed using the instrument 100 or the instrument 2100 described herein, or any other suitable instrument.

The method 10 includes coupling a reagent module to a sample container such that an end surface of the reagent module covers a reaction chamber defined by the sample container, at 12. The reaction chamber contains a sample, and the reagent module including a housing defining a reagent volume containing a reagent. The housing includes a side wall defining a delivery path between the reagent volume and the reaction chamber when the reagent module is coupled to the reaction chamber. The side wall includes a protrusion within the delivery path. For example, in some embodiments, the reagent module can be the reagent module 2710 and the sample container can be the reaction chamber 2732 as described above. The coupling can be performed, for example, by threadedly coupling the reagent module to the container to create a closed system, as described herein with respect to the container assembly 2700.

At least the distal end portion of the sample container is then placed into an instrument, at 14. The instrument can be, for example, the instrument 2100 described above. The sample container can be placed into the instrument in any suitable manner. For example, in some embodiments, the sample container can be placed in a rack or magazine that is then loaded into the instrument. In other embodiments, the sample container can be placed onto a conveyer system that "feeds" or loads the container into the instrument.

The instrument is then actuated, at 16, to perform one or more operations on (or to manipulate) the container assembly (the assembly of the sample container and the reagent module). The instrument can be actuated by pressing a button, entering a program, or any other suitable method. Specifically, the instrument is actuated to produce a force on the reagent module to move at least the distal end portion of the sample container into a detection volume of the instrument, at 16A, and to manipulate, when the distal end portion of the sample container is in the detection volume, the reagent module to convey the reagent from the reagent volume into the reaction chamber via the delivery path, at 16B.

In some embodiments, the actuating the instrument to manipulate the reagent module includes moving an actuator, such as the actuator 2760 described above, within the reagent volume to produce a flow of the reagent within the delivery path. In such embodiments, the flow can form an exit plume upon exiting the delivery path into the reaction chamber, and the exit plume can be detached from the end surface of the reagent module.

In some embodiments, the actuating the instrument to manipulate the reagent module includes moving an actuator, such as the actuator 2760 described above, at a speed within the reagent volume to produce a flow of the reagent within the delivery path. The speed can be selected such that the flow of the reagent is laminar. In some embodiments, the actuator speed can be between about 30 mm/sec and about 50 mm/sec.

In some embodiments, the method can include conveying a tridecanal solution, of the types shown and described herein. In such embodiments, the actuating the instrument to manipulate the reagent module includes moving an actuator at a speed within the reagent volume to produce a flow of the reagent within the delivery path. The system can be configured and the method can be performed such that a viscosity of the solution, the characteristic diameter, and the speed produce a laminar the flow of the tridecanal.

Figure 37:
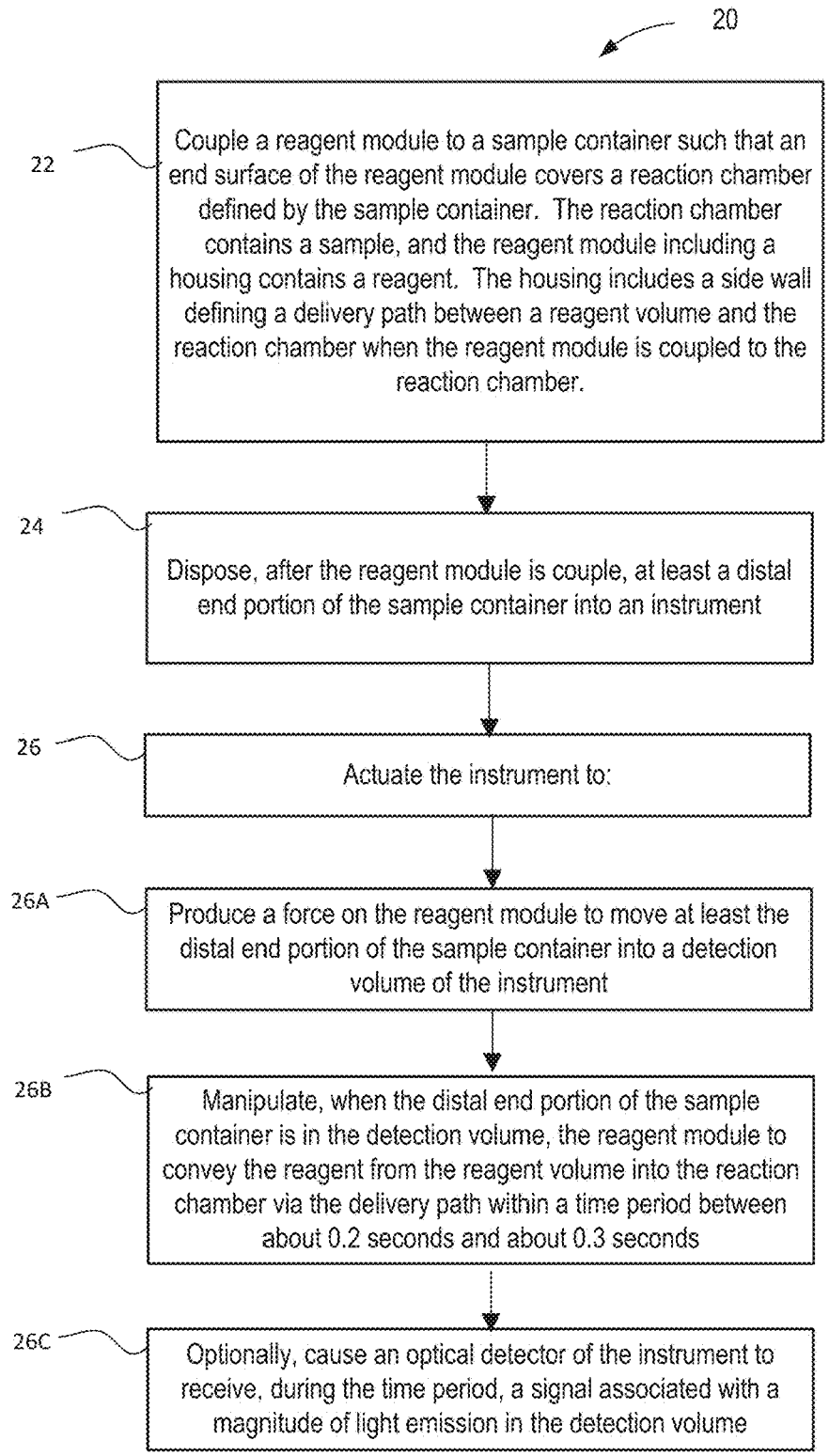
FIG. 37 is a flow chart of a method, according to an embodiment.

FIG. 37 is a flow chart of a method 20 of delivering a reagent, according to an embodiment. The method 20 can be performed as a part of an assay or molecular diagnostic test of the types described herein, and can be performed as a part of repeatably detecting the presence of a reporter molecule within a sample. The method 20 can be performed using any of the container assemblies and instruments described herein. For example, the method 20 can be performed using any of the container assembly 700, the container assembly 1700, the container assembly 2700, the container assembly 3700, the container assembly 4700, or the container assembly 5700. The method 20 can be performed using the instrument 100 or the instrument 2100 described herein, or any other suitable instrument.

The method 20 includes coupling a reagent module to a sample container such that an end surface of the reagent module covers a reaction chamber defined by the sample container, at 22. The reaction chamber contains a sample, and the reagent module including a housing defining a reagent volume containing a reagent. The housing includes a side wall defining a delivery path between the reagent volume and the reaction chamber when the reagent module is coupled to the reaction chamber. For example, in some embodiments, the reagent module can be the reagent module 2710 and the sample container can be the reaction chamber 2732 as described above. The coupling can be performed, for example, by threadedly coupling the reagent module to the container to create a closed system, as described herein with respect to the container assembly 2700.

At least the distal end portion of the sample container is then placed into an instrument, at 24. The instrument can be, for example, the instrument 2100 described above. The sample container can be placed into the instrument in any suitable manner. For example, in some embodiments, the sample container can be placed in a rack or magazine that is then loaded into the instrument. In other embodiments, the sample container can be placed onto a conveyer system that "feeds" or loads the container into the instrument.

The instrument is then actuated, at 26, to perform one or more operations on (or to manipulate) the container assembly (the assembly of the sample container and the reagent module). The instrument can be actuated by pressing a button, entering a program, or any other suitable method. Specifically, the instrument is actuated to produce a force on the reagent module to move at least the distal end portion of the sample container into a detection volume of the instrument, at 26A, and to manipulate, when the distal end portion of the sample container is in the detection volume, the reagent module to convey the reagent from the reagent volume into the reaction chamber via the delivery path within a time period between about 0.2 seconds and about 0.3 seconds, at 26B.

In some embodiments, the actuating the instrument to manipulate the reagent module includes moving an actuator, such as the actuator 2760 described above, within the reagent volume to produce a flow of the reagent within the delivery path. In such embodiments, the flow can form an exit plume upon exiting the delivery path into the reaction chamber, and the exit plume can be detached from the end surface of the reagent module.

In some embodiments, the actuating the instrument to manipulate the reagent module includes moving an actuator, such as the actuator 2760 described above, at a speed within the reagent volume to produce a flow of the reagent within the delivery path. The speed can be selected such that the flow of the reagent is laminar. In some embodiments, the actuator speed can be between about 30 mm/sec and about 50 mm/sec.

In some embodiments, the method 20 the actuating the instrument optionally causes an optical detector of the instrument to receive, during the time period, a signal associated with a magnitude of light emission in the detection volume, 26C.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. Additionally, certain events may be performed concurrently in parallel processes when possible, as well as performed sequentially. While the embodiments have been particularly shown and described, it will be understood that various changes in form and details may be made.

Although various embodiments have been described as having particular features and/or combinations of components, other embodiments are possible having a combination of any features and/or components from any of embodiments as discussed above. Aspects have been described in the general context of molecular diagnostic devices, but inventive aspects are not necessarily limited to use in molecular diagnostic devices.

For example, in some embodiments, any of the container assemblies and/or reagent modules described herein can include any of the protrusions described in connection with the housing 2741.

What is claimed is:

1. An apparatus, comprising:
   a sample tube;
   a housing having a connection portion configured to mate with the sample tube, the housing further including a side wall defining an inner reagent volume of the housing, the housing further comprising a top opening into the inner reagent volume, the housing further including a bottom end wall that separates the inner reagent volume from the sample tube when the housing is coupled to the sample tube, the bottom end wall comprising a puncturer having a sharp point, the bottom end wall further comprising a through hole that defines a delivery path between the inner reagent volume and the sample tube, the bottom end wall further including a plurality of protrusions projecting inwardly from a side surface of the through hole in the bottom end wall into the delivery path;
   a blister container within the inner reagent volume, the blister container containing a reagent and including a frangible portion; and
   an actuator having a plunger coupled to an engagement portion, the engagement portion accessible through the top opening, the engagement portion configured to be manipulated to move the plunger within the inner reagent volume such that the puncturer pierces the frangible portion of the blister container to convey the reagent from the inner reagent volume into the sample tube via the delivery path.

2. The apparatus of claim 1, wherein:
   the bottom end wall defines an exit opening at the end of the through hole through which the reagent is conveyed when the reagent exits the delivery path into the sample tube; and
   the plurality of protrusions project inwardly from the side surface of the through hole in the bottom end wall into the exit opening.

3. The apparatus of claim 1, wherein:
   the delivery path defines a longitudinal center line and has a path length along the longitudinal center line; and
   a protrusion from the plurality of protrusions includes an edge parallel to the longitudinal center line, the edge having a protrusion length of at least ten percent of the path length.

4. The apparatus of claim 1, wherein:
   the delivery path defines a longitudinal center line and has a path length along the longitudinal center line; and
   a protrusion from the plurality of protrusions includes an edge parallel to the longitudinal center line, the edge having a protrusion length of at least half of the path length.

5. The apparatus of claim 4, wherein the protrusion length s substantially equal to the path length.

6. The apparatus of claim 1, wherein:
the delivery path defines a longitudinal center line and a flow area, the flow area bounded by the side surface of the through hole and being within a plane normal to the longitudinal center line, the flow area of the delivery path having a diameter; and
a protrusion from the plurality of protrusions extends inwardly from the side surface of the through hole in the bottom end wall into the flow area by a distance from the side surface, a ratio of the distance to the diameter being between about 0.1 and 0.2.

7. The apparatus of claim 1, wherein:
the delivery path defines a longitudinal center line, a path length, and a flow area, the path length being along the longitudinal center line, the flow area bounded by the side surface of the through hole and being within a plane normal to the longitudinal center line, the flow area of the delivery path having a diameter, a ratio of the path length to the diameter being between about 2.5 and about 3.5.

8. The apparatus of claim 1, wherein:
the delivery path defines a longitudinal center line; and
the plurality of protrusions are equally spaced circumferentially about the longitudinal center line.

9. The apparatus of claim 1, wherein
the reagent is formulated to react with a plurality of reporter molecules in a sample to enhance production of a signal.

10. The apparatus of claim 1, wherein:
the reagent is a first reagent formulated to react with a plurality of reporter molecules in a sample to enhance production of a signal; and
the sample tube containing a second reagent formulated to react with t sample to limit production of the signal.

11. An apparatus, comprising:
a sample tube;
a housing having a connection portion configured to mate with the sample tube, the housing further including a side wall defining an inner reagent volume of the housing, the housing further comprising a top opening into the inner reagent volume, the housing further including a bottom end wall that separates the inner reagent volume from the sample tube when the housing is coupled to the sample tube, the bottom end wall comprising a puncturer having a sharp point, the bottom end wall further comprising a through hole that defines a delivery path between the inner reagent volume and the sample tube, a lower-most surface of the bottom end wall defining an exit opening of the through hole through which an exit flow of a reagent is conveyed when exiting the delivery path, the bottom end wall further including a plurality of protrusions projecting inwardly from a side surface of the through hole in the bottom end wall into the exit opening;
a blister container within the inner reagent volume, the blister container containing the reagent and including a frangible portion; and
an actuator having a plunger coupled to an engagement portion, the engagement portion accessible through the top opening, the engagement portion configured to be manipulated such that the puncturer pierces the frangible portion of the blister container to produce the exit flow of the reagent through the delivery path and the exit opening.

12. The apparatus of claim 11, wherein:
the delivery path defines a longitudinal center line and a flow area, the flow area bounded by the side surface of the through hole and being within a plane normal to the longitudinal center line, the flow area of the delivery path having a diameter; and
a protrusion from the plurality of protrusions extends inwardly from the side surface of the through hole in the bottom end wall into the exit opening by a distance from the side surface, a ratio of the distance to the diameter being between about 0.1 and 0.2.

13. The apparatus of claim 11, wherein the plurality of protrusions project inwardly from the side surface of the through hole in the bottom end wall into the delivery path.

14. The apparatus of claim 13, wherein:
the delivery path defines a longitudinal center line and has a path length along the longitudinal center line; and
a protrusion from the plurality of protrusions includes an edge parallel to the longitudinal center line, the edge having an edge length of at least half of the path length.

15. The apparatus of claim 11, wherein the bottom end wall defines a flow area along a path length within the delivery path, the flow area bounded by the side surface of the through hole and being within a plane normal to a longitudinal center line of the delivery path, the plurality of protrusion positioned within the delivery path such that a shape of the flow area is discontinuous.

16. The apparatus of claim 11, wherein the plurality of protrusions are equally spaced circumferentially about a longitudinal center line of the delivery path.

* * * * *